US010092645B2

(12) United States Patent
Stewart et al.

(10) Patent No.: US 10,092,645 B2
(45) Date of Patent: Oct. 9, 2018

(54) METHODS OF TREATMENT WITH ANTAGONISTS AGAINST PD-1 AND PD-L1 IN COMBINATION WITH RADIATION THERAPY

(71) Applicants: MedImmune Limited, Cambridge (GB); The University of Manchester, Manchester (GB)

(72) Inventors: Ross Stewart, Cambridge (GB); Michelle Morrow, Cambridge (GB); Robert Wilkinson, Cambridge (GB); Edmund Poon, Cambridge (GB); Simon Dovedi, Manchester (GB); Tim Illidge, Manchester (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 14/740,876

(22) Filed: Jun. 16, 2015

(65) Prior Publication Data

US 2016/0051672 A1   Feb. 25, 2016

Related U.S. Application Data

(60) Provisional application No. 62/013,157, filed on Jun. 17, 2014.

(51) Int. Cl.
| | | |
|---|---|---|
| *A61K 39/395* | (2006.01) | |
| *A61N 5/10* | (2006.01) | |
| *C07K 16/28* | (2006.01) | |
| *A61K 39/00* | (2006.01) | |

(52) U.S. Cl.
CPC .... *A61K 39/3955* (2013.01); *A61K 39/39558* (2013.01); *A61N 5/10* (2013.01); *C07K 16/2818* (2013.01); *C07K 16/2827* (2013.01); *A61K 2039/505* (2013.01); *C07K 2317/73* (2013.01)

(58) Field of Classification Search
None
See application file for complete search history.

(56) References Cited

FOREIGN PATENT DOCUMENTS

| WO | WO 2012177624 A2 | 12/2012 |
| WO | WO 2013190555 A1 | 12/2013 |

OTHER PUBLICATIONS

Zeng et al (Int J Radiat Oncol Biol Phys, 2013, 86(2): 343-349).*
Hamid et al (NEJM, 2013, 369(2): 134-144).*
Khan et al (OncoTargets and Therapy, 2011, 4: 137-148).*
Chang et al (Int J Radiation Oncology Biol Phys, 2006, 66(4): 1051-1055).*
Brahmer et al (NEJM, 2012, 366(26): 2455-2465).*
Stewart et al (Cancer Res, 2011, 71; LB-158; Abstract).*
Verbrugge et al (Cancer Research, 2012, 72(13): 3163-3174).*
Strogan (Radiol Oncol, 2010, 44(1): 1-12).*
Deng, L., et al., "Irradiation and anti-PD-L1 treatment synergistically promote antitumor immunity in mice," Journal of Clinical Investigation, 124(2): 687-695 (2014).
Dovedi, S., et al., "Acquired Resistance to Fractionated Radiotherapy Can Be Overcome by Concurrent PD-L1 Blockade," Cancer Research, 74(19): 5458-5468 (2014).
Liang, H., et al., "Radiation-Induced Equilibrium is a Balance between Tumor Cell Proliferation and T Cell-Mediated Killing," Journal of Immunology, 190: 5874-5881 (2013).
Zeng, J., et al., "Anti-PD-1 Blockade and Stereotactic Radiation Produce Long-Term Survival in Mice With Intracranial Gliomas," International Journal of Radiation Oncology Biology Physics, 86(2): 343-349 (2013).
International Search Report dated Sep. 3, 2015, in connection with corresponding International Application No. PCT/EP2015/063552.
Lugade, Amit A., et al., "Local Radiation Therapy of B16 Melanoma Tumors Increases the Generation of Tumor Antigen-Specific Effector Cells That Traffic to the Tumor," J. Immunol. 2005; 174:7516-7523.
Reits,m Eric A., et al., "Radiation modulates the peptide repertoire, enhances MHC class I expression, and induces successful antitumor immunotherapy," JEM The Rockefeller University Press, vol. 203, No. 5, May 15, 2006, 1259-1271.
Huang, Qian, et al., "Caspase 3-mediated stimulation of tumor cell repopulation during cancer radiotherapy," Nature Medicine, vol. 17, No. 7, Jul. 2011, 860-867.

\* cited by examiner

*Primary Examiner* — Sean E Aeder

(57) ABSTRACT

This application provides a method of treating cancer in a patient comprising administering at least one dose of radiation therapy and at least one PD-1 and/or PD-L1 antagonist, wherein at least one PD-1 and/or PD-L1 antagonist is administered on the same day as a dose of radiation therapy or up to and including 4 days later.

17 Claims, 36 Drawing Sheets

Specification includes a Sequence Listing.

A. αPD-L1 mAb starting on day 1 of RT
B. αPD-L1 mAb starting on day 5 of RT
C. αPD-L1 mAb starting 7 days after the last dose of RT

SEQUENCE LISTING

```
<160> NUMBER OF SEQ ID NOS: 93

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Asp Tyr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Lys Ala Glu Asp Thr Ala Val Tyr Tyr Cys
                85                  90                  95

Ala Arg Asp Leu Val Thr Ser Met Val Ala Phe Asp Tyr Trp Gly Gln
            100                 105                 110

Gly Thr Leu Val Thr Val Ser Ser
        115                 120

<210> SEQ ID NO 2
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Cys Ser Gly Asp Ala Leu Pro Gln Lys Tyr Val Phe Trp Tyr Gln
1               5                   10                  15

Gln Lys Ser Gly Gln Ala Pro Val Leu Val Ile Tyr Glu Asp Ser Lys
            20                  25                  30

Arg Pro Ser Gly Ile Pro Glu Arg Phe Ser Gly Ser Ser Ser Gly Thr
        35                  40                  45

Met Ala Thr Leu Thr Ile Ser Gly Ala Gln Val Glu Asp Glu Ala Asp
    50                  55                  60

Tyr Tyr Cys Tyr Ser Thr Asp Arg Ser Gly Asn His Arg Val Phe Gly
65                  70                  75                  80

Gly Gly Thr Arg Leu Thr Val Leu
                85

<210> SEQ ID NO 3
<211> LENGTH: 120
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Gly Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asn Tyr Gly Tyr Tyr Asp Met Asp Val Trp Gly Gln
            100                 105                 110

Gly Thr Thr Val Thr Val Ser Ser
        115                 120

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Phe Gln Gln Lys Pro Gly Gln Ala Pro Arg Leu Leu
        35                  40                  45

Ile Phe Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ile
                85                  90                  95

Phe Thr Phe Gly Pro Gly Thr Lys Val Asp Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Leu Ala Phe Asp Tyr Trp Gly
                100                 105                 110

Gln Gly Thr Leu Val Thr Val Ser Ser
            115                 120

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Glu Val Glu Ile Lys
                100                 105

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ala Ile Arg Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Tyr Asp Ser Ser Gly Tyr Leu Asp Tyr Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Lys Leu Leu Ile
        35                  40                  45

Tyr Ala Ile Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Gly Glu Lys Tyr Tyr Val Asp Ser Val
50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Val Gln Leu Tyr Ser Asp Tyr Phe Asp Tyr Trp Gly Gln Gly
            100                 105                 110

Thr Leu Val Thr Val Ser Ser
        115

<210> SEQ ID NO 10
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Ser Gly Lys Ala Pro Lys Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser His Ser Leu Pro Pro
                85                  90                  95

Thr Phe Gly Gln Gly Thr Lys Val Glu Ile Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Phe Thr Phe Ser Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Ser Ala Val Tyr Ser Cys
                85                  90                  95

Ala Lys Val Leu Val Gly Phe Asn Asn Gly Cys Trp Asp Tyr Trp Gly
            100                 105                 110

Gln Gly Thr Leu Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30
```

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asn Asp His
                85                  90                  95

Val Val Phe Gly Gly Gly Thr Lys Leu Thr Val Leu
            100                 105

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
            35                  40                  45

Ser Ser Ile Ser Ser Ser Gly Asp Tyr Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Val Thr Ser Met Val Ala Phe Asp Tyr Trp Gly Gln
            100                 105                 110

Gly Thr Leu Val Thr Val Ser Ser
            115                 120

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Gln Lys Tyr Val
            20                  25                  30

Phe Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Arg Ser Gly Asn His
                85                  90                  95

```
Arg Val Phe Gly Gly Gly Thr Lys Leu Thr Val Leu
            100                 105
```

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120
```

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 17
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Lys Leu Gln Glu Ser Gly Pro Ser Leu Val Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Val
        35                  40                  45

Gly Tyr Ile Ser Tyr Thr Gly Ser Thr Tyr Asn Pro Ser Leu Lys
50                  55                  60

Ser Arg Ile Ser Ile Thr Arg Asp Thr Ser Lys Asn Gln Tyr Tyr Leu
65                  70                  75                  80

Gln Leu Asn Ser Val Thr Ser Glu Asp Thr Ala Thr Tyr Tyr Cys Ala
                85                  90                  95

Arg Tyr Gly Gly Trp Leu Ser Pro Phe Asp Tyr Trp Gly Gln Gly Thr
            100                 105                 110

Thr Leu Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Asp Ser Ser Tyr Pro Leu
                85                  90                  95

Thr Phe Gly Ala Gly Thr Lys Val Glu Leu Lys
            100                 105

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Ser Ile Asn Trp Ile Arg Gln Pro Pro Gly Lys Gly Leu Glu Trp Leu
        35                  40                  45

Gly Val Met Trp Ala Gly Gly Gly Thr Asn Ser Asn Ser Val Leu Lys

```
                    50                  55                  60
Ser Arg Leu Ile Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                    85                  90                  95

Arg Tyr Tyr Gly Asn Ser Pro Tyr Tyr Ala Ile Asp Tyr Trp Gly Gln
                100                 105                 110

Gly Thr Ser Val Thr Val Ser Ser
            115                 120

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Thr Thr Gln Ser His Lys Leu Met Ser Thr Ser Val Gly
 1               5                  10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
                35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Asp Ser Ser Tyr Pro Leu
                85                  90                  95

Thr Phe Gly Ala Gly Thr Lys Val Glu Leu Lys
                100                 105

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Lys Leu Gln Glu Ser Gly Pro Ser Leu Val Lys Pro Ser Gln
 1               5                  10                  15

Thr Leu Ser Leu Thr Cys Ser Val Thr Gly Tyr Ser Ile Ile Ser Asp
                20                  25                  30

Tyr Trp Asn Trp Ile Arg Lys Phe Pro Gly Asn Lys Leu Glu Tyr Leu
                35                  40                  45

Gly Tyr Ile Ser Tyr Thr Gly Ser Thr Tyr Tyr Asn Pro Ser Leu Lys
                50                  55                  60

Ser Arg Ile Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ala
                85                  90                  95

Arg Arg Gly Gly Trp Leu Leu Pro Phe Asp Tyr Trp Gly Gln Gly Thr
                100                 105                 110

Thr Leu Thr Val Ser Ser
```

<210> SEQ ID NO 22
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Ile Val Met Thr Gln Ser Pro Ser Ser Leu Ala Val Ser Val Gly
1               5                   10                  15

Glu Lys Val Ser Met Gly Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Asp Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys
```

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Lys Leu Gln Glu Ser Gly Pro Ser Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Phe Pro Arg Asp Asn Asn Thr Lys Tyr Asn Glu Asn Phe
    50                  55                  60

Lys Gly Lys Ala Thr Leu Thr Val Asp Thr Ser Ser Thr Thr Ala Tyr
65                  70                  75                  80

Met Glu Leu His Ser Leu Thr Ser Glu Asp Ser Ala Val Tyr Phe Cys
                85                  90                  95

Thr Lys Glu Asn Trp Val Gly Asp Phe Asp Tyr Trp Gly Gln Gly Thr
            100                 105                 110

Thr Leu Thr Leu Ser Ser
        115
```

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Ile Arg Tyr Met
            20                  25                  30

His Trp Tyr Gln Gln Lys Pro Gly Thr Ser Pro Lys Arg Trp Ile Ser
        35                  40                  45

Asp Thr Ser Lys Leu Thr Ser Gly Val Pro Ala Arg Phe Ser Gly Ser
    50                  55                  60

Gly Ser Gly Thr Ser Tyr Ala Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys
            100                 105

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Gln Gln Ser Gly Pro Asp Leu Val Thr Pro Gly Ala
1               5                   10                  15

Ser Val Arg Ile Ser Cys Gln Ala Ser Gly Tyr Thr Phe Pro Asp Tyr
            20                  25                  30

Tyr Met Asn Trp Val Lys Gln Ser His Gly Lys Ser Leu Glu Trp Ile
        35                  40                  45

Gly Asp Ile Asp Pro Asn Tyr Gly Gly Thr Thr Tyr Asn Gln Lys Phe
    50                  55                  60

Lys Gly Lys Ala Ile Leu Thr Val Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ala Leu Thr Asp Trp Gly Gln Gly Thr Ser Leu Thr Val
            100                 105                 110

Ser Ser

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

Tyr Trp Phe Gln Gln Lys Pro Gly Ser Ser Pro Lys Pro Trp Ile Tyr
        35                  40                  45

Ala Thr Phe Asn Leu Ala Ser Gly Val Pro Ala Arg Phe Ser Gly Ser

```
            50                  55                  60
Gly Ser Gly Thr Ser Tyr Ser Leu Thr Ile Ser Arg Val Glu Thr Glu
 65                  70                  75                  80

Asp Ala Ala Thr Tyr Tyr Cys Gln Gln Trp Ser Asn Asn Pro Leu Thr
                 85                  90                  95

Phe Gly Ala Gly Thr Lys Leu Glu Leu Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Gln Gln Ser Gly Pro Val Leu Val Lys Pro Gly Ala
 1               5                  10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asn Ile Asn Pro Tyr Asn Gly Gly Thr Thr Tyr Asn Gln Lys Phe
        50                  55                  60

Lys Gly Lys Ala Thr Leu Thr Val Asp Lys Ser Ser Arg Thr Ala Tyr
 65                  70                  75                  80

Met Glu Ile Asn Ser Leu Thr Ser Glu Asp Ser Ala Val Tyr Tyr Cys
                 85                  90                  95

Ala Arg Gly Arg Ile Tyr Asp Gly Ser Leu Asp Tyr Trp Gly Gln Gly
            100                 105                 110

Thr Ala Leu Thr Val Ser Ser
        115

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Phe Pro Ser Ser Leu Cys Ala Ser Gln Gly
 1               5                  10                  15

Gly Lys Val Thr Val Thr Cys Lys Ala Ser Gln Asp Ile Asn Asn Tyr
                20                  25                  30

Met Ala Trp Tyr Gln His Lys Pro Gly Lys Gly Pro Arg Leu Leu Ile
            35                  40                  45

His Tyr Thr Ser Thr Leu Leu Ser Gly Ile Pro Ser Arg Phe Ser Gly
        50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Trp Thr
                 85                  90                  95

Phe Gly Gly Gly Thr Lys Leu Glu Ile Lys
            100                 105
```

```
<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Ser Gly Ala Glu Leu Ala Lys Pro Gly Ala
1               5                   10                  15

Ser Val Arg Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly His Ile Asn Pro Ser Ser Gly Phe Thr Thr Tyr Asn Gln Asn Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Tyr Glu Asp Ser Ala Val Tyr Phe Cys
                85                  90                  95

Ala Arg Glu Asp Tyr Asp Val Asp Tyr Trp Gly Gln Gly Thr Thr Leu
            100                 105                 110

Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Ser Gln Lys Phe Met Ser Thr Ser Val Gly
1               5                   10                  15

Asp Arg Val Ser Val Thr Cys Lys Ala Ser Gln Ser Val Asp Thr Asn
            20                  25                  30

Val Ala Trp Tyr Gln Gln Lys Pro Gly Gln Ser Pro Lys Ala Leu Ile
        35                  40                  45

Phe Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Ser Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Ser Gly Thr Lys Leu Glu Ile Lys
            100                 105

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Lys Pro Gly Gly
1               5                   10                  15
```

```
Ser Leu Lys Leu Ser Cys Ala Ala Ser Gly Phe Thr Phe Ser Asp Tyr
        20                  25                  30

Gly Met His Trp Val Arg Gln Ala Pro Glu Lys Gly Leu Glu Trp Val
            35                  40                  45

Ala Tyr Ile Ser Ser Gly Ser Tyr Thr Ile Tyr Tyr Thr Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
            115                 120
```

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Ile Val Leu Thr Gln Ser Pro Ala Leu Met Ser Ala Ser Pro Gly
 1               5                  10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys
            100                 105
```

<210> SEQ ID NO 33
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Gly Leu Glu Trp Met
            35                  40                  45

Gly Asp Ile Asp Pro Asn Tyr Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80
```

```
Met Glu Leu Ser Arg Leu Arg Ser Asp Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 34
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Ser Leu Glu Trp Met
        35                  40                  45

Gly Asp Ile Asp Pro Asn Tyr Gly Gly Thr Asn Tyr Asn Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 35
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Ser Leu Glu Trp Met
        35                  40                  45

Gly Asp Ile Asp Pro Asn Tyr Gly Gly Thr Asn Tyr Asn Gln Lys Phe
    50                  55                  60

Gln Gly Arg Val Thr Met Thr Val Asp Arg Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 36
```

<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
            20                  25                  30

Tyr Met Asn Trp Val Arg Gln Ala Pro Gly Lys Gly Leu Glu Trp Val
        35                  40                  45

Gly Asp Ile Asp Pro Asn Tyr Gly Gly Thr Thr Tyr Ala Ala Ser Val
    50                  55                  60

Lys Gly Arg Phe Thr Ile Ser Val Asp Arg Ser Lys Ser Ile Ala Tyr
65                  70                  75                  80

Leu Gln Met Ser Ser Leu Lys Thr Glu Asp Thr Ala Val Tyr Tyr Cys
                85                  90                  95

Thr Arg Gly Ala Leu Thr Asp Trp Gly Gln Gly Thr Met Val Thr Val
            100                 105                 110

Ser Ser

<210> SEQ ID NO 37
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
            20                  25                  30

Tyr Met Asn Trp Val Arg Gln Ala Pro Gly Lys Gly Leu Glu Trp Val
        35                  40                  45

Gly Asp Ile Asp Pro Asn Tyr Gly Gly Thr Thr Tyr Asn Ala Ser Val
    50                  55                  60

Lys Gly Arg Phe Thr Ile Ser Val Asp Arg Ser Lys Ser Ile Ala Tyr
65                  70                  75                  80

Leu Gln Met Ser Ser Leu Lys Thr Glu Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 38
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Arg
1               5                   10                  15

```
Ser Leu Arg Leu Ser Cys Thr Ala Ser Gly Tyr Thr Phe Pro Asp Tyr
            20                  25                  30

Tyr Met Asn Trp Val Arg Gln Ala Pro Gly Lys Gly Leu Glu Trp Val
         35                  40                  45

Gly Asp Ile Asp Pro Asn Tyr Gly Gly Thr Thr Tyr Asn Gln Ser Val
 50                  55                  60

Lys Gly Arg Phe Thr Ile Ser Val Asp Arg Ser Lys Ser Ile Ala Tyr
 65                  70                  75                  80

Leu Gln Met Ser Ser Leu Lys Thr Glu Asp Thr Ala Val Tyr Tyr Cys
             85                  90                  95

Ala Arg Gly Ala Leu Thr Asp Trp Gly Gln Gly Thr Met Val Thr Val
            100                 105                 110

Ser Ser

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

Tyr Trp Phe Gln Gln Lys Pro Gly Gln Ala Pro Arg Leu Leu Ile Tyr
         35                  40                  45

Ala Ala Phe Asn Arg Ala Thr Gly Ile Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Asn Asn Pro Leu Thr
             85                  90                  95

Phe Gly Gln Gly Thr Lys Val Glu Ile Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

Tyr Trp Phe Gln Gln Lys Pro Gly Gln Ser Pro Arg Pro Leu Ile Tyr
         35                  40                  45

Ala Ala Phe Asn Arg Ala Thr Gly Ile Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80
```

```
Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 41
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

Tyr Trp Phe Gln Gln Lys Pro Gly Gln Ser Pro Arg Pro Leu Ile Tyr
        35                  40                  45

Ala Thr Phe Asn Leu Ala Ser Gly Ile Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Gly Val Ser Tyr Ile
            20                  25                  30

Tyr Trp Phe Gln Gln Lys Pro Gly Lys Ala Pro Lys Leu Leu Ile Tyr
        35                  40                  45

Ala Ala Phe Asn Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 43
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 43

Asp Ile Gln Leu Thr Gln Ser Pro Ser Leu Ser Ala Ser Val Gly
1               5                   10                  15

Asp Arg Val Thr Ile Thr Cys Arg Ala Ser Ser Gly Val Ser Tyr Ile
            20                  25                  30

Tyr Trp Phe Gln Gln Lys Pro Gly Lys Ala Pro Lys Pro Leu Ile Tyr
        35                  40                  45

Ala Ala Phe Asn Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Leu Thr Gln Ser Pro Ser Ile Leu Ser Ala Ser Val Gly
1               5                   10                  15

Asp Arg Val Thr Ile Thr Cys Arg Ala Ser Ser Val Ser Tyr Ile
            20                  25                  30

Tyr Trp Phe Gln Gln Lys Pro Gly Lys Ala Pro Lys Pro Leu Ile Tyr
        35                  40                  45

Ala Thr Phe Asn Leu Ala Ser Gly Val Pro Ser Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Thr Leu Tyr
```

```
                65                  70                  75                  80
Leu Gln Met Ser Ser Leu Arg Ala Glu Asp Thr Ala Val Tyr Tyr Cys
                        85                  90                  95

Ala Arg Arg Gly Tyr Gly Ser Phe Tyr Glu Tyr Tyr Phe Asp Tyr Trp
                100                 105                 110

Gly Gln Gly Thr Thr Val Thr Val Ser Ser
            115                 120

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Ser Tyr Thr Ile Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                        85                  90                  95

Ala Arg Arg Gly Tyr Gly Ser Phe Tyr Glu Tyr Tyr Phe Asp Tyr Trp
                100                 105                 110

Gly Gln Gly Thr Thr Val Thr Val Ser Ser
            115                 120

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Ser Tyr Thr Ile Tyr Ser Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                        85                  90                  95

Ala Arg Arg Gly Tyr Gly Ser Phe Tyr Glu Tyr Tyr Phe Asp Tyr Trp
                100                 105                 110

Gly Gln Gly Thr Thr Val Thr Val Ser Ser
```

<210> SEQ ID NO 48
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
                20                  25                  30

Gly Met His Trp Val Arg Gln Ala Pro Gly Gln Arg Leu Glu Trp Met
            35                  40                  45

Gly Tyr Ile Ser Ser Gly Ser Ser Thr Ile Tyr Tyr Ser Gln Lys Phe
        50                  55                  60

Gln Gly Arg Val Thr Ile Thr Arg Asp Asn Ser Ala Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Asp Tyr
                20                  25                  30

Gly Met His Trp Val Arg Gln Ala Pro Gly Gln Arg Leu Glu Trp Met
            35                  40                  45

Gly Tyr Ile Ser Ser Gly Ser Tyr Thr Ile Tyr Tyr Ser Gln Lys Phe
        50                  55                  60

Gln Gly Arg Val Thr Ile Thr Arg Asp Asn Ser Ala Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120

<210> SEQ ID NO 50
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Glu Val Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Asp Tyr
            20                  25                  30

Gly Met His Trp Val Arg Gln Ala Pro Gly Gln Arg Leu Glu Trp Val
        35                  40                  45

Ala Tyr Ile Ser Ser Gly Ser Tyr Thr Ile Tyr Tyr Ser Gln Lys Phe
    50                  55                  60

Gln Gly Arg Val Thr Ile Thr Arg Asp Asn Ser Ala Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120

<210> SEQ ID NO 51
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Leu Ala Ser Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 52
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Arg Ala Thr Gly Ile Pro Ala Arg Phe Ser Gly Ser
            50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Phe Thr
                 85                  90                  95

Phe Gly Gln Gly Thr Lys Leu Glu Ile Lys
            100                 105

<210> SEQ ID NO 53
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Ser Ser Val Ser Tyr Met
             20                  25                  30

Tyr Trp Tyr Gln Gln Lys Pro Gly Lys Ala Pro Lys Leu Leu Ile Tyr
         35                  40                  45

Leu Ala Ser Asn Leu Ala Ser Gly Val Pro Ser Arg Phe Ser Gly Ser
     50                  55                  60

Gly Ser Gly Thr Glu Tyr Thr Leu Thr Ile Ser Ser Leu Glu Pro Glu
 65                  70                  75                  80

Asp Phe Ala Thr Tyr Tyr Cys Gln Gln Trp Ser Ser Asn Pro Phe Thr
                 85                  90                  95

Phe Gly Gln Gly Thr Lys Leu Glu Ile Lys
            100                 105

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
             20                  25                  30

Tyr Trp Tyr Gln Gln Lys Pro Gly Lys Ala Pro Lys Leu Leu Ile Tyr
         35                  40                  45

Leu Thr Ser Asn Leu Ala Ser Gly Val Pro Ser Arg Phe Ser Gly Ser
     50                  55                  60

Gly Ser Gly Thr Glu Tyr Thr Leu Thr Ile Ser Ser Leu Glu Pro Glu
 65                  70                  75                  80

Asp Phe Ala Thr Tyr Tyr Cys Gln Gln Trp Ser Ser Asn Pro Phe Thr
                 85                  90                  95

Phe Gly Gln Gly Thr Lys Leu Glu Ile Lys
            100                 105

<210> SEQ ID NO 55

<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Glu Ser Gly Gly Asp Val Val Gln Pro Gly Gly
1               5                   10                  15

Ser Leu Arg Leu Ser Cys Ala Ala Ser Gly Val Ala Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Met Tyr Tyr Cys
                85                  90                  95

Ala Arg Asn Asp Asp Tyr Trp Gly Gln Gly Thr Leu Val Thr Val Ser
            100                 105                 110

Ser

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Ile Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Glu Ser Gly Gly Asp Val Val Gln Pro Gly Arg
1               5                   10                  15

Ser Leu Arg Leu Ser Cys Ala Ala Ser Gly Leu Thr Phe Thr Asn Tyr

```
                20                  25                  30
Gly Phe His Trp Val Arg Gln Ala Pro Gly Lys Gly Leu Glu Trp Val
            35                  40                  45

Ala Val Ile Trp Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Thr Gly Asp Asp Tyr Trp Gly Gln Gly Thr Leu Val Thr Val Ser
            100                 105                 110

Ser

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 59
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Tyr Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Val Glu Asp Thr Ala Val Tyr Tyr Cys
                85                  90                  95
```

Ala Ser Asn Val Asp His Trp Gly Gln Gly Thr Leu Val Thr Val Ser
            100                 105                 110

Ser

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Arg Ser
            20                  25                  30

Ser Phe Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Asp Tyr Asp Ile Leu Thr Gly Asp Glu Asp Tyr Trp Gly
            100                 105                 110

Gln Gly Thr Leu Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

```
Tyr Ala Ala Ser Asn Leu Arg Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Arg
                 85                  90                  95

Thr Phe Gly Gln Gly Thr Lys Val Glu Ile Lys
                100                 105
```

<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Gln Val Gln Leu Val Glu Ser Gly Gly Gly Val Val Gln Pro Gly Arg
  1               5                  10                  15

Ser Leu Arg Leu Ser Cys Thr Thr Ser Gly Ile Thr Phe Ser Ser Tyr
                 20                  25                  30

Gly Phe His Trp Val Arg Gln Ala Pro Gly Lys Gly Leu Glu Trp Val
             35                  40                  45

Ala Val Ile Trp Tyr Asp Gly Ser Lys Lys Tyr Tyr Ala Asp Ser Val
         50                  55                  60

Lys Gly Arg Phe Thr Leu Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Thr Gly Asp Asp Tyr Trp Gly Gln Gly Thr Leu Val Thr Val Ser
                100                 105                 110

Ser
```

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
                100                 105
```

-continued

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Leu Ser Arg Ser
            20                  25                  30

Ser Tyr Phe Trp Gly Trp Ile Arg Gln Pro Pro Gly Lys Gly Leu Glu
        35                  40                  45

Trp Ile Ala Ser Ile Phe Tyr Ser Gly Glu Thr Tyr Phe Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Asp Glu Asp Tyr Trp Gly
            100                 105                 110

Gln Gly Thr Leu Val Thr Val Ser Ser
        115                 120

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Arg
                85                  90                  95

Thr Phe Gly Gln Gly Thr Lys Val Glu Ile Lys
            100                 105

<210> SEQ ID NO 69
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Ala

```
                 1               5                  10                 15
Ser Val Lys Val Ser Cys Lys Ala Ser Gly Tyr Thr Phe Thr Asp Tyr
                20                 25                 30

Gly Phe Ser Trp Val Arg Gln Ala Pro Gly Gln Gly Leu Glu Trp Met
                35                 40                 45

Gly Trp Ile Thr Ala Tyr Asn Gly Asn Thr Asn Tyr Ala Gln Lys Leu
     50                 55                 60

Gln Gly Arg Val Thr Met Thr Thr Asp Thr Ser Thr Ser Thr Val Tyr
65                 70                 75                 80

Met Glu Leu Arg Ser Leu Arg Ser Asp Asp Thr Ala Val Tyr Tyr Cys
                85                 90                 95

Ala Arg Asp Tyr Phe Tyr Gly Met Asp Val Trp Gly Gln Gly Thr Thr
               100                105                110

Val Thr Val Ser Ser
          115
```

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Glu Ile Val Leu Thr Gln Ser Pro Ala Thr Leu Ser Leu Ser Pro Gly
1               5                  10                 15

Glu Arg Ala Thr Leu Ser Cys Arg Ala Ser Gln Ser Val Ser Ser Tyr
                20                 25                 30

Leu Val Trp Tyr Gln Gln Lys Pro Gly Gln Ala Pro Arg Leu Leu Ile
                35                 40                 45

Tyr Asp Ala Ser Asn Arg Ala Thr Gly Ile Pro Ala Arg Phe Ser Gly
     50                 55                 60

Ser Gly Ser Gly Thr Asp Phe Thr Leu Thr Ile Ser Ser Leu Glu Pro
65                 70                 75                 80

Glu Asp Phe Ala Val Tyr Tyr Cys Gln Gln Arg Ser Asn Trp Pro Arg
                85                 90                 95

Thr Phe Gly Gln Gly Thr Lys Val Glu Ile Lys
               100                105
```

<210> SEQ ID NO 71
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Gln Val Gln Leu Val Gln Ser Gly Ala Glu Val Lys Lys Pro Gly Ser
1               5                  10                 15

Ser Val Lys Val Ser Cys Lys Thr Ser Gly Asp Thr Phe Ser Thr Tyr
                20                 25                 30

Ala Ile Ser Trp Val Arg Gln Ala Pro Gly Gln Gly Leu Glu Trp Met
                35                 40                 45

Gly Gly Ile Ile Pro Ile Phe Gly Lys Ala His Tyr Ala Gln Lys Phe
     50                 55                 60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Phe Cys
                    85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 72
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr
                85

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
            100                 105                 110

Leu Val Thr Val Ser Ser
        115

<210> SEQ ID NO 74
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 75
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Val Ser Gly Gly Ile Phe Ser Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Ala Asn His Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Gly Ile Ala Ala Ala Leu Phe Asp Tyr Trp Gly Gln
            100                 105                 110

Gly Thr Leu Val Thr Val Ser Ser
        115                 120

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
                100                 105

<210> SEQ ID NO 77
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
                20                  25                  30

Val Val His Trp Val Arg Gln Ala Pro Gly Lys Gly Leu Glu Trp Val
            35                  40                  45

Ser Gly Ile Ser Gly Asn Ser Gly Asn Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Val Pro Phe Asp Tyr Trp Gly Gln Gly Thr Leu Val Thr Val Ser
                100                 105                 110

Ser

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

```
Thr Phe Gly Gln Gly Thr Lys Leu Glu Ile Lys
            100                 105
```

<210> SEQ ID NO 79
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

<210> SEQ ID NO 80
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 81
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Tyr Asp Tyr Val Ser Gly Ser Pro Phe Gly Met Asp Val
            100                 105                 110

Trp Gly Gln Gly Thr Thr Val Thr Val Ser Ser
            115                 120

<210> SEQ ID NO 82
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 83
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Ser Ala Asn Tyr Ala Gln Lys Phe

```
                    50                  55                  60
Gln Asp Arg Val Thr Ile Thr Ala Asp Glu Ser Thr Ser Ala Ala Tyr
 65                  70                  75                  80

Met Glu Leu Ser Ser Leu Arg Ser Glu Asp Thr Ala Val Tyr Tyr Cys
                     85                  90                  95

Ala Arg Asp Ser Ser Gly Trp Ser Arg Tyr Tyr Met Asp Val Trp Gly
                100                 105                 110

Gln Gly Thr Thr Val Thr Val Ser Ser
            115                 120

<210> SEQ ID NO 84
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Phe Gly Gly Gly Thr Lys Val Glu Ile Lys
            100                 105

<210> SEQ ID NO 85
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Gln Ser Gly Ala Glu Val Lys Glu Pro Gly Ser
 1               5                  10                  15

Ser Val Lys Val Ser Cys Lys Ala Ser Gly Gly Thr Phe Asn Ser Tyr
                20                  25                  30

Ala Ile Ser Trp Val Arg Gln Ala Pro Gly Gln Gly Leu Glu Trp Met
            35                  40                  45

Gly Gly Ile Ile Pro Leu Phe Gly Ile Ala His Tyr Ala Gln Lys Phe
        50                  55                  60

Gln Gly Arg Val Thr Ile Thr Ala Asp Glu Ser Thr Asn Thr Ala Tyr
 65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
                100                 105                 110

Trp Gly Gln Gly Thr Thr Val Thr Val Ser Ser
```

<210> SEQ ID NO 86
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Arg Leu Glu Ile Lys
            100                 105

<210> SEQ ID NO 87
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Arg Gly Arg Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Phe Arg Tyr Phe Asp Trp Phe Leu Asp Tyr Trp Gly
            100                 105                 110

Gln Gly Thr Leu Val Thr Val Ser Ser
        115                 120

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 89
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Glu Thr Gly Leu Arg Trp Leu Leu Leu Val Ala Val Leu Lys Gly
1               5                   10                  15

Val Gln Cys Leu Ser Val Glu Glu Ser Gly Gly Arg Leu Val Thr Pro
            20                  25                  30

Gly Thr Pro Leu Thr Leu Thr Cys Thr Ala Ser Gly Phe Thr Ile Thr
        35                  40                  45

Asn Tyr His Met Phe Trp Val Arg Gln Ala Pro Gly Lys Gly Leu Glu
50                  55                  60

Trp Ile Gly Val Ile Thr Ser Ser Gly Ile Gly Ser Ser Ser Thr Thr
65              70                  75                  80

Tyr Tyr Ala Thr Trp Ala Lys Gly Arg Phe Thr Ile Ser Lys Thr Ser
                85                  90                  95

Thr Thr Val Asn Leu Arg Ile Thr Ser Pro Thr Thr Glu Asp Thr Ala
            100                 105                 110

Thr Tyr Phe Cys Ala Arg Asp Tyr Phe Thr Asn Thr Tyr Tyr Ala Leu
        115                 120                 125

Asp Ile Trp Gly Pro Gly Thr Leu Val Thr Val Ser Ser
130                 135                 140

<210> SEQ ID NO 90
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Ser
            20                  25                  30

Thr Ser Thr Ala Val Gly Gly Thr Val Thr Ile Lys Cys Gln Ala Ser
        35                  40                  45
```

```
Gln Ser Ile Ser Val Tyr Leu Ala Trp Tyr Gln Gln Lys Pro Gly Gln
    50                  55                  60

Pro Pro Lys Leu Leu Ile Tyr Ser Ala Ser Thr Leu Ala Ser Gly Val
65                  70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
                100                 105                 110

Ser Ala Gly Ser
        115

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Pro Ser Tyr Val Tyr His Gln Phe
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Pro His Pro Ala Arg Ile Gly Leu
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Pro His Ala Arg Ile Gly Leu
1               5
```

METHODS OF TREATMENT WITH ANTAGONISTS AGAINST PD-1 AND PD-L1 IN COMBINATION WITH RADIATION THERAPY

CROSS-REFERENCE TO RELATED APPLICATION

This application claims benefit under 35 U.S.C. § 119(e) of U.S. Provisional Application No. 62/013,157, filed Jun. 17, 2014, which is incorporated by reference herein in its entirety for all purposes.

SEQUENCE LISTING

The instant application contains a Sequence Listing which has been submitted electronically in ASCII format and is hereby incorporated by reference in its entirety. Said ASCII copy, created on Jun. 16, 2015, is named B7H1-275US1_SL.txt and is 101,340 bytes in size.

FIELD

Methods of treatment for cancer.

BACKGROUND

Radiation therapy (RT) remains the most important non-surgical treatment in the management of solid malignancies with around 50-60% of all cancer patients receiving this treatment. The inclusion of RT in treatment regimens reduces disease recurrence and improves overall survival in the majority of common cancers (1-3). Although effective, many patients suffer from local recurrence and metastatic disease.

In addition to the direct cytoreductive effect of RT, emerging evidence suggests that the generation of anti-tumor immune responses may play an important role in the effectiveness of this treatment (4, 5). RT can lead to expression of ecto-calreticulin on tumor cells as well as the release of several damage-associated molecular patterns (DAMPs) including High Mobility Group Box 1 (HMGB1) and ATP which can lead to recruitment and activation of antigen presenting cells (APCs) and priming of tumor antigen-specific T cell responses (6-10). Despite this immune-escape frequently occurs, with tumor recurrence remaining the leading cause of mortality in patients receiving RT (11). The identification and inhibition of key drivers of immunosuppression may augment anti-tumor immune responses with the potential to improve patient outcome.

New insights into treatment failure and more effective RT combination approaches are therefore urgently required.

The programmed death 1 (PD-1)/programmed death ligand 1 (PD-L1) axis is involved in the maintenance of peripheral tolerance and the modulation of acute inflammatory responses through inhibition of T cell function and through apoptosis of activated T cells (12, 13). In addition to binding PD-1, PD-L1 can also suppress T cell function through interaction with CD80 (14). Expression of PD-L1 is inducible and thought to respond to local inflammatory milieu, particularly type I and II interferon (IFN) (12, 15, 16). Although barely detectable in most normal tissues, expression of PD-L1 has been described in multiple malignancies (reviewed in (17)). Importantly, recent clinical studies with either PD-1 or PD-L1 targeting monoclonal antibodies (mAb) have demonstrated encouraging responses in patients with advanced disease (18-21).

A dosing strategy for combining radiation therapy and a PD-1 and/or PD-L1 antagonist is desired to create maximal benefit for patients suffering from cancer.

SUMMARY

In accordance with the description, a method of treating cancer in a patient comprises
  a. administering at least one dose of radiation therapy; and
  b. administering at least one PD-1 and/or PD-L1 antagonist, wherein at least one PD-1 and/or PD-L1 antagonist is administered on the same day as a dose of radiation therapy or up to and including 4 days later.

In another mode, the at least one PD-1 and/or PD-L1 antagonist is an at least one PD-1 and/or PD-L1 antibody or functional part thereof.

In one aspect, the radiation therapy is fractionated radiation therapy. In one mode, the fractionated radiation therapy comprises from 2 to 7 fractions. In another mode, the fractionated radiation therapy comprises 5 fractions.

In one embodiment, the radiation therapy fractions are administered in sequential days. In another embodiment, the radiation therapy fractions are administered on day 1, day 2, day 3, day 4, and day 5. In one embodiment, the radiation therapy comprises about 10 Gy in 5 fractions.

In one aspect, the at least one PD-1 and/or PD-L1 antagonist is administered on at least day 1 and/or on day 5. In one mode, the at least one PD-1 and/or PD-L1 antagonist is administered multiple times. For example, the at least one PD-1 and/or PD-L1 antagonist may be administered 3 times a week.

In one embodiment, the anti-PD-1 and/or PD-L1 antibody or functional part thereof is MEDI4736.

In another embodiment, the anti-PD-1 and/or anti-PD-L1 antibody or functional part thereof is pembrolizumab, nivolumab, BMS-936558, AMP-224, or MPDL3280A.

In one aspect, the cancer is melanoma, colorectal cancer, or breast cancer. In another aspect, more than one treatment cycle is performed. In a further aspect, from 2-8 treatment cycles are performed. In one mode, treatment cycles are weekly or every other week.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

1D) mAb dosed at 10 mg/kg 3qw for up to 3 weeks. FIG. 1E, tumor volumes 10 days after the start of therapy in 4T1 tumor bearing mice that received 20 Gy RT delivered in 5 daily fractions of 4 Gy either alone or in combination with αPD-L1 mAb. FIG. 1F, 4434 tumor bearing mice received about 10 Gy RT delivered in 5 daily fractions of 2 Gy either alone or in combination with αPD-L1 mAb. Experimental groups contained at least 7 mice and are representative of at least 2 independent experiments. A, E and F show mean±SEM. *, P<0.05 **, P<0.01, Mann-Whitney test. In FIGS. 1C and 1D, *, denotes significance when compared to control mice. +, denotes significance when compared to monotherapy. ***/+++, P<0.001, Log rank (Mantel-Cox) test.

FIG. 2A, tumor volume on day of therapy, 7 and 11 days post combination therapy with 5 fractions of 2 Gy and αPD-L1 mAb. Immune cell subsets (either CD8, CD4 or NK cell) were depleted 1 day prior to therapy with depletion maintained for 2 weeks. ***, P>0.001, *, P>0.01, *, P>0.05, Mann-Whitney test. FIG. 2B, Survival curve. ***/+++, P<0.001, Log-rank (Mantel-Cox) test. Data representative of 10 mice per cohort. FIG. 2C, representative density plots of peripheral blood confirming depletion of immune cell subsets.

FIG. 3A, Survival curve of LTS mice following contralateral rechallenge with 5×10$^5$ CT26 cells. *P<0.05 compared to control mice (log-rank; Mantel-Cox test). FIG. 3B, representative dot blot of IFNγ production by CD8$^+$ T cells isolated from either tumor naïve, or LTS mice originally treated with RT and αPD-L1 mAb. FIG. 3C, frequency of IFNγ$^+$ CD8$^+$ T cells isolated from either tumor naïve, or LTS mice originally treated with RT and αPD-L1 mAb following co-culture with either H2-Ld restricted peptides (AH1 (SPSYVYHQF) (SEQ ID NO: 91); a defined CT26 tumor-associated antigen or β-galactosidase (TPHPARIGL) (SEQ ID NO: 92); control peptide of prokaryotic origin) or 50 Gy irradiated CT26 cells for 5 days, followed by priming with 50 Gy irradiated CT26 cells. *P<0.05 (Mann-Whitney test). Data representative of 2 independent experiments.

FIG. 4A, Expression of PD-L1 on CT26 cells post treatment with RT (2.5-10Gy) in vitro. FIGS. 4B and 4C, Representative contour plots (FIG. 4B) and median fluorescence intensity (FIG. 4C) of PD-L1 expression on CT26 cells (gated as CD45$^−$ cells) isolated from tumors 3 days after receiving about 10 Gy in 5 daily fractions of 2Gy in combination with either CD8, CD4 or NK cell depleting antibodies. *P<0.05 (Mann-Whitney test). Experimental groups contained at least 5 mice and are representative of at least 2 independent experiments.

FIG. 5A, Expression of PD-L1 on wild-type CT26 tumor cells (WT), or cells transduced with either a non-targeting control (NTC) or IFNγR1 ShRNA following co-culture for 24 hours with either 20 ng/ml IFNγ, TNFα or a combination of both cytokines FIG. 5B, representative density plots showing expression of IFNγ and TNFα by CD8$^+$ T cells following treatment with either PBS or phorbol 12-myristate 13-acetate (PMA) and ionomycin, FIG. 5C, Frequency of PD-L1 positive CT26 tumor cells (WT, NTC ShRNA or IFNγR1 ShRNA) following 24 hour co-culture with either PBS or PMA/ionomycin activated splenocytes. n/s=P>0.05, *P<0.001 P<0.01 (2-tailed Student t test). FIGS. 5D and 5E, representative contour plots (FIG. 5D) and median fluorescence intensity (FIG. 5E) of PD-L1 expression on CT26 tumor cells following treatment with RT (about 10 Gy in 5 fractions) in the presence of an αIFNγ blocking mAb (or isotype control) in vivo. **P<0.01, (Mann-Whitney test). Experimental groups contained at least 5 mice.

FIG. 6A, Schema for dose-scheduling studies. Mice received fractionated dose RT (as about 10 Gy in 5 daily fractions of 2 Gy) alone or in combination with αPD-L1 mAb starting either on day 1 of RT cycle (schedule A), day 5 of RT cycle (schedule B) or 7 days post the last dose of RT (Schedule C). FIG. 6B, Survival curves of therapy. ++, P<0.01 compared to monotherapy (log-rank; Mantel-Cox test). FIGS. 6C and 6D, Expression of PD-1 on CD4$^+$ (FIG. 6C) and CD8$^+$ (FIG. 6D) T cells 24 hours and 7 days after the last dose of RT. *P<0.05 (Mann-Whitney test). Experimental groups contained at least 5 mice and are representative of at least 2 independent experiments.

FIG. 10A) tumour volumes following fractionated dose RT (as 10 Gy in 5 daily fractions of 2 Gy) alone or in combination with αPD-L1 mAb starting either on day 1 of RT cycle (schedule A), day 5 of RT cycle (schedule B) or 7 days post the last dose of RT (Schedule C). FIGS. 10B and 10C) tumour volumes of RT-treated mice demonstrating equivalent tumour volumes across different dosing schedules. n/s, P>0.05 (Mann-Whitney test). Experimental groups contained at least 5 mice and are representative of at 2 independent experiments.

DESCRIPTION OF THE SEQUENCES

Figure 1A:
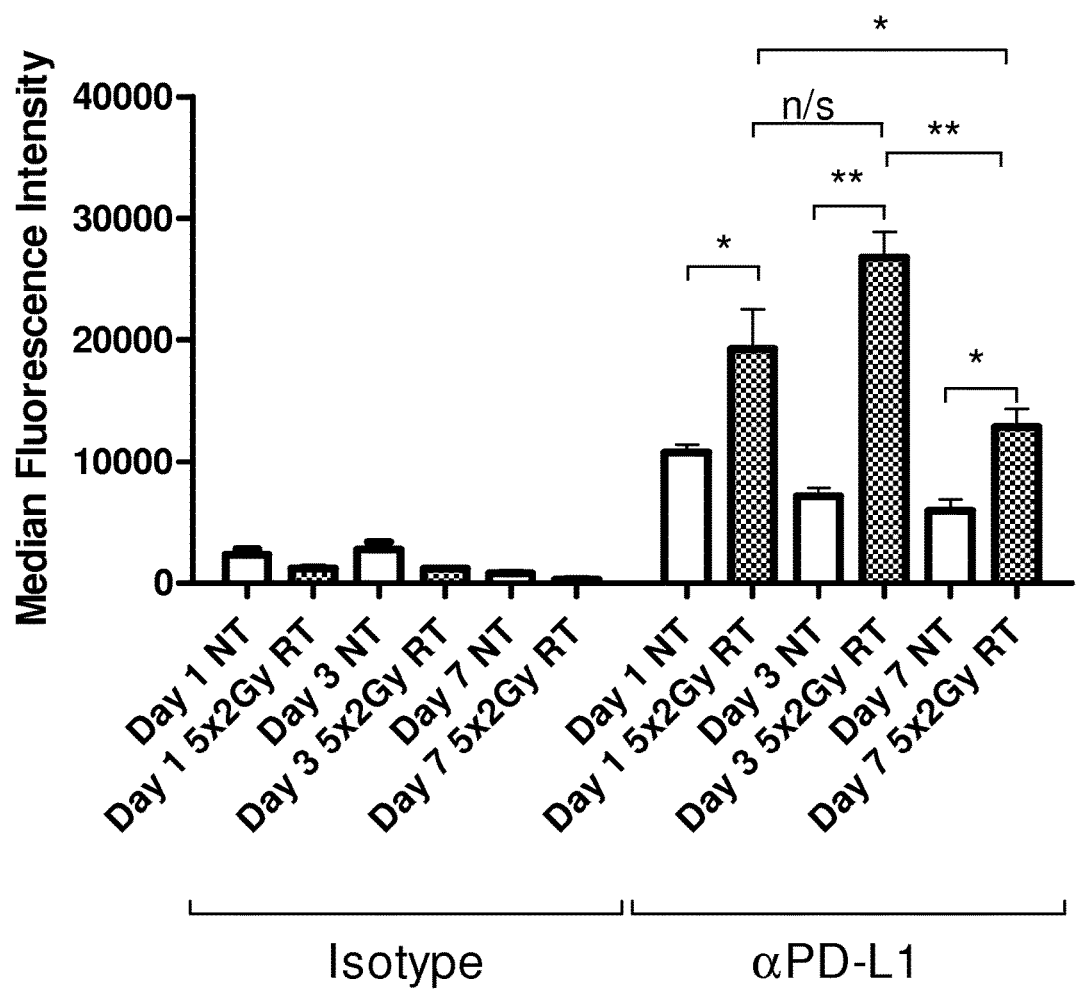
FIGS. 1A-1F illustrate that blockade of the PD-1/PD-L1 axis potentiates the activity of fractionated radiation therapy. A and B, median fluorescence intensity (FIG. 1A) and representative histograms (FIG. 1B) of PD-L1 expression on CT26 cells isolated from tumors 1, 3 or 7 days after treatment with about 10 Gy in 5 daily fractions of 2 Gy. C and D, CT26 tumor bearing mice received about 10 Gy RT delivered in 5 daily fractions of 2 Gy either alone or in combination with either αPD-1 (FIG. 1C) or αPD-L1 (FIG.
Figure 1B:
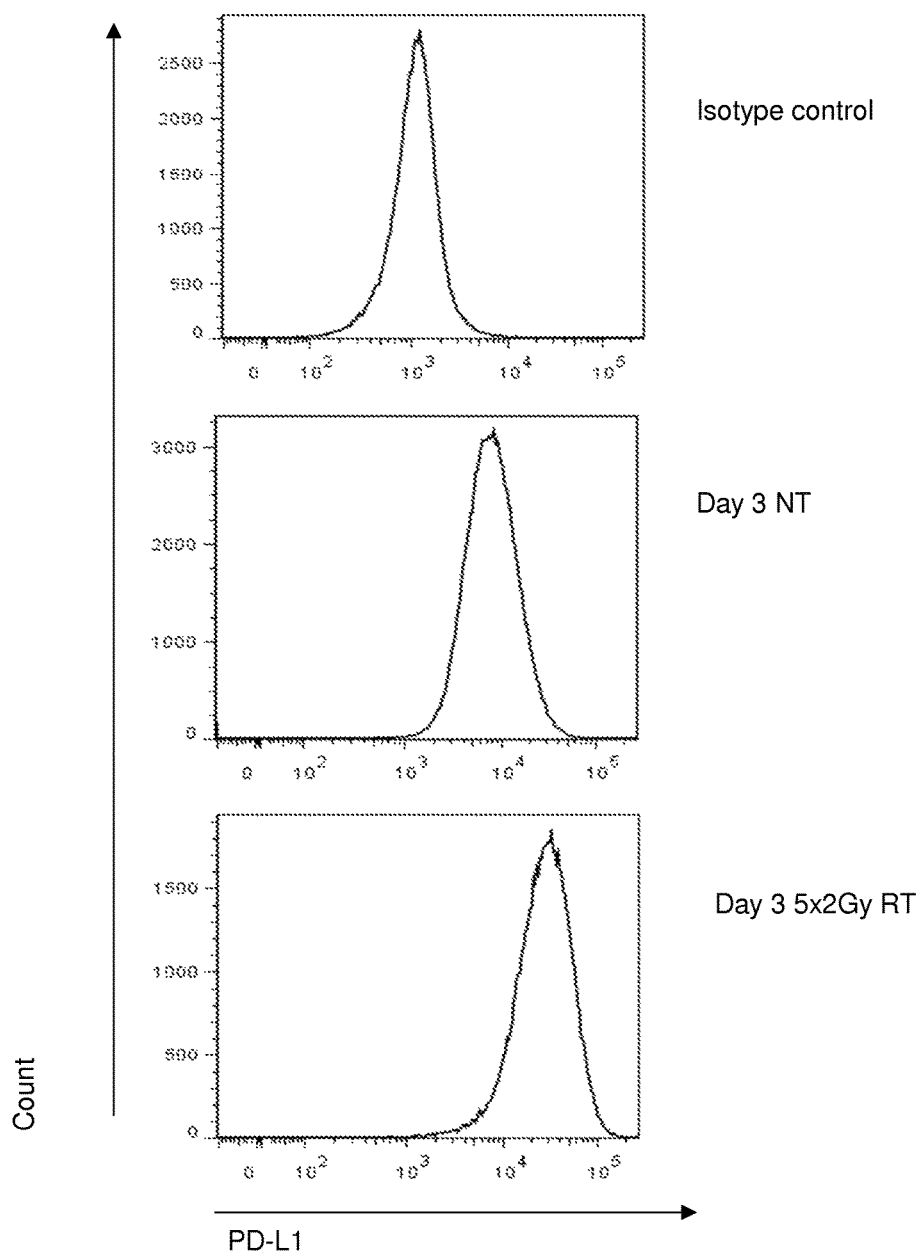

Table 1 provides a listing of certain sequences referenced in present embodiments. CDRs have been indicated in bold and underlining.

TABLE 1

| Description | Sequence | SEQ ID NO |
|---|---|---|
| 2.7A4 VH | EVQLVESGGGLVKPGGSLRLS CAASGFTFSTYSMNWVRQAPG KGLEWVSSISSSGDYIYYADS VKGRFTISRDNAKNSLFLQMN SLKAEDTAVYYCARDLVTSMV AFDYWGQGTLVTVSS | 1 |
| 2.7A4 VL | TCSGDALPQKYVFWYQQKSGQ APVLVIYEDSKRPSGIPERFS GSSSGTMATLTISGAQVEDEA DYYCYSTDRSGNHRVFGGGTR LTVL | 2 |
| 2.9D10 VH | EVQLVESGGGLVQPGGSLRLS CAASGFTFSSYWMSWVRQAPG KGLEWVANIKQDGGEQYYVDS VKGRFTISRDNAKNSLYLQMN SLRAEDTAVYYCARDWNYGYY DMDVWGQGTTVTVSS | 3 |
| 2.9D10 VL | EIVLTQSPGTLSLSPGERATL SCRASQSVSSNYLAWFQQKPG QAPRLLIFGTSSRATGIPDRF SGSGSGTDFTLTISRLEPEDF AVYYCQQYGSSIFTFGPGTKV DIK | 4 |
| 2.14H9 VH | EVQLVESGGGLVQPGGSLRLS CAASGFTFSRYWMSWVRQAPG KGLEWVANIKQDGSEKYYVDS VKGRFTISRDNAKNSLYLQMN SLRAEDTAVYYCAREGGWFGE LAFDYWGQGTLVTVSS | 5 |
| 2.14H9 VL | EIVLTQSPGTLSLSPGERATL SCRASQRVSSSYLAWYQQKPG QAPRLLIYDASSRATGIPDRF SGSGSGTDFTLTISRLEPEDF AVYYCQQYGSLPWTFGQGTEV EIK | 6 |
| 2.20A8 VH | EVQLLESGGGLVQPGGSLRLS CAASGFTFSNYAMSWVRQAPG KGLEWVSAIRGSGGSTYYADS VKGRFTISRDNSKNTLYLQMN SLRAEDTAVYYCAKDLHYDSS GYLDYWGQGTLVTVSS | 7 |
| 2.20A8 VL | DIQMTQSPSSVSASVGDRVTI TCRASQGIRSWLAWYQQKPGK APKLLIYAISRLQSGVPSRFS GSGSGTDFTLTISSLQPEDFA TYYCQQANSFPLTFGGGTKVE IK | 8 |
| 3.15G8 VH | EVQLVESGGGLVQPGGSLRLS CAASGFTFSSYWMSWVRQAPG KGLEWVANIKQDGGEKYYVDS VKGRFTISRDNAKNSLFLQMN SLRAEDTAVYYCARVQLYSDY FDYWGQGTLVTVSS | 9 |
| 3.15G8 VL | DIQMTQSPSSVSASVGDRVTI TCRASQGISSWLAWYQQKSGK APKLLIYAASGLQSGVPSRFS GSGSGTDFTLTISSLQPEDLA TYYCQQSHSLPPTFGQGTKVE IK | 10 |
| 3.18G1 VH | EVQLLESGGDLVQPGGSLRLS CAASGFTFNSYAMSWVRQAPG KGLEWVSTISGSGGFTFSADS VKGRFTISRDNSKNTLFLQMN SLRVEDSAVYSCAKVLVGFNN GCWDYWGQGTLVTVSS | 11 |
| 3.18G1 VL | SYVLTQPPSVSVAPGQTARIT CGGNNIGSKSVHWYQQKPGQA PVLVVYDDSDRPSGIPERFSG SNSGNTATLTISRVEAGDEAD YYCQVWDSSNDHVVFGGGTKL TVL | 12 |
| 2.7A4 OPT VH | EVQLVESGGGLVKPGGSLRLS CAASGFTFSTYSMNWVRQAPG KGLEWVSSISSSGDYIYYADS VKGRFTISRDNAKNSLYLQMN SLRAEDTAVYYCARDLVTSMV AFDYWGQGTLVTVSS | 13 |
| 2.7A4 OPT VL | SYELTQPPSVSVSPGQTARIT CSGDALPQKYVFWYQQKSGQA PVLVIYEDSKRPSGIPERFSG SSSSGTMATLTISGAQVEDEAD YYCYSTDRSGNHRVFGGGTKL TVL | 14 |
| 2.14H9 OPT VH | EVQLVESGGGLVQPGGSLRLS CAASGFTFSRYWMSWVRQAPG KGLEWVANIKQDGSEKYYVDS VKGRFTISRDNAKNSLYLQMN SLRAEDTAVYYCAREGGWFGE LAFDYWGQGTLVTVSS | 15 |
| 2.14H9 OPT VL | EIVLTQSPGTLSLSPGERATL SCRASQRVSSSYLAWYQQKPG QAPRLLIYDASSRATGIPDRF SGSGSGTDFTLTISRLEPEDF AVYYCQQYGSLPWTFGQGTKV EIK | 16 |
| 1E12 VH (anti-PD-L1) | EVKLQESGPS LVKPSQTLSL TCSVTGYSIT SDYWNWIRKF PGNKLEYVGY ISYTGSTYYN PSLKSRISIT RDTSKNQYYL QLNSVTSEDT ATYYCARYGG WLSPFDYWGQ GTTLTVSS | 17 |
| 1E12 VL (anti-PD-L1) | DIVMTQSHKL MSTSVGDRVS ITCKASQDVG TAVAWYQQKP GQSPKLLIYW ASTRHTGVPD RFTGSGSGTD FTLTISNVQS EDLADYFCQQ DSSYPLTFGA GTKVELK | 18 |
| 1F4 VH (anti-PD-L1) | EVQLQESGPG LVAPSQSLSI TCTVSGFSLT TYSINWIRQP PGKGLEWLGV MWAGGGTNSN SVLKSRLIIS KDNSKSQVFL KMNSLQTDDT ARYYCARYYG NSPYYAIDYW GQGTSVTVSS | 19 |
| 1F4 VL (anti-PD-L1) | DIVTTQSHKL MSTSVGDRVS ITCKASQDVG TAVAWYQQKP GQSPKLLIYW ASTRHTGVPD RFTGSGSGTD FTLTISNVQS EDLADYFCQQ DSSYPLTFGA GTKVELK | 20 |
| 2G11 VH (anti-PD-L1) | EVKLQESGPS LVKPSQTLSL TCSVTGYSII SDYWNWIRKF PGNKLEYLGY ISYTGSTYYN PSLKSRISIT RDTSKNQYYL QLNSVTTEDT ATYYCARRGG WLLPFDYWGQ GTTLTVSS | 21 |

TABLE 1-continued

| Name | Sequence | SEQ ID NO |
|---|---|---|
| 2G11 VL (anti-PD-L1) | DIVMTQSPSS LAVSVGEKVS MGCKSSQSLL YSSNQKNSLA WYQQKPGQSP KLLIDWASTR ESGVPDRFTG SGSGTDFTLT ISSVKAEDLA VYYCQQYYGY PLTFGAGTKL ELK | 22 |
| 3B6 VH (anti-PD-L1) | EVKLQESGPS LVKPGASVKL SCKASGYTFT SYDINWVKQR PGQGLEWIGW IFPRDNNTKY NENFKGKATL TVDTSSTTAY MELHSLTSED SAVYFCTKEN WVGDFDYWGQ GTTLTLSS | 23 |
| 3B6 VL (anti-PD-L1) | DIVMTQSPAI MSASPGEKVT MTCSASSSIR YMHWYQQKPG TSPKRWISDT SKLTSGVPAR FSGSGSGTSY ALTISSMEAE DAATYYCHQR SSYPWTFGGG TKLEIK | 24 |
| 3D10 VH (anti-PD-L1) | EVQLQQSGPD LVTPGASVRI SCQASGYTFP DYYMNWVKQS HGKSLEWIGD IDPNYGGTTY NQKFKGKAIL TVDRSSSTAY MELRSLTSED SAVYYCARGA LTDWGQGTSL TVSS | 25 |
| 3D10 VL (anti-PD-L1) | QIVLSQSPAI LSASPGEKVT MTCRASSSVS YIYWFQQKPG SSPKPWIYAT FNLASGVPAR FSGSGSGTSY SLTISRVETE DAATYYCQQW SNNPLTFGAG TKLELK | 26 |
| 1E3 VH (anti-PD-1) | EVQLQQSGPV LVKPGASVKM SCKASGYTFT DYYMNWVKQS HGKSLEWIGN INPYNGGTTY NQKFKGKATL TVDKSSRTAY MEINSLTSED SAVYYCARGR IYDGSLDYWG QGTALTVSS | 27 |
| 1E3 VL (anti-PD-1) | DIQMTQFPSS LCASQGGKVT VTCKASQDIN NYMAWYQHKP GKGPRLLIHY TSTLLSGIPS RFSGSGSGRD YSFSISNLEP EDIATYYCLQ YDNLWTFGGG TKLEIK | 28 |
| 1E8 VH (anti-PD-1) | QVQLQQSGAE LAKPGASVRL SCKASGYTFT NYWMHWVKQR PGQGLEWIGH INPSSGFTTY NQNFKDKATL TADKSSNTAY MQLSSLTYED SAVYFCARED YDVDYWGQGT TLTVSS | 29 |
| 1E8 VL (anti-PD-1) | DIVMTQSQKF MSTSVGDRVS VTCKASQSVD TNVAWYQQKP GQSPKALIFS ASYRYSGVPD RFTGSGSGTD FLTTINSVQS EDLAEYFCQQ YNSYPYTFGS GTKLEIK | 30 |
| 1H3 VH (anti-PD-1) | EVQLVESGGG LVKPGGSLKL SCAASGFTFS DYGMHWVRQA PEKGLEWVAY ISSGSYTIYY TDTVKGRFTI SRDNAKNTLF LQMTSLRSED TAMYYCARRG YGSFYEYYFD YWGQGTTLTV SS | 31 |
| 1H3 VL (anti-PD-1) | QIVLTQSPAL MSASPGEKVT MTCSASSSVS YMYWYQQKPR SSPKPWIYLT SNLASGVPAR FSGSGSGTSY SLTISSMEAE DAATYYCQQW SSNPFTFGSG TKLEIK | 32 |
| Humanized Anti-Human B7-H1 Heavy Chain HC1_1 | QVQLVQSGAE VKKPGASVKV SCKASGYTFPDYYMNWVRQAPG QGLEWMGDIDPNYGGTNYAQK FQGRVTMTRDTSISTAYMELS RLRSDDTAVYYCARGALTDWG QGTMVTVSS | 33 |
| Humanized Anti-Human B7-H1 Heavy Chain HC1_2 | QVQLVQSGAEVKKPGASVKVS CKASGYTFPDYYMNWVRQAPG QSLEWMGDIDPNYGGTNYNQK FQGRVTMTRDTSISTAYMELS RLRSDDTAVYYCARGALTDWG QGTMVTVSS | 34 |
| Humanized Anti-Human B7-H1 Heavy Chain HC1_3 | EVQLVQSGAEVKKPGASVKVS CKASGYTFPDYYMNWVRQAPG QSLEWMGDIDPNYGGTNYNQK FQGRVTMTVDRSSTAYMELS RLRSDDTAVYYCARGALTDWG QGTMVTVSS | 35 |
| Humanized Anti-Human B7-H1 Heavy Chain HC2_1 | EVQLVESGGGLVQPGRSLRLS CTASGYTFPDYYMNWVRQAPG KGLEWVGDIDPNYGGTTYAAS VKGRFTISVDRSKSIAYLQMS SLKTEDTAVYYCTRGALTDWG QGTMVTVSS | 36 |
| Humanized Anti-Human B7-H1 Heavy Chain HC2_2 | EVQLVESGGGLVQPGRSLRLS CTASGYTFPDYYMNWVRQAPG KGLEWVGDIDPNYGGTTYNAS VKGRFTISVDRSKSIAYLQMS SLKTEDTAVYYCARGALTDWG QGTMVTVSS | 37 |
| Humanized Anti-Human B7-H1 Heavy Chain HC2_3 | EVQLVESGGGLVQPGRSLRLS CTASGYTFPDYYMNWVRQAPG KGLEWVGDIDPNYGGTTYNQS VKGRFTISVDRSKSIAYLQMS SLKTEDTAVYYCARGALTDWG QGTMVTVSS | 38 |
| Humanized Anti-Human B7-H1 Light Chain LC1_1 | EIVLTQSPATLSLSPGERATL SCRASSSVSYIYWFQQKPGQA PRLLIYAAFNRATGIPARFSG SGSGTDYTLTISSLEPEDFAV YYCQQWSNNPLTFGQGTKVEI K | 39 |
| Humanized Anti-Human B7-H1 Light Chain LC1_2 | EIVLTQSPATLSLSPGERATL SCRASSSVSYIYWFQQKPGQS PRPLIYAAFNRATGIPARFSG SGSGTDYTLTISSLEPEDFAV YYCQQWSNNPLTFGQGTKVEI K | 40 |
| Humanized Anti-Human B7-H1 Light Chain LC1_3 | QIVLTQSPATLSLSPGERATL SCRASSSVSYIYWFQQKPGQS PRPLIYATFNLASGIPARFSG SGSGTSYTLTISRLEPEDFAV YYCQQWSNNPLTFGQGTKVEI K | 41 |
| Humanized Anti-Human B7-H1 Light Chain LC2_1 | DIQLTQSPSSLSASVGDRVTI TCRASSGVSYIYWFQQKPGKA PKLLIYAAFNLASGVPSRFSG SGSGTEYTLTISSLQPEDFAT YYCQQWSNNPLTFGQGTKVEI K | 42 |
| Humanized Anti-Human B7-H1 Light Chain LC2_2 | DIQLTQSPSSLSASVGDRVTI TCRASSGVSYIYWFQQKPGKA PKPLIYAAFNLASGVPSRFSG SGSGTEYTLTISSLQPEDFAT YYCQQWSNNPLTFGQGTKVEI K | 43 |
| Humanized Anti-Human B7-H1 Light Chain LC2_3 | DIQLTQSPSILSASVGDRVTI TCRASSSVSYIYWFQQKPGKA PKPLIYATFNLASGVPSRFSG SGSGTSYTLTISSLQPEDFAT | 44 |

TABLE 1-continued

| Description | Sequence | SEQ ID NO |
|---|---|---|
| | YYCQQWSNNPLTFGQGTKVEIK | |
| Humanized Anti-Human PD-1 Heavy Chain HC1_1 | EVQLVESGGGLVQPGGSLRLSCAASGFTFSDYGMHWVRQAPGKGLEWVSYISSGSSTIYYADSVKGRFTISRDNAKNTLYLQMSSLRAEDTAVYYCARRGYGSFYEYYFDYWGQGTTVTSS | 45 |
| Humanized Anti-Human PD-1 Heavy Chain HC1_2 | EVQLVESGGGLVQPGGSLRLSCAASGFTFSDYGMHWVRQAPGKGLEWVAYISSGSYTIYYADSVKGRFTISRDNAKNTLYLQMSSLRAEDTAVYYCARRGYGSFYEYYFDYWGQGTTVTSS | 46 |
| Humanized Anti-Human PD-1 Heavy HC1_3 | EVQLVESGGGLVQPGGSLRLSCAASGFTFSDYGMHWVRQAPGKGLEWVAYISSGSYTIYSADSVKGRFTISRDNAKNTLYLQMSSLRAEDTAVYYCARRGYGSFYEYYFDYWGQGTTLTVSS* | 47 |
| Humanized Anti-Human PD-1 Heavy HC2_1 | QVQLVQSGAEVKKPGASVKVSCKASGFTFSDYGMHWVRQAPGQRLEWMGYISSGSSTIYYSQKFQGRVTITRDNSASTLYMELSSLRSEDTAVYYCARRGYGSFYEYYFDYWGQGTTLTVSS | 48 |
| Humanized Anti-Human PD-1 Heavy HC2_2 | EVQLVQSGAEVKKPGASVKVSCAASGFTFSDYGMHWVRQAPGQRLEWMGYISSGSYTIYYSQKFQGRVTITRDNSASTLYMELSSLRSEDTAVYYCARRGYGSFYEYYFDYWGQGTTLTVSS | 49 |
| Humanized Anti-Human PD-1 Heavy HC2_3 | EVQLVQSGAEVKKPGASVKVSCAASGFTFSDYGMHWVRQAPGQRLEWVAYISSGSYTIYYSQKFQGRVTITRDNSASTLYMELSSLRSEDTAVYYCARRGYGSFYEYYFDYWGQGTTLTVSS | 50 |
| Humanized Anti-Human PD-1 Light LC1_1 | EIVLTQSPATLSLSPGERATLSCRASSSVSYMYWYQQKPGQAPRLLIYLASNRATGIPARFSGSGSGTDYTLTISSLEPEDFAVYYCQQWSSNPFTFGQGTKLEIK | 51 |
| Humanized Anti-Human PD-1 Light LC1_2 | QIVLTQSPATLSLSPGERATLSCSASSSVSYMYWYQQKPGQAPRLLIYLTSNRATGIPARFSGSGSGTDYTLTISSLEPEDFAVYYCQQWSSNPFTFGQGTKLEIK | 52 |
| Humanized Anti-Human PD-1 Light LC2_1 | DIQLTQSPSSLSASVGDRVTITCRASSSVSYMYWYQQKPGKAPKLLIYLASNLASGVPSRFSGSGSGTEYTLTISSLEPEDFATYYCQQWSSNPFTFGQGTKLEIK | 53 |
| Humanized Anti-Human PD-1 Light LC2_2 | QIQLTQSPSSLSASVGDRVTITCSASSSVSYMYWYQQKPGKAPKLLIYLTSNLASGVPSRFSGSGSGTEYTLTISSLEPEDFATYYCQQWSSNPFTFGQGTKLEIK | 54 |

| Certain Specific Combinations | Antibody | Light Chain | Heavy Chain |
|---|---|---|---|
| | h1H3 Var 1 | LC1_1 | HC1_1 |
| | h1H3 Var 2 | LC1_1 | HC1_2 |
| | h1H3 Var 3 | LC1_1 | HC1_3 |
| | h1H3 Var 4 | LC1_2 | HC1_1 |
| | h1H3 Var 5 | LC1_2 | HC1_2 |
| | h1H3 Var 6 | LC1_2 | HC1_3 |
| | h1H3 Var 7 | LC2_1 | HC2_1 |
| | h1H3 Var 8 | LC2_1 | HC2_2 |
| | h1H3 Var 9 | LC2_1 | HC2_3 |
| | h1H3 Var 10 | LC2_2 | HC2_1 |
| | h1H3 Var 11 | LC2_2 | HC2_2 |
| | h1H3 Var 12 | LC2_2 | HC2_2 |
| | h1H3 Var 13 | LC1_1 | HC1_1 |
| | h1H3 Var 14 | LC2_1 | HC2_1 |

| Description | Sequence | SEQ ID NO |
|---|---|---|
| 17D8 VH (#1) | QVQLVESGGDVVQPGGSLRLSCAASGVAFSNYGMHWVRQAPGKGLEWVAVIWYDGSNKYYADSVKGRFTISRDNSKNMLYLQMNSLRAEDTAMYYCARNDDYWGQGTLVTVSS | 55 |
| 17D8 VL (#8) | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGGGTKVEIK | 56 |
| 2D3 VH (#2) | QVQLVESGGDVVQPGRSLRLSCAASGLTFTNYGFHWVRQAPGKGLEWVAVIWYDGSKKYYADSVKGRFTISRDNSKNTLYLQMNNLRAEDTAVYYCATGDDYWGQGTLVTVSS | 57 |
| 2D3 VL (#9) | EIVLTQSPATLSLSPGERATLSCRASQSVSSYLAWYQQKPGQAPRLLIYDTSNRATGIPARFSGSGSGTDFTLTISSLEPEDFAVYYCQQRSNWPLTFGGGTKVEIK | 58 |
| 4H1 VH 3 | QVYLVESGGGVVQPGRSLRLSCAASGFTFSNYGMHWVRQAPGKGLEWVALIWYDGSNKYYADSVKGRFTISRDNSKNTLYLQMTSLRVEDTAVYYCASNVDHWGQGTLVTVSS | 59 |
| 4H1 Vl 10 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK | 60 |
| 5C4 VH 4 BMS-936558 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS | 61 |
| 5C4 VL 11 BMS-936558 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK | 62 |
| 4A11 VH 5 | QLQLQESGPGLVKPSETLSLTCTVSGGSLSRSSFFWGWIRQPPGKGLEWIGSIYYSGSTYYNPSLKSRVTISVDTSKNQFSLKLSSVTAADTAVYYCVRDYDILTGDEDYWGQGTLVTVSS | 63 |
| 4A11 VL 12 | DIQMTQSPSSLSASVGDRVSITCRASQGISSWLAWYQQKPEK | 64 |

TABLE 1-continued

| | | |
|---|---|---|
| | APKSLIYAASNLRSGVPSRFSGSGSGTDFTLTISSLQPEDFATYYCQQYYSPRTFGQGTKVEIK | 5 |
| 7D3 VH 6 | QVQLVESGGGVVQPGRSLRLSCTTSGITFSSYGFHWVRQAPGKGLEWVAVIWYDGSKKYYADSVKGRFTLSRDDSKNTLYLQMNSLRAEDTAVYYCVTGDDYWGQGTLVTVSS | 65 |
| 7D3 VL 13 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGGGTKVEIK | 66 |
| 5F4 VH 7 | QLQLQESGPGLVKPSETLSLTCSVSGGSLSRSSYFWGWIRQPPGKGLEWIASIFYSGETYFNPSLKSRVTISVDTSRNQFSLKLSSVTAADTAVYYCARDYDILTGDEDYWGQGTLVTVSS | 67 |
| 5F4 VL 14 | DIQMTQSPSSLSASVGDRVTITCRASQGISSWLAWYQQKPEKAPKSLIYAASSLQSGVPSRFSGSGSGTDFTLTISSLQPEDFATYYCQQYYSPRTFGQGTKVEIK | 68 |
| 3G10 VH 15 | QVQLVQSGAEVKKPGASVKVSCKASGYTFTDYGFSWVRQAPGQGLEWMGWITAYNGNTNYAQKLQGRVTMTTDTSTSTVYMELRSLRSDDTAVYYCARDYFYGMDVWGQGTTVTVSS | 69 |
| 3G10 VL 25 | EIVLTQSPATLSLSPGERATLSCRASQSVSSYLVWYQQKPGQAPRLLIYDASNRATGIPARFSGSGSGTDFTLTISSLEPEDFAVYYCQQRSNWPRTFGQGTKVEIK | 70 |
| 12A4 VH 16 BMS-936559 | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 71 |
| 12A4 VL 26 BMS-93655 | EIVLTQSPATLSLSPGERATLSCRASQSVSSYLAWYQQKPGQAPRLLIYDASNRATGIPARFSGSGSGTDFTLTISSLEPEDFAVYY | 72 |
| 10A5 VH 17 | QVQLVQSGAEVKKPGASVKVSCKASGYTFTSYDVHWVRQAPGQRLEWMGWLHADTGITKFSQKFQGRVTITRDTSASTAYMELSSLRSEDTAVYYCARERIQLWFDYWGQGTLVTVSS | 73 |
| 10A5 VL 27 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPYTFGQGTKLEIK | 74 |
| 5F8 VH 18 | QVQLVQSGAEVKKPGSSVKVSCKVSGGIFSTYAINWVRQAPGQGLEWMGGIIPIFGTANHAQKFQGRVTITADESTSTAYMELSSLRSEDTAVYYCARDQGIAAALFDYWGQGTLVTVSS | 75 |
| 5F8 28 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 76 |
| 10H10 VH 19 | EVQLVESGGGLVQPGRSLRLSCAVSGFTFDDYVVHWVRQAPGKGLEWVSGISGNSGNIGYADSVKGRFTISRDNAKNSLYLQMNSLRAEDTALYYCAVPFDYWGQGTLVTVSS | 77 |
| 10H10 29 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPYTFGQGTKLEIK | 78 |
| 1B12 VH 20 | QVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSS | 79 |
| 1B12 30 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 80 |
| 7H1 VH 21 | QVQLVQSGAEVKKPGSSVKVSCKTSGGTFSSYAISWVRQAPGQGLEWMGGIIPIFGKAHYAQKFQGRVTITADESTTAYMELSSLRSEDTAVYYCARKYDYVSGSPFGMDVWGQGTTVTVSS | 81 |
| 7H1 31 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK* | 82 |
| 11E6 VH 22 | QVQLVQSGAEVKKPGSSVKVSCKASGGTFSSYAINWVRQAPGQGLEWMGGIIPIFGSANYAQKFQDRVTITADESTSAAYMELSSLRSEDTAVYYCARDSSGWSRYYMDVWGQGTTVTVSS | 83 |
| 11E6 32 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPFGGGTKVEIK* | 84 |
| 12B7 VH 23 | QVQLVQSGAEVKEPGSSVKVSCKASGGTFNSYAISWVRQAPGQGLEWMGGIIPLFGIAHYAQKFQGRVTITADESTNTAYMDLSSLRSEDTAVYYCARKYSVSGSPFGMDVWGQGTTVTVSS | 85 |
| 12B7 33 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTRLEIK | 86 |
| 13G4 VH 24 | EVQLVESGGGLVQPGRSLRLSCAASGITFDDYGMHWVRQAPG | 87 |

TABLE 1-continued

| | | |
|---|---|---|
| | KGLEWVSGISWNRGRIEYADS VKGRFTISRDNAKNSLYLQMN SLRAEDTALYYCAKGRFRYFD WFLDYWGQGTLVTVSS | |
| 13G4 34 | AIQLTQSPSSLSASVGDRVTI TCRASQGISSALAWYQQKPGK APKLLIYDASSLESGVPSRFS GSGSGTDFTLTISSLQPEDFA TYYCQQFNSYPFTFGPGTKVD IK | 88 |
| 28-8 VH 35 | METGLRWLLLVAVLKGVQCLS VEESGGRLVTPGTPLTLTCTA SGFTITNYHMFWVRQAPGKGL EWIGVITSSGIGSSTTYYAT WAKGRFTISKTSTTVNLRITS PTTEDTATYFCARDYFTNTYY ALDIWGPGTLVTVSS | 89 |
| 28-8 VL 36 | MDTRAPTQLLGLLLLWLPGAR CALVMTQTPSSTSTAVGGTVT IKCQASQSISVYLAWYQQKPG QPPKLLIYSASTLASGVPSRF KGSRSGTEYTLTISGVQREDA ATYYCLGSAGS | 90 |

DESCRIPTION OF THE EMBODIMENTS

I. Methods of Treatment

The present methods encompass treatment of cancer employing at least one dose or radiation therapy and at least one dose of at least one PD-1 and/or PD-L1 antagonist. For instance, a method of treating cancer in a patient may include administering at least one dose of radiation therapy and administering at least one PD-1 and/or PD-L1 antagonist, wherein the at least one PD-1 and/or PD-L1 antagonist is administered on the same day as a dose of radiation therapy or up to and including 4 days later.

The method of treating cancer may be administered once (as a single treatment cycle) or it may be administered more than once (i.e., with multiple treatment cycles), such as on a weekly, every other week, every three weeks, or every month cycle. If the method is administered more than once, it may be administered 2, 3, 4, 5, 6, 7, or 8 times, or more.

While not being bound by theory, in a range of established syngeneic tumor models we found that low doses of fractionated RT led to upregulation of tumor cell expression of PD-L1 in vivo. We show that fractionated RT delivered in combination with αPD-1 or αPD-L1 mAbs generated effective anti-tumor CD8$^+$ responses, which improved local tumor control and long-term survival, and protected against tumor rechallenge by the induction of a tumor antigen-specific memory immune response. CD8$^+$ T cell production of IFNγ was found to be responsible for the upregulation of PD-L1 on tumor cells following fractionated RT. Furthermore, scheduling of anti-PD-L1 mAb relative to the delivery of fractionated RT appeared to affect therapeutic outcome; with administration of the antagonist on the same day as RT or up to and including 4 days after the first dose of fractionated RT showing benefit over administration of the antagonist more than 7 days after the conclusion of radiation therapy. And, while not being bound by theory, upregulation of tumor cell PD-L1 expression in response to low doses of fractionated RT, as used routinely in the clinic, appears to be a mechanism of adaptive immunological resistance by tumor cells; with the PD-L1/PD-1 signalling axis therefore potentially contributing to RT treatment failure. Combination therapy with RT and blockade of the PD-1/PD-L1 signalling axis has the potential to overcome this resistance but, based on our preclinical studies, dosage timing impacts the treatment results, providing important new insights for translation to the clinic.

A. PD-1 and/or PD-L1 Antagonists for Use in Methods of Treatment

In one embodiment, the at least one PD-1 and/or PD-L1 antagonist for use the present methods is an anti-PD-1 and/or anti-PD-L1 antibody or functional part thereof.

In one aspect, the at least one PD-1 and/or PD-L1 antagonist is administered on the same day as a dose of radiation therapy or up to and including 4 days later. For example, in one aspect, if radiation therapy is provided on day 1 of a treatment cycle, the at least one PD-1 and/or PD-L1 antagonist may also be administered on day 1 of the treatment cycle (i.e., the same day as a dose of radiation therapy). In another aspect, if radiation therapy is provided on day 1 of a treatment cycle, the at least one PD-1 and/or PD-L1 antagonist is administered on day 5 (i.e., 4 days later). In a further aspect, the PD-1 and/or PD-L1 antagonist may be administered on day 1, day 2, day 3, day 4, day 5, day 6, and/or day 7 of a treatment cycle (including both single and multiple treatment schedules).

In one embodiment, the at least one PD-1 and/or PD-L1 antagonist is administered multiple times in a treatment cycle. In another embodiment, the at least one PD-1 and/or PD-L1 antagonist is administered 2, 3, 4, 5 or more times in a treatment cycle. For example, the antagonist may be administered three times a week for a one-week treatment cycle, or three times a week for a treatment cycle with two or more weeks as described above.

In one aspect, the antibody or functional part thereof is chosen from those disclosed in US Publication 2010/0028330, which is incorporated by reference for the teaching of these antibodies and functional parts thereof. In one embodiment, the antibody if MEDI4736.

In another embodiment, the anti-PD-1 and/or anti-PD-L1 antibody is pembrolizumab, nivolumab, BMS-936558, AMP-224, or MPDL3280A.

The antibodies or functional parts thereof are administered in therapeutically effective amounts. Generally, a therapeutically effective amount may vary with the subject's age, condition, and sex, as well as the severity of the medical condition of the subject. A therapeutically effective amount of an antibody or functional part thereof ranges from about 0.001 to about 30 mg/kg body weight, from about 0.01 to about 25 mg/kg body weight, from about 0.1 to about 20 mg/kg body weight, or from about 1 to about 10 mg/kg. The dosage may be adjusted, as necessary, to suit observed effects of the treatment. The appropriate dose is chosen based on clinical indications by a treating physician.

The antibodies may be given as a bolus dose, to maximize the circulating levels of antibodies for the greatest length of time after the dose. Continuous infusion may also be used after the bolus dose.

As used herein, the term antibody or functional part thereof is used in the broadest sense. It may be man-made such as monoclonal antibodies (mAbs) produced by conventional hybridoma technology, recombinant technology and/or a functional fragment thereof. It may include both intact immunoglobulin molecules for example a polyclonal antibody, a monoclonal antibody (mAb), a monospecific antibody, a bispecific antibody, a polyspecific antibody, a human antibody, a humanized antibody, an animal antibody (e.g. camelid antibody), chimeric antibodies, as well as portions, fragments, regions, peptides and derivatives thereof (provided by any known technique, such as, but not limited to, enzymatic cleavage, peptide synthesis, or recombinant techniques), such as, for example, immunoglobulin devoid of light chains, Fab, Fab', F(ab')$_2$, Fv, scFv, antibody fragment, diabody, Fd, CDR regions, or any portion or peptide sequence of the antibody that is capable of binding antigen or epitope. In one embodiment, the functional part is a single chain antibody, a single chain variable fragment (scFv), a Fab fragment, or a F(ab')$_2$ fragment.

An antibody or functional part is said to be "capable of binding" a molecule if it is capable of specifically reacting with the molecule to thereby bind the molecule to the antibody. Antibody fragments or portions may lack the Fc fragment of intact antibody, clear more rapidly from the circulation, and may have less non-specific tissue binding than an intact antibody. Examples of antibody may be produced from intact antibodies using methods well known in the art, for example by proteolytic cleavage with enzymes such as papain (to produce Fab fragments) or pepsin (to produce F(ab')$_2$ fragments). Portions of antibodies may be made by any of the above methods, or may be made by expressing a portion of the recombinant molecule. For example, the CDR region(s) of a recombinant antibody may be isolated and subcloned into an appropriate expression vector.

In one embodiment, an antibody or functional part is a human antibody. The use of human antibodies for human therapy may diminish the chance of side effects due to an immunological reaction in a human individual against non-human sequences. In another embodiment, the antibody or functional part is humanized. In another embodiment, an antibody or functional part is a chimeric antibody. This way, sequences of interest, such as for instance a binding site of interest, can be included into an antibody or functional part.

In one embodiment, the antibody may have an IgG, IgA, IgM, or IgE isotype. In one embodiment, the antibody is an IgG.

B. Radiation Therapy for Use in Methods of Treatment

Radiation therapy, also known as high-dose ionizing irradiation, is a component of the present therapeutic approach.

In one mode, the radiation therapy is fractionated radiation therapy. In one embodiment, the fractionated radiation therapy comprises from 2 to 7 fractions. In another embodiment, the fractionated radiation therapy comprises from 3 to 6 fractions. In another embodiment, the fractionated radiation therapy comprises from 4 to 5 fractions. In one mode, the fractionated radiation therapy comprises 2, 3, 4, 5, 6, or 7 fractions. In one embodiment, the fractionated radiation therapy comprises 5 fractions.

In one mode, the radiation therapy fractions are administered in sequential days. In one mode, radiation therapy may include more than one dose on a day and/or doses on sequential days. In one mode, the radiation therapy fractions are administered on day 1, day 2, day 3, day 4, and day 5. In another mode, the radiation therapy comprises about 10 Gy in 5 fractions (i.e., 2 Gy on each of 5 days).

Other fractionation schedules may be employed including accelerated fractionation (treatment given in larger daily or weekly doses to reduce the number of weeks of treatment), hyperfractionation (smaller doses of radiation given more than once a day), or hypofractionation (larger doses given once a day or less often to reduce the number of treatments).

The radiation therapy may be x-rays, gamma rays, or charged particles. The radiation therapy may be external-beam radiation therapy or internal radiation therapy (also called brachytherapy). Systemic radiation therapy, using radioactive substances, such as radioactive iodine, may also be employed.

External-beam radiation therapy includes 3D conformational radiation therapy, intensity-modulated radiation therapy, image-guided radiation therapy, tomotherapy, stereotactic radiosurgery, proton therapy, or other charged particle beams.

C. Cancers for Treatment

The present methods may be used to treat a variety of types of cancer. In one aspect, the method may be used to treat melanoma, colorectal cancer, or breast cancer. In one embodiment, the breast cancer is triple negative breast cancer.

In one embodiment, the cancer is cancer is adrenocortical tumors, adrenal cancer, anal cancer, bile duct cancer, bladder cancer, bone cancer, brain cancer, breast cancer, central nervous system cancer, cervical cancer, chest cancer, colon cancer, colorectal cancer, endometrial cancer, epidermoid carcinoma, esophageal cancer, eye cancer, glioblastoma, glioma, gallbladder cancer, gastrointestinal carcinoid tumors, gastrointestinal stromal tumor, gestational trophoblastic disease, head and neck, Hodgkin disease, Kaposi sarcoma, kidney cancer, laryngeal and hypopharyngeal cancer, leukemia, liver cancer (such as hepatocellular carcinoma), lung cancer (including non-small cell, small cell, and lung carcinoid tumors), lymph node cancer, lymphoma, lymphoma of the skin, melanoma, mesothelioma, mouth cancer, multiple myeloma, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary cancer, prostate cancer, pediatric malignancies, rectal cancer, retinoblastoma, rhabdomyosarcoma, salivary gland, sarcoma, skin cancer, small intestine cancer, stomach cancer, testicular cancer, thymus cancer, throat cancer, thyroid cancer, uterine cancer, vaginal cancer, or vulvar cancers.

Reference will now be made in detail to the present exemplary embodiments, examples of which are illustrated in the accompanying drawings. Wherever possible, the same reference numbers will be used throughout the drawings to refer to the same or like parts. Other embodiments will be apparent to those skilled in the art from consideration of the specification and practice disclosed herein. The embodiments are further explained in the following examples. These examples do not limit the scope of the claims, but merely serve to clarify certain embodiments. It is intended that the specification and examples be considered as exemplary only, with a true scope and spirit being indicated by the following claims.

EXAMPLES

Example 1

Methods

A) Mice and Cell Lines

BALB/c and C57Bl/6 mice were obtained from Harlan, U.K. All animal experiments were approved by a local ethical committee and performed under a United Kingdom Home Office license. CT26 murine colon carcinoma cells (ATCC) and 4434 cells isolated from BRafV600E p16$^{-/-}$ mice (Richard Marias, Cancer Research UK, Manchester Institute) were maintained in DMEM, and 4T1 triple negative breast cancers (ATCC) maintained in RPMI-1640, supplemented with 10% FCS, 1% L-glutamine (Invitrogen, U.K.). All cell lines were routinely screened to confirm the absence of *Mycoplasma* contamination.

B) Tumor Therapy

Mice were inoculated sub-cutaneously (s.c.) with either $5\times10^5$ CT26, $1\times10^5$ 4 T1 or $5\times10^6$ 4434 cells. Irradiations were performed 7-10 days after inoculation (when tumors were at least 100 mm$^3$) using a Pantak HF-320 320 kV x-ray unit (Gulmay Medical, U.K.). The machine was operated at 300 kV, 9.2 mA, with filtration fitted in the x-ray beam to give a radiation quality of 2.3 mm Cu half-value layer. Mice were positioned at a distance of 350 mm from the x-ray focus, where the dose rate was 0.80 Gy/min. Administration of αPD-1 (clone RMPI-14), αPD-L1 (clone 10F.9G2) (both Biolegend) or isotype control mAb (IgG2a and IgG2b respectively) commenced on day 1 of the fractionated RT cycle (unless otherwise stated) and was administered intraperitoneally (i.p.) 3qw for up to 3 weeks at a dose of 10 mg/kg in a dose volume of 100 μl/10 g in PBS. For cellular and cytokine depletion experiments mice received either αCD8 mAb; clone YTS169 (a gift from M. Glennie, Southampton University), αCD4 mAb; clone GK1.5 (Biolegend), αAsialo-GM1 (Wako Chemicals) or αIFNγ; clone XMG1.2 (BioXcell). Peripheral blood was sampled during therapy to confirm cellular depletion. For tumor rechallenge experiments, long-term surviving (LTS) mice were implanted contralaterally with tumor cells a minimum of 100 days after previous tumor implantation. Additional control mice were also implanted to confirm tumor growth. Experimental groups contained at least 5 mice/group and are representative at least 2 independent experiments.

C) Measurement of Cytokine Production by CD8$^+$ T Cells Isolated from Long-Term Surviving Mice For in vitro stimulation $3.5\times10^6$ splenocytes from either LTS or control mice were cultured for 5 days in RPMI-1640 supplemented with 10% FCS, 100 U/ml penicillin, 100 μg/ml streptomycin, 1% L-glutamine, 50 μM 2-ME and 10 IU/ml human recombinant IL-2 in the presence of either $1\times10^6$ tumor cells irradiated with 50 Gy or 1 μmol/ml of the H2-Ld restricted peptides SPSYVYHQF (SEQ ID NO: 91) (AH1)/TPHPARIGL (SEQ ID NO: 92) (β-galactosidase) (Anaspec, U.K.). Experimental groups contained 3-5 mice and are representative of 2 independent experiments. After 5 days in culture, cells were restimulated at a 1:1 ratio with 50 Gy irradiated tumor cells for 16 hours in the presence of 3 ug/ml Brefeldin A (BD Pharmingen, U.K.) and 100 IU/ml human recombinant IL-2 (Chiron, NL). For FACS analysis, cells were washed and incubated with rat anti-CD16/32 (eBioscience, U.K.) to block non-specific binding and then stained with a FITC conjugated anti-CD8a mAb (eBioscience, U.K.). Cells were then fixed/permeabilized and stained for expression of IFNγ using an APC conjugated mAb (eBioscience, U.K.).

D) Tumor and Immune Cell Phenotyping by Flow Cytomtery

To obtain single cell suspensions, tumors were processed using a gentleMacs dissociator and a murine tumor dissociation kit (Miltenyi Biotec, U.K.). For analysis, non-specific binding was blocked as described above and expression of CD4, CD8 (BD Biosciences, UK), CD45, NKP46, PD-1 and PD-L1 examined by multi-parameter flow cytometry (all eBioscience unless otherwise stated).

E) In Vitro Co-cultures

Tumor cells were cultured in the presence of 20 ng/ml IFNγ and/or TNFα for 24 hours prior to evaluation of PD-L1 expression by flow cytometry as described above. For co-culture assay either resting or activated splenocytes (treated with PBS or phorbol 12-Myristate 13-Acetate and Ionomycin cell stimulation cocktail respectively, (eBioscience, UK)) were co-cultured at a 1:1 ratio with tumor cells and tumor cell expression of PD-L1 determined as described above. Silencing of IFNγR1 expression was achieved by lentiviral transduction of cells with ShRNA (cells were also transduced with non-targeting ShRNA as controls) (Thermo Scientific, UK). Measurement of splenocyte cytokine production (IFNγ and TNFα) was measured by intracellular flow cytometry as described above.

Example 2

Blockade of PD-1 or PD-L1 Enhances the Therapeutic Efficacy of RT

Radiation therapy has been shown to modulate the immunogenicity of tumor cells but is rarely able to generate durable therapeutic responses that lead to systemic anti-tumor immunity alone. We show that low doses of local fractionated dose RT delivered as about 10 Gy in 5 fractions leads to increased tumor cell expression of PD-L1 with elevated expression evident 1, 3 and 5 days after the last dose of RT when compared to time-matched, non-treated (NT) mice (FIGS. 1A and B). This RT-mediated increase in tumor cell PD-L1 expression peaks at 72 hours after the last dose of RT and although it declines significantly by 7 days post RT (when compared to expression at days 1 and 3; P<0.05 and P<0.01 respectively, Mann-Whitney test) remains elevated when compared to NT mice (P<0.05, Mann-Whitney test).

Figure 1C:
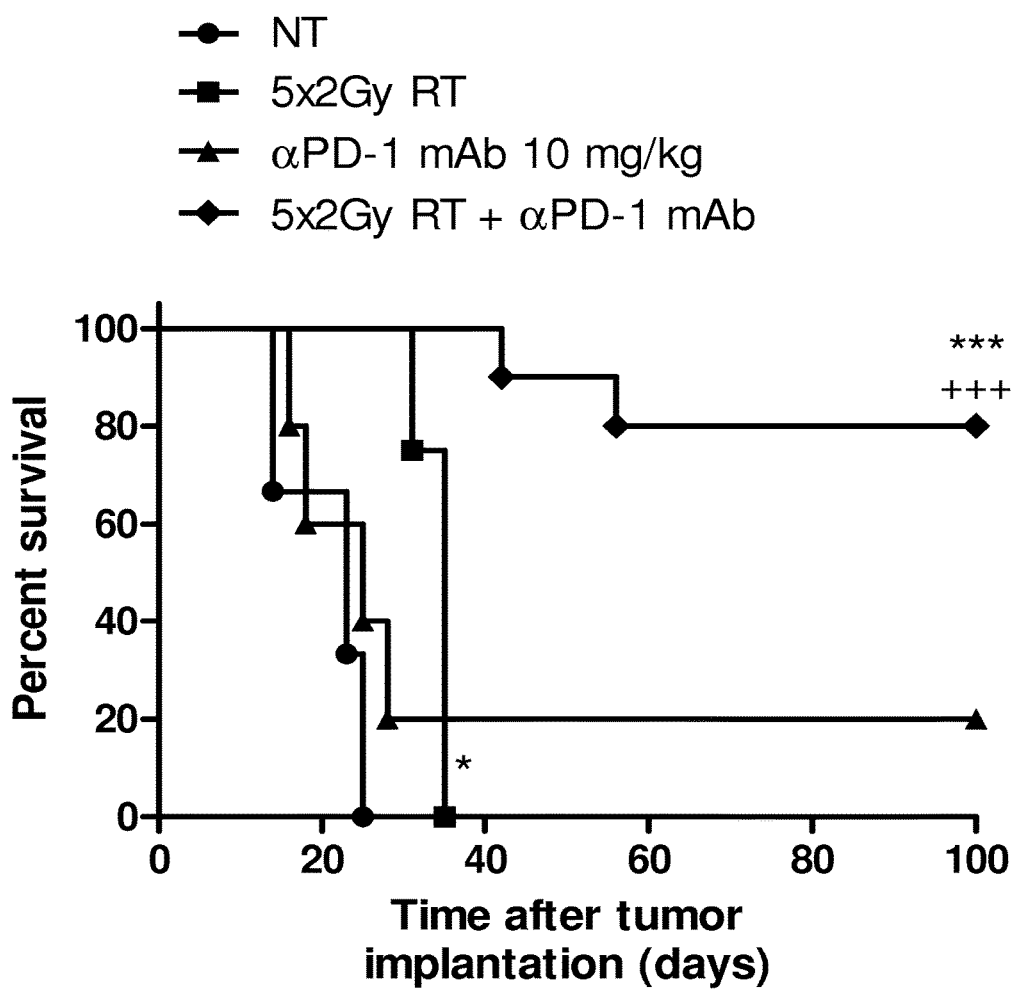
Figure 1D:
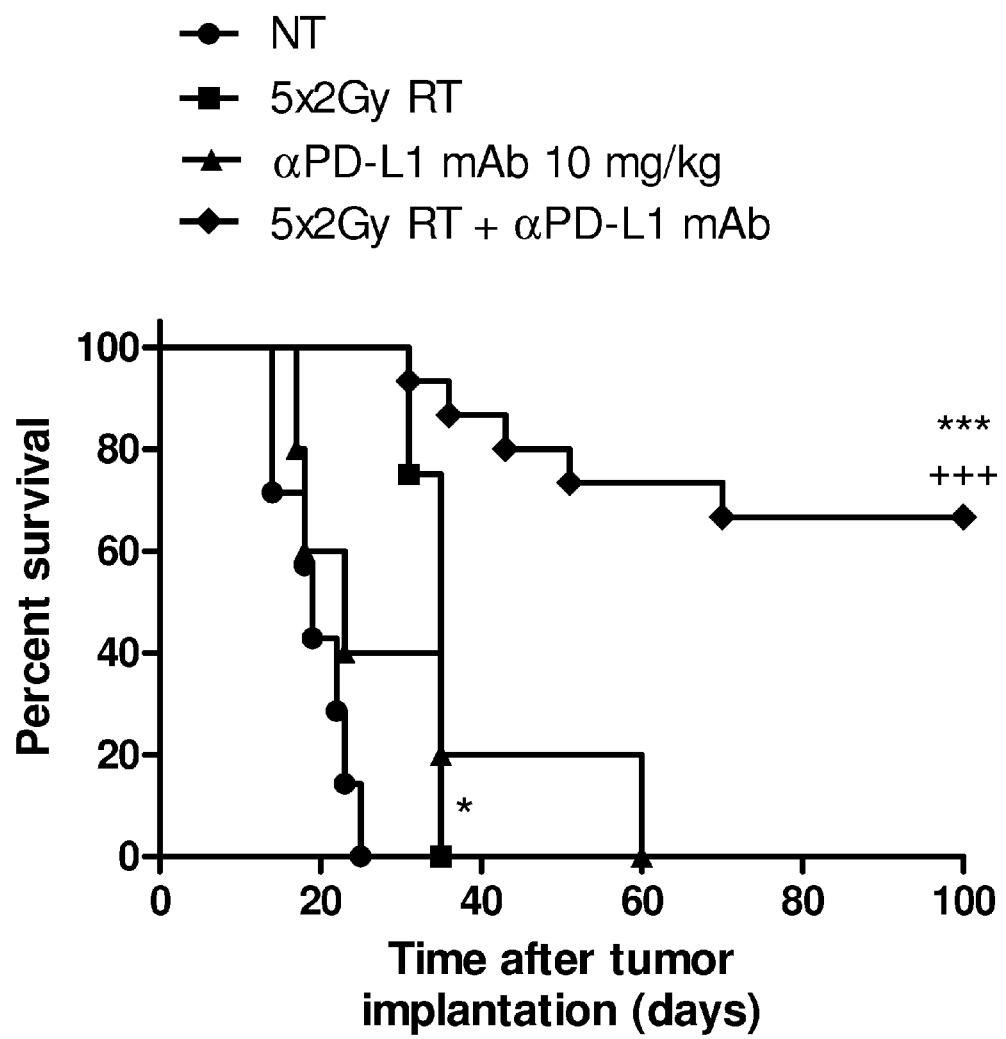
Figure 7:
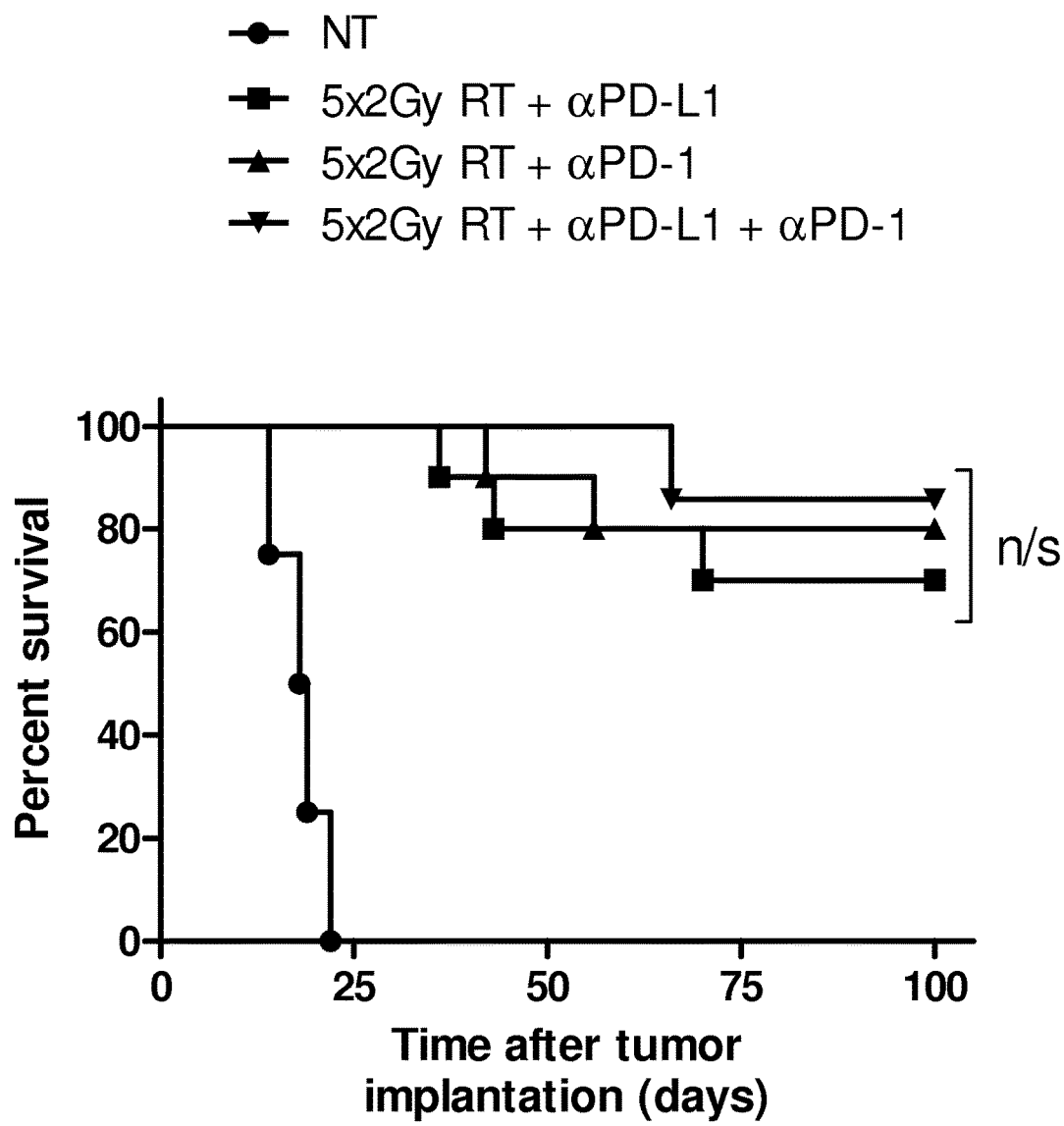
FIG. 7 shows blockade of both PD-1 and PD-L1 does not further enhance efficacy in combination with fractionated RT in CT26-tumor bearing mice. A) Survival curve following fractionated dose RT (as 10 Gy in 5 daily fractions of 2 Gy) alone or in combination with αPD-1, αPD-L1 or a combination of both mAb dosed 3qw for 3 weeks. n/s, P>0.05, log-rank; Mantel-Cox test. Experimental groups contained at least 5 mice and are representative of at 2 independent experiments.

Given these observations we hypothesized that the immune response generated following RT may be limited through the PD-1/PD-L1 axis. Local RT delivered as about 10 Gy in 5 daily fractions was found to significantly improve survival in mice bearing established CT26 tumors when compared to NT controls (FIGS. 1C and D; P<0.05 Log-rank; Mantel-Cox test). Our data demonstrate that this RT-mediated local tumor control can be substantially improved through combination with either αPD-L1 mAb or αPD-1 mAb (FIGS. 1C and D; P<0.001 Log-rank; Mantel-Cox test). Combined therapy led to a synergistic anti-tumor response which was curative in 66% and 80% of mice that received RT in combination with αPD-L1 mAb or αPD-1 mAb respectively. In contrast to combination with RT, monotherapy with either αPD-L1 mAb or αPD-1 mAb did not significantly improve survival (FIGS. 1C and D; P>0.05 Log-rank; Mantel-Cox test). Further, no significant benefit was observed when mice received RT in combination with both αPD-1 and αPD-L1 mAb vs. combination with either mAb alone (FIG. 7).

Figure 1E:
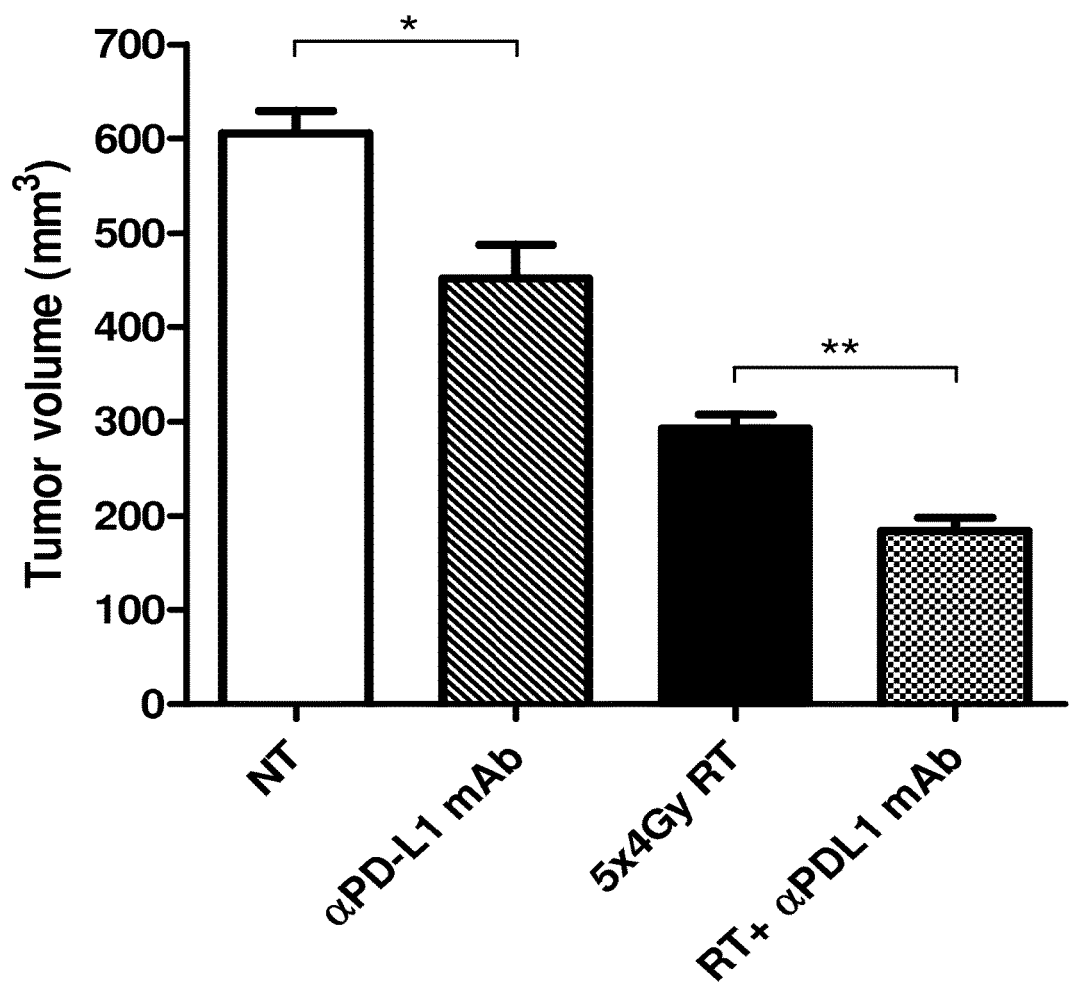
Figure 1F:
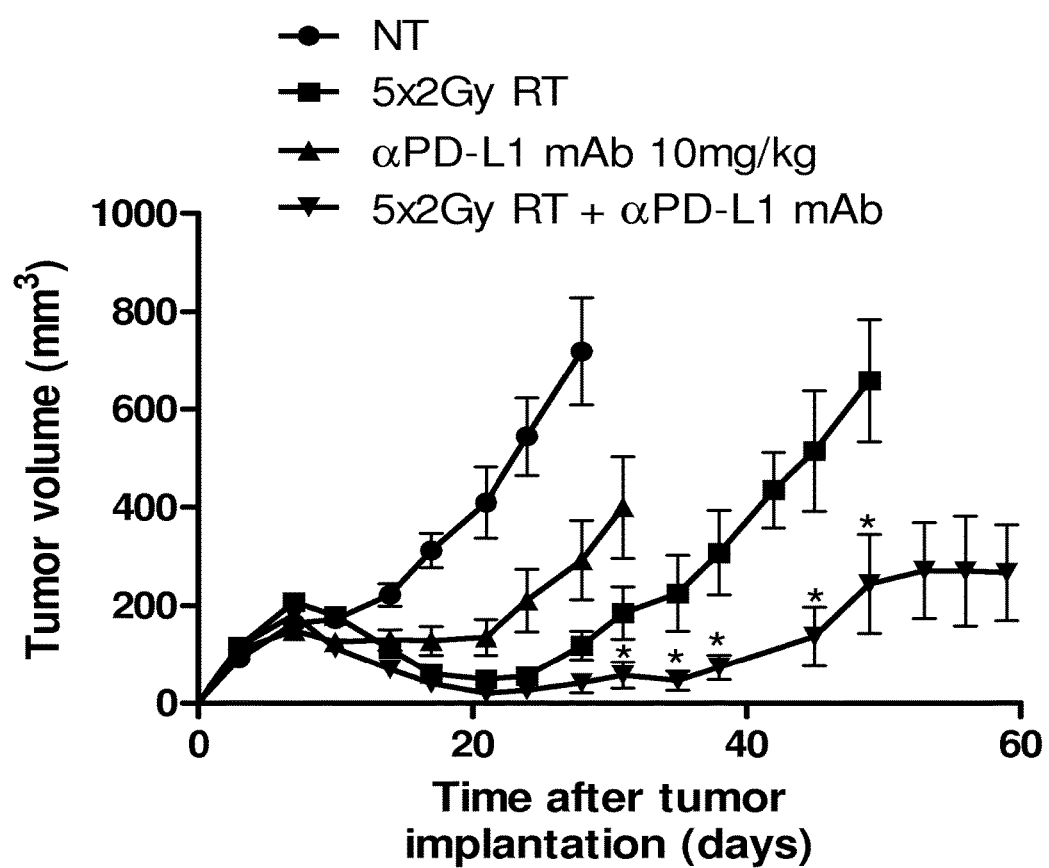
Figure 8A:
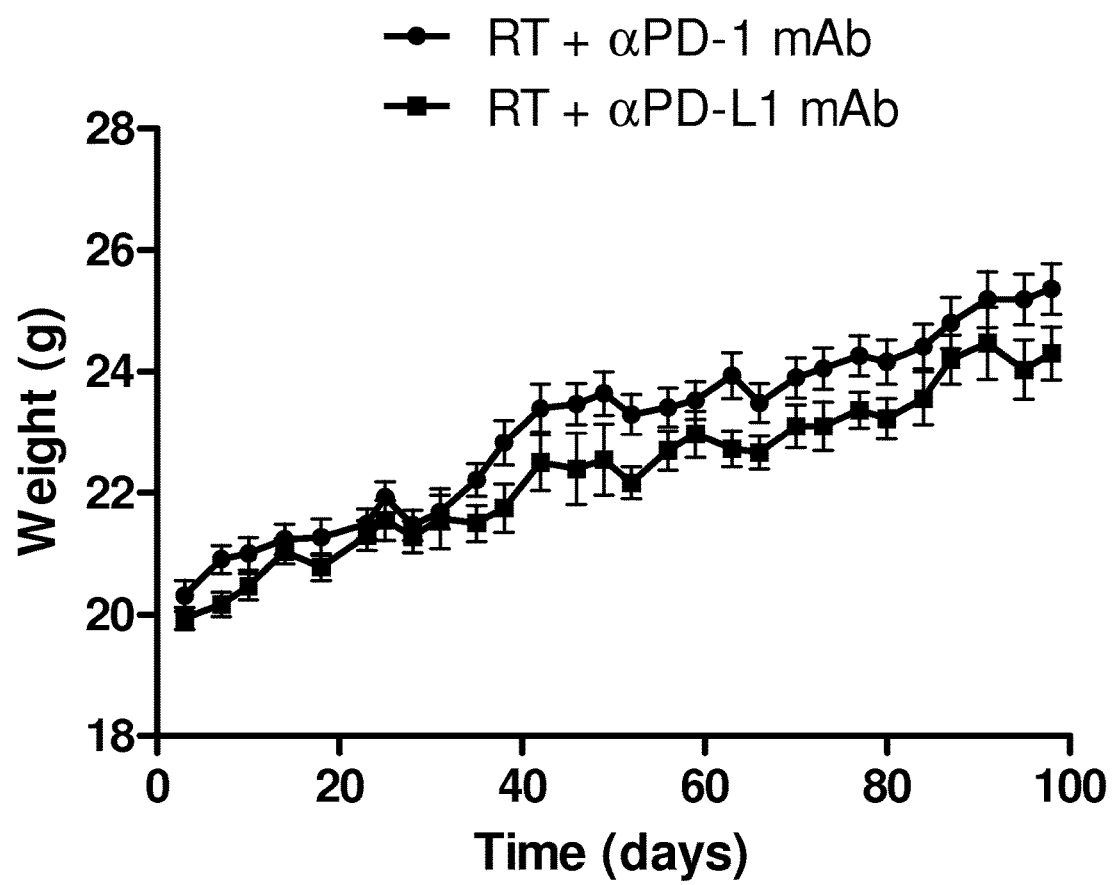
FIGS. 8A-8B show combination therapy with fractionated RT and either αPD-1 or αPD-L1 mAb is well tolerated in mice. CT26 tumor bearing mice received 10 Gy RT delivered in 5 daily fractions of 2 Gy either alone or in combination with αPD-L1 mAb dosed at 10 mg/kg 3qw either for 3 weeks or 1 week. Experimental groups contained at least 7 mice and are representative of at least 2 independent experiments. n/s, P>0.05, Mann-Whitney test.
Figure 8B:
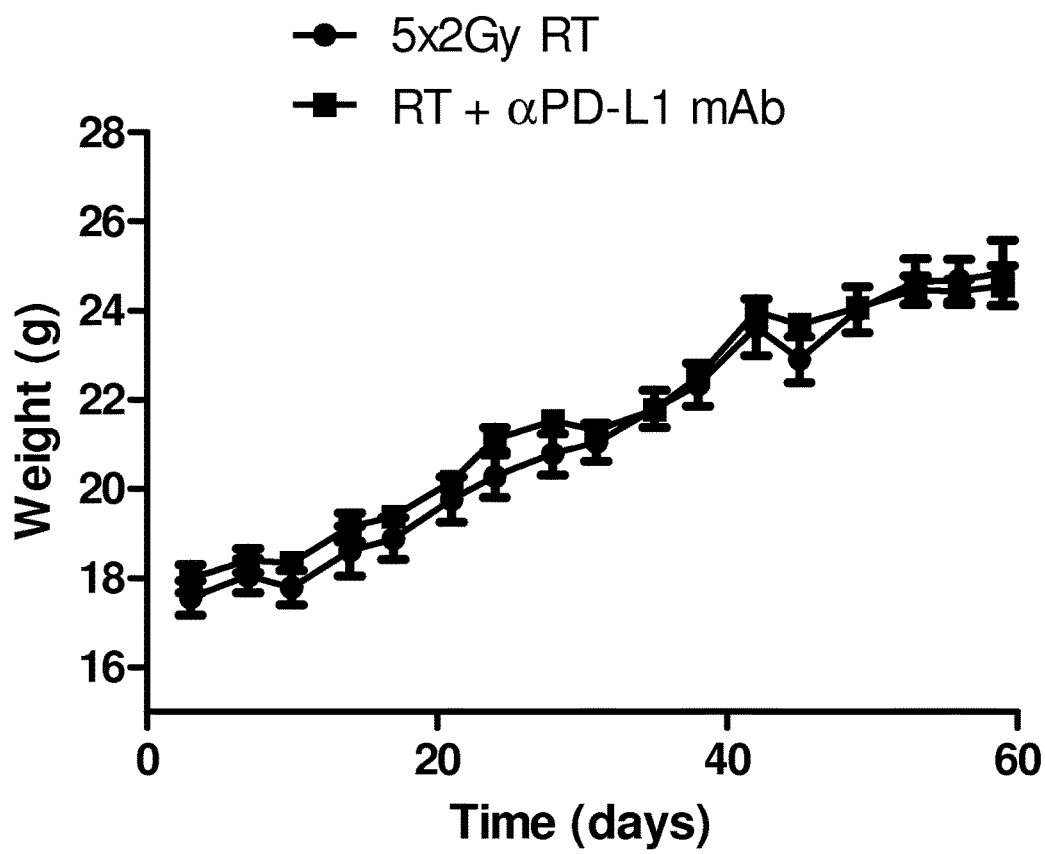

Blockade of PD-L1 also improved response to RT in mice bearing established 4T1 tumors where combined therapy significantly reduced tumor burden by 38% when compared to RT alone (FIG. 1E; 10 days post start of therapy; 184.3±13.5 mm$^2$ vs. 292.8±14.3 mm$^2$ respectively, P<0.01 Mann-Whitney test) and significantly improved survival (P<0.001 Log-rank; Mantel-Cox test; data not shown). Similar results were also observed in mice bearing established 4434 melanomas (FIG. 1F). Combination therapy with local RT and mAbs targeting either PD-1 or PD-L1 was well tolerated in both BALB/c and C57Bl/6 mice (FIGS. 8A and B). These preclinical data clearly demonstrate the potential to improve outcome following low dose fractionated RT of established solid tumors through blockade of the PD-1/PD-L1 axis.

Example 3

Figure 2A:
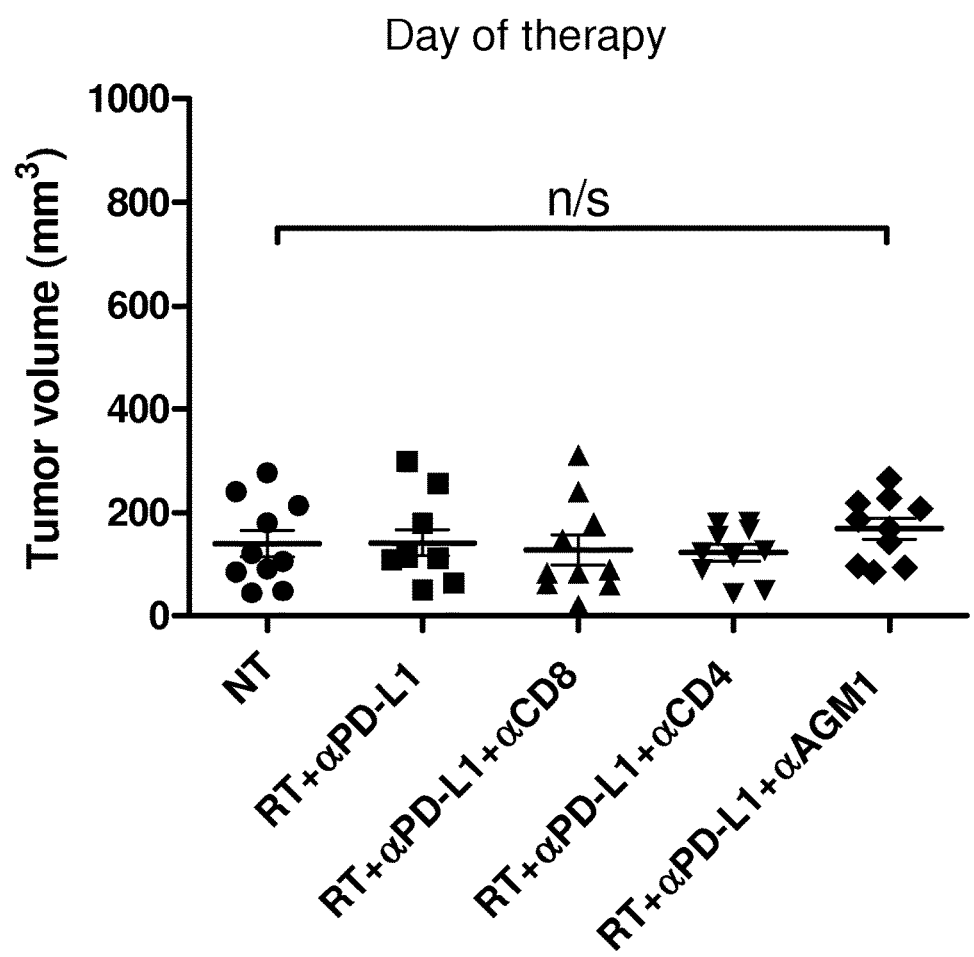
FIGS. 2A-2C demonstrate that therapeutic activity of fractionated RT and αPD-L1 mAb combination is dependent on the activity of CD8+ T-lymphocytes.
Figure 2A:
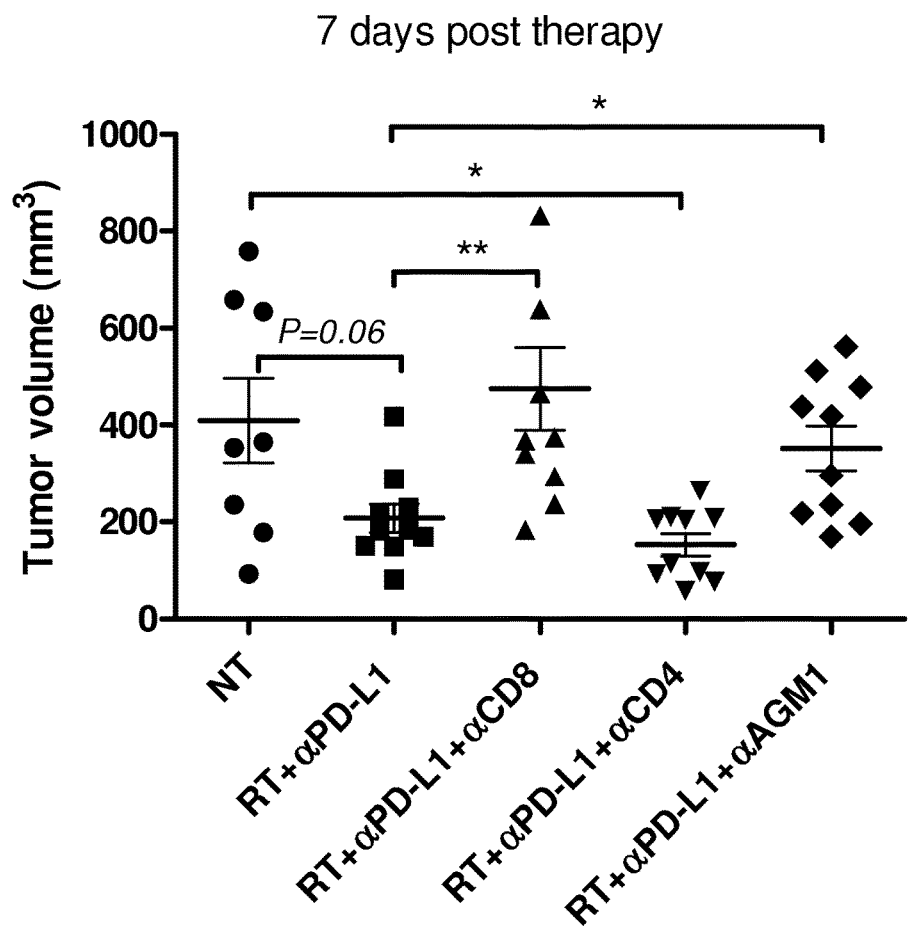
Figure 2A:
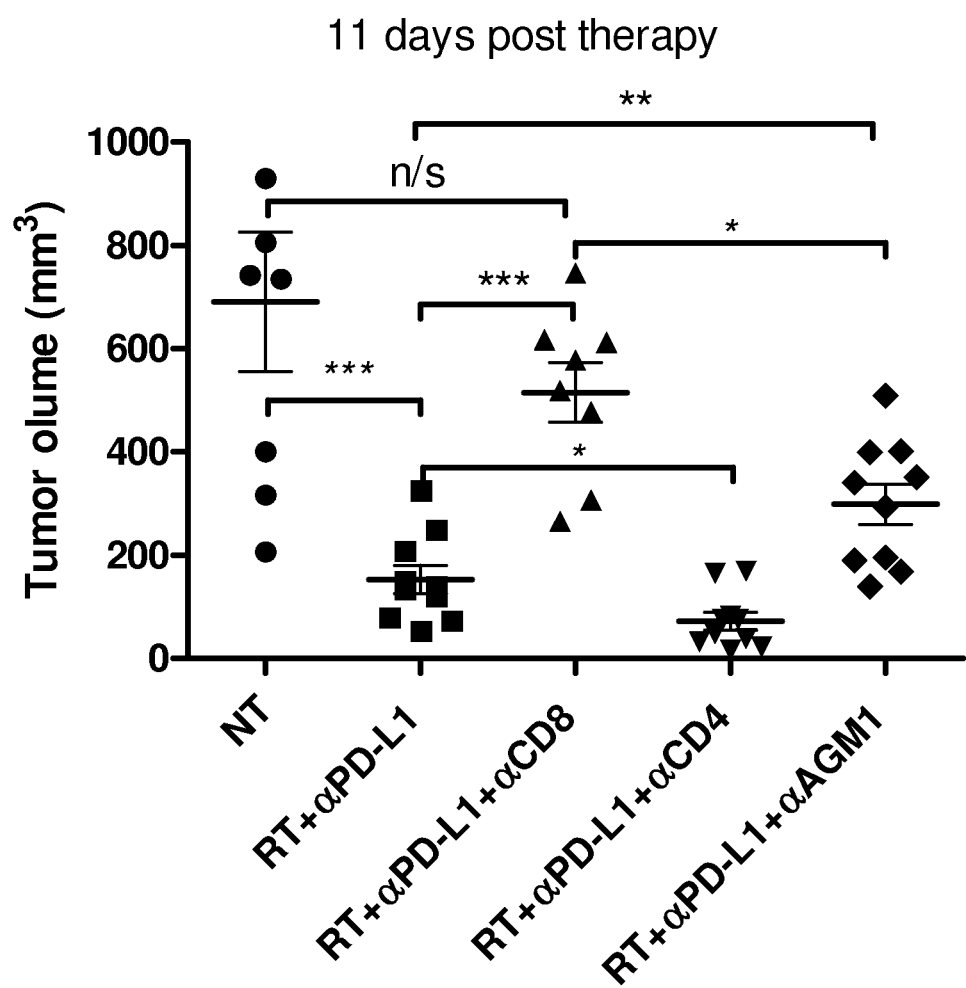
Figure 9A:
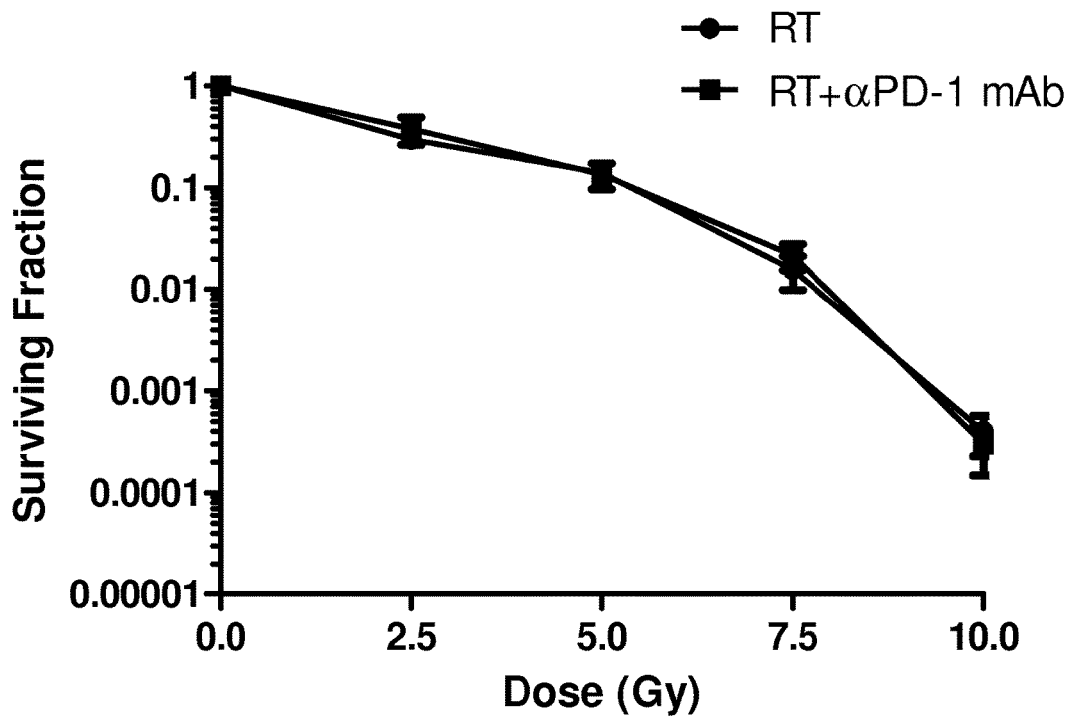
FIGS. 9A-9C illustrate that treatment of tumor cells with αPD-1 or αPD-L1 mAb does not sensitise to radiation-induced cell death in vitro. Clonogenic survival curves for CT26 cells (FIG. 9A), 4T1 cells (FIG. 9B) and 4434 cells (FIG. 9C) treated with RT (2.5-10Gy) in the presence absence of 2 µg/ml αPD1 or αPD-L1.
Figure 9A:
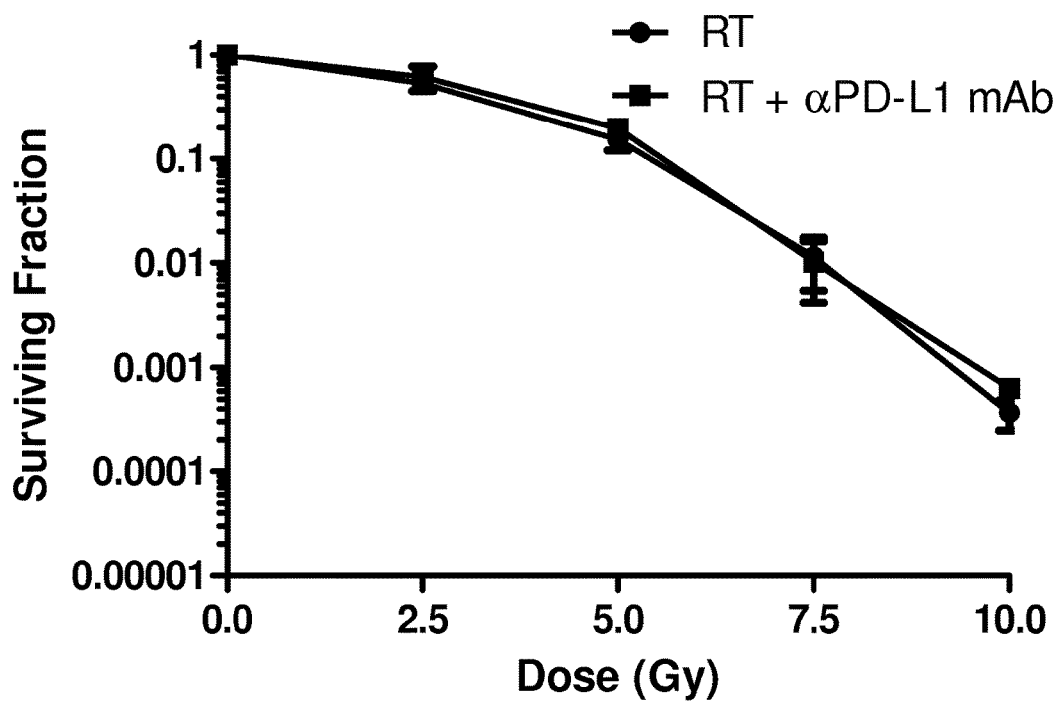
Figure 9B:
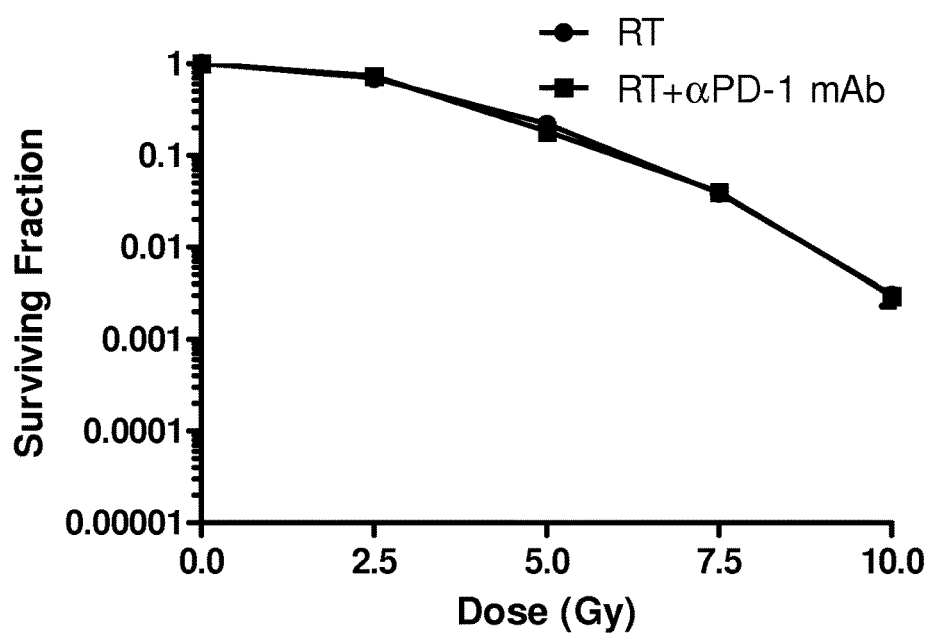
Figure 9B:
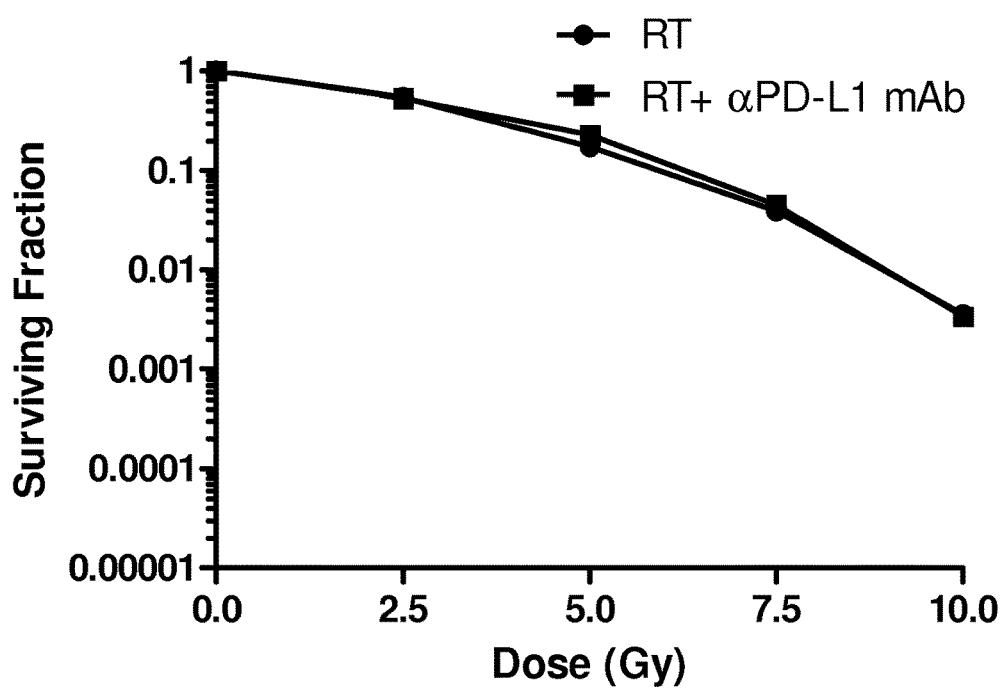
Figure 9C:
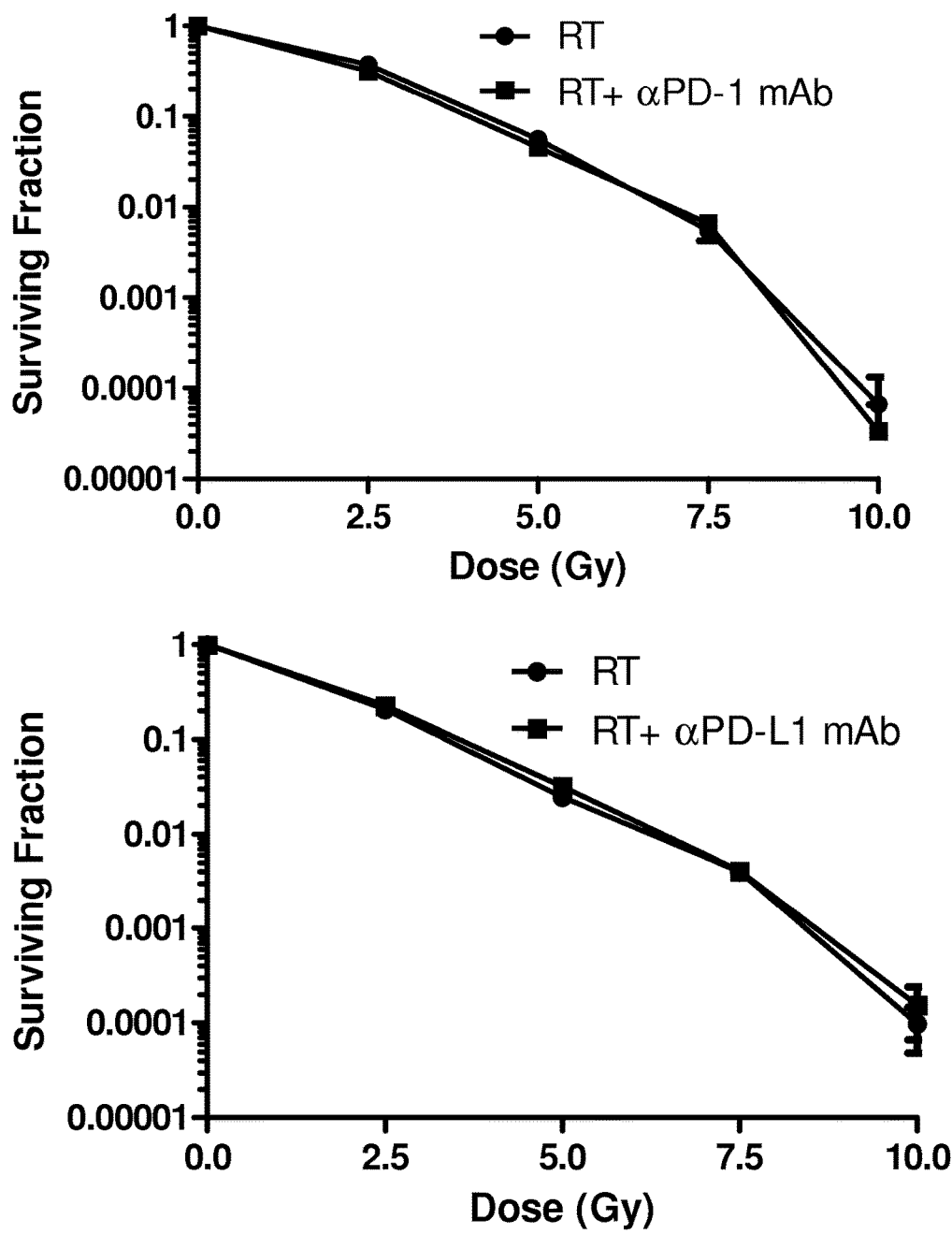

NK Cells Contribute to Local Tumor Control Following Combination Therapy but Long-term Survival is Dependent on CD8⁺ T Cells We next investigated the mechanisms underlying the long-term tumor control observed following combination RT and αPD-L1 mAb therapy. Initially colony forming assays were used to confirm that αPD-1 and αPD-L1 mAb were not acting as radiation sensitizers through direct interaction with tumor cells (FIG. 9A-C). Using depleting antibodies, we next explored the role of effector T cells and NK cells in mediating anti-tumor activity following RT/αPD-L1 mAb combination therapy. Our data demonstrate that as early as 7 days after the start of a 5 day fractionated RT cycle (with αPD-L1 mAb therapy commencing on day 1 of the RT cycle) reduced tumor burden is evident in mice following combination therapy when compared to NT mice (207.5±29.2 mm² vs. 409.4±86.88 mm² respectively; $P=0.067$, Mann-Whitney U test) (FIG. 2A). However, this statistical trend to reduced volume was lost following depletion of either CD8⁺ T cells or NK cells, where tumor volumes were not significantly different from those in NT cohorts ($P=0.52$ and $P=0.70$ respectively, Mann-Whitney U test) but significantly larger than mice that received combination therapy without immune cell depletion ($P<0.01$; combined therapy vs. CD8 depletion, and $P<0.05$; combined therapy vs. NK cell depletion, Mann-Whitney U test). By day 11 post treatment, combination therapy significantly reduces tumor burden when compared to NT controls ($P<0.001$, Mann-Whitney U test). Whilst the depletion of either CD8⁺ T cells or NK cells at this time point reduces the efficacy of combination therapy ($P<0.001$ and $P<0.05$ respectively, Mann-Whitney U test), the relative contribution of CD8⁺ T cells and NK cells becomes more evident with significantly reduced tumor control in CD8 vs. NK cell depleted mice ($P<0.05$, Mann-Whitney U test). Our data also reveal that the depletion of CD4⁺ T cells improved local tumor control following combination therapy (153.2±27.0 mm² vs. 72.7±17.3 mm² respectively; $P<0.05$, Mann-Whitney U test).

Figure 2B:
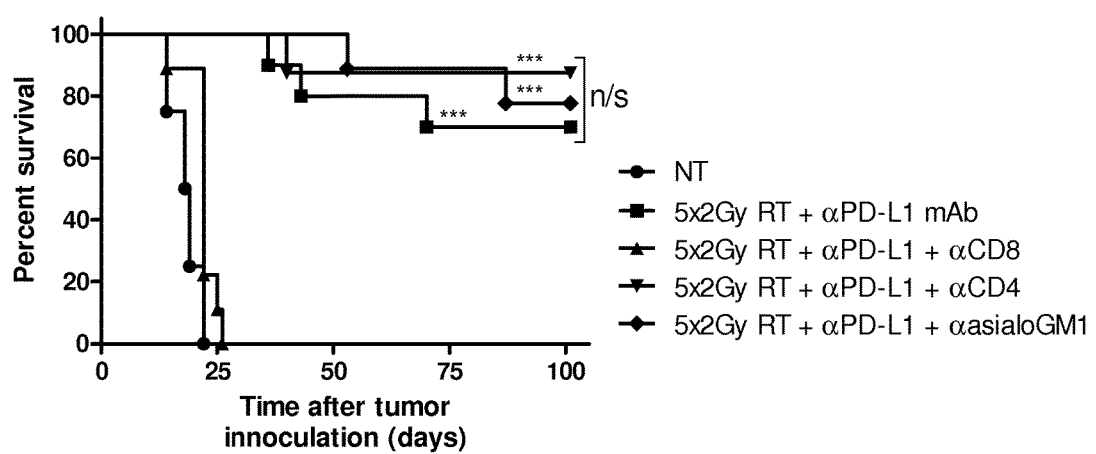
Figure 2C:
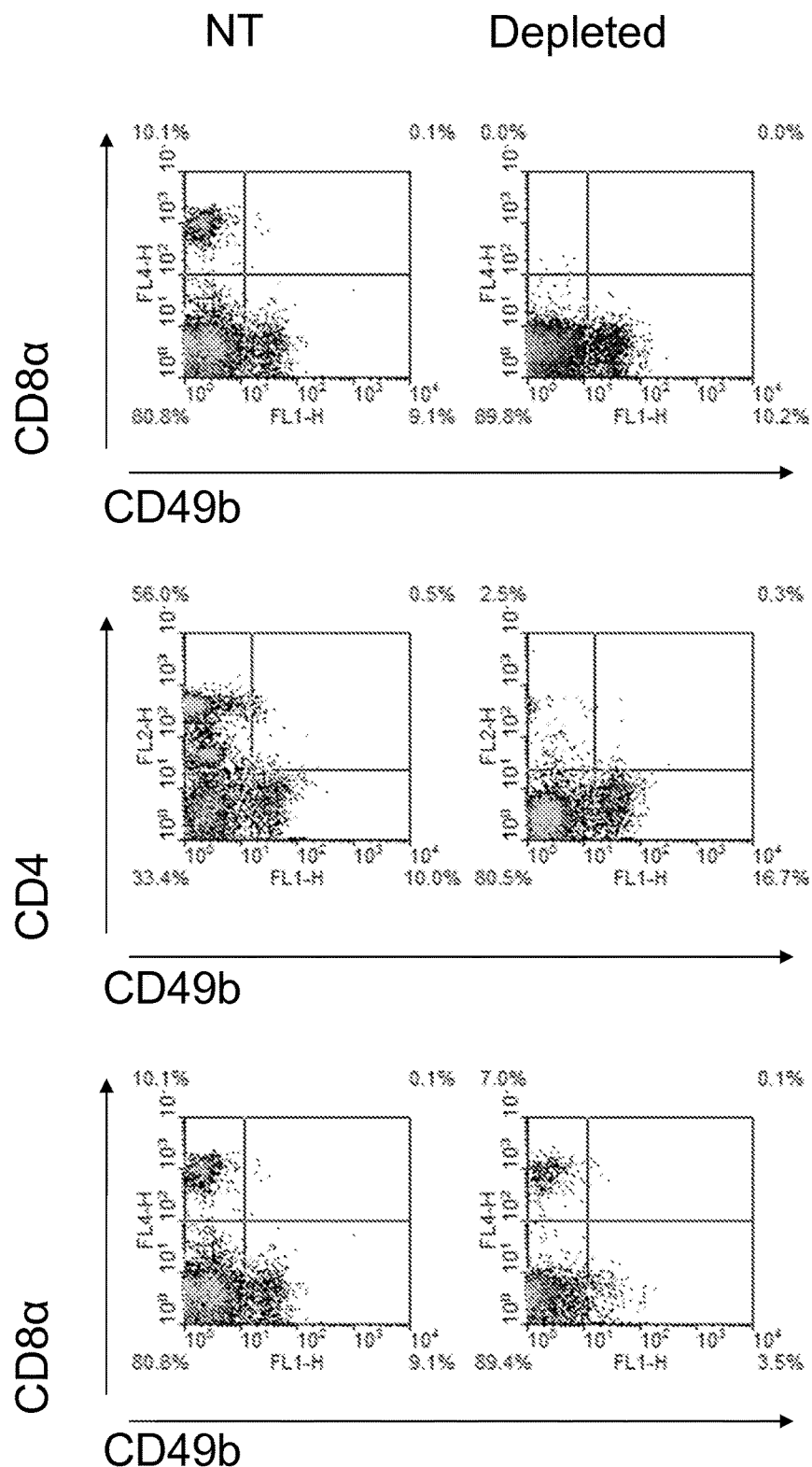

In contrast to early tumor control following combination RT/αPD-L1 mAb therapy, long term survival (LTS) was not impacted by the depletion of NK cells (70% LTS mice following treatment with RT/αPD-L1 vs. 77.8% following combination therapy with NK cell depletion) (FIG. 2B). The depletion of CD4⁺ T lymphocytes increased the frequency of LTS mice from 70% to 87.5% (combination vs. combination+CD4 depletion) but this did not achieve significance ($P>0.05$ Log-rank; Mantel-Cox test). However, the depletion of CD8⁺ T cells completely abrogated the therapeutic efficacy of combination RT/αPD-L1 mAb therapy ($P<0.001$ Log-rank; Mantel-Cox test). Depletion of immune cell populations was confirmed by flow cytometry on peripheral blood samples (FIG. 2C). These data suggest that whilst NK cells may exert some local tumor control this does not impact overall survival and while CD4⁺ T cells are dispensable or even capable of suppressing responses, CD8⁺ T cells appear to mediate effective long term tumor control following treatment with RT and αPD-L1 mAb.

Example 4

Figure 3A:
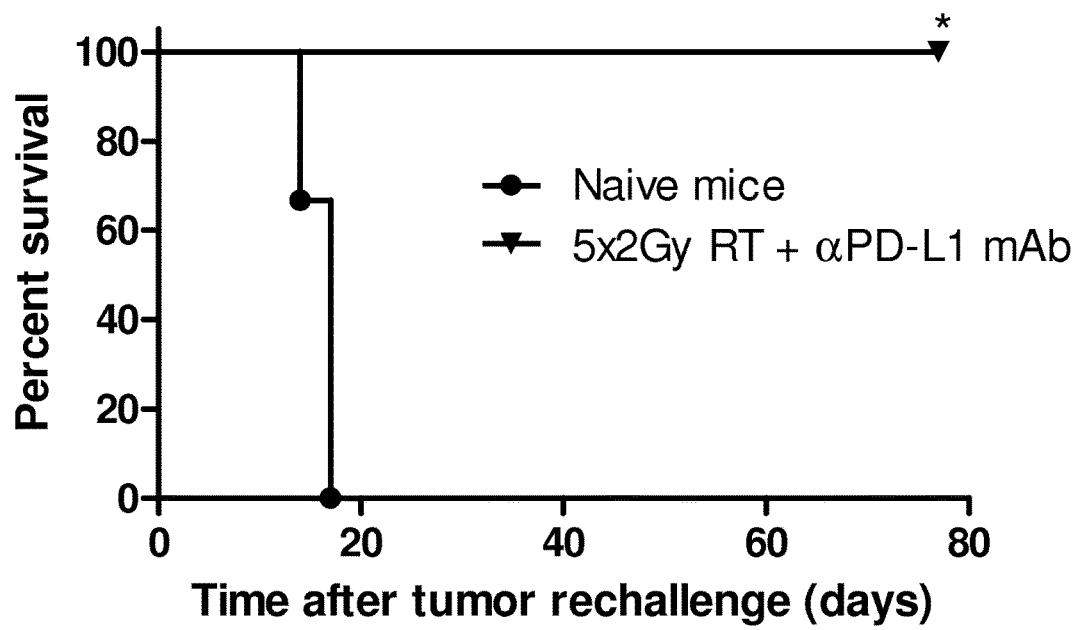
FIGS. 3A-3C show that fractionated RT and αPD-L1 mAb combination generates protective immunological memory.
Figure 3B:
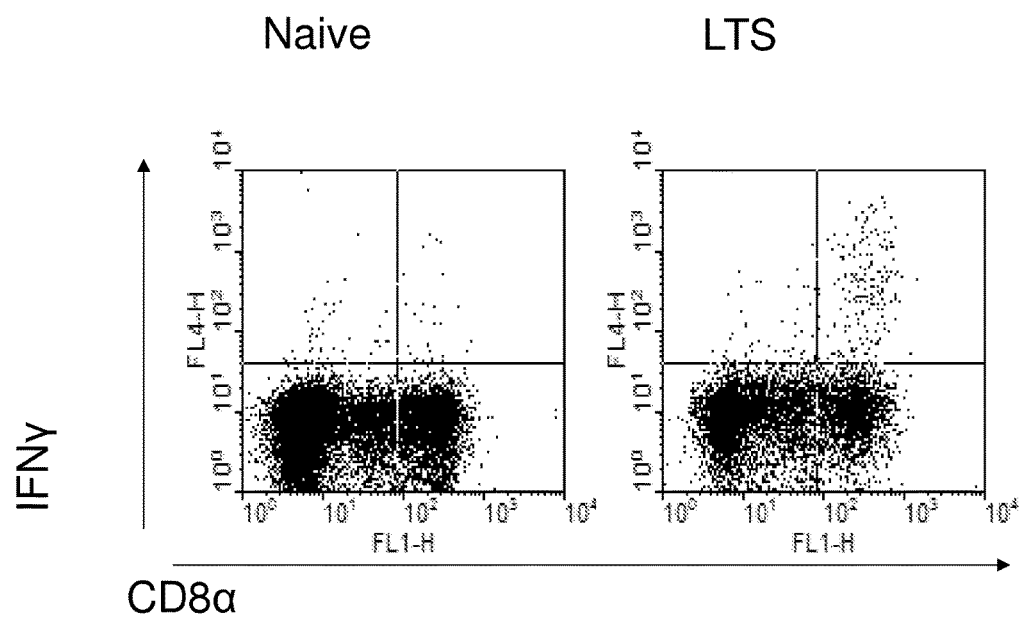
Figure 3C:
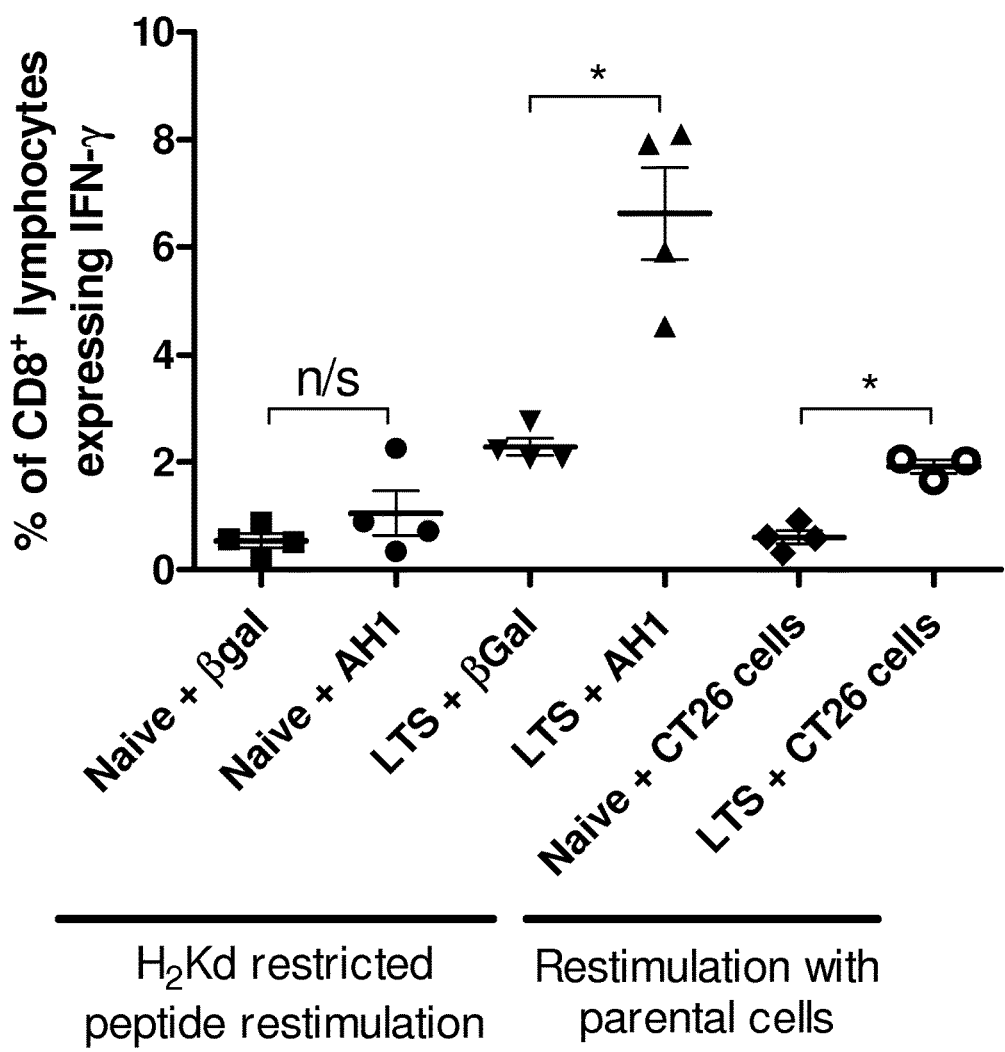

Treatment with αPD-L1 mAb and RT Generates Protective Tumor Antigen-specific Memory T Cell Responses We next investigated whether immunological memory was generated following treatment with RT and αPD-L1 mAb. We show that LTS mice originally treated with RT and αPD-L1 mAb were able to completely reject tumors following contralateral rechallenge (FIG. 3A). To quantify this memory response splenocytes were harvested from LTS mice that had greater than 100 days of disease free survival and the capacity of CD8⁺ T cells to produce IFNγ following co-culture with peptide derived from a CT26 tumor associated antigen (AH1: SPSYVYHQF (SEQ ID NO: 91)), control peptide (β-galactosidase: TPHARIGL (SEQ ID NO: 93)) or with irradiated CT26 cells was assessed (FIGS. 3B and C). Our data reveal that LTS mice were endowed with a significantly greater frequency of IFNγ-producing CD8⁺ T lymphocytes following co-culture with AH1 peptide than naïve mice (6.6%±0.8 vs 2.3%±0.2 respectively; $P<0.05$, Mann-Whitney test). A similar response was observed following co-culture of splenocytes with CT26 cells. Comparison of peptide and tumor cell co-cultures revealed that the frequency of memory CD8⁺ T cells was ~3 fold lower in LTS mice following co-culture with tumor cells than with AH1 peptide and may reflect tumor cell-mediated suppression of T cell activation. Taken together these data demonstrate that RT when combined with blockade of the PD-1/PD-L1 axis in mouse models can generate protective immunological memory in long-term survivors.

Example 5

Figure 4A:
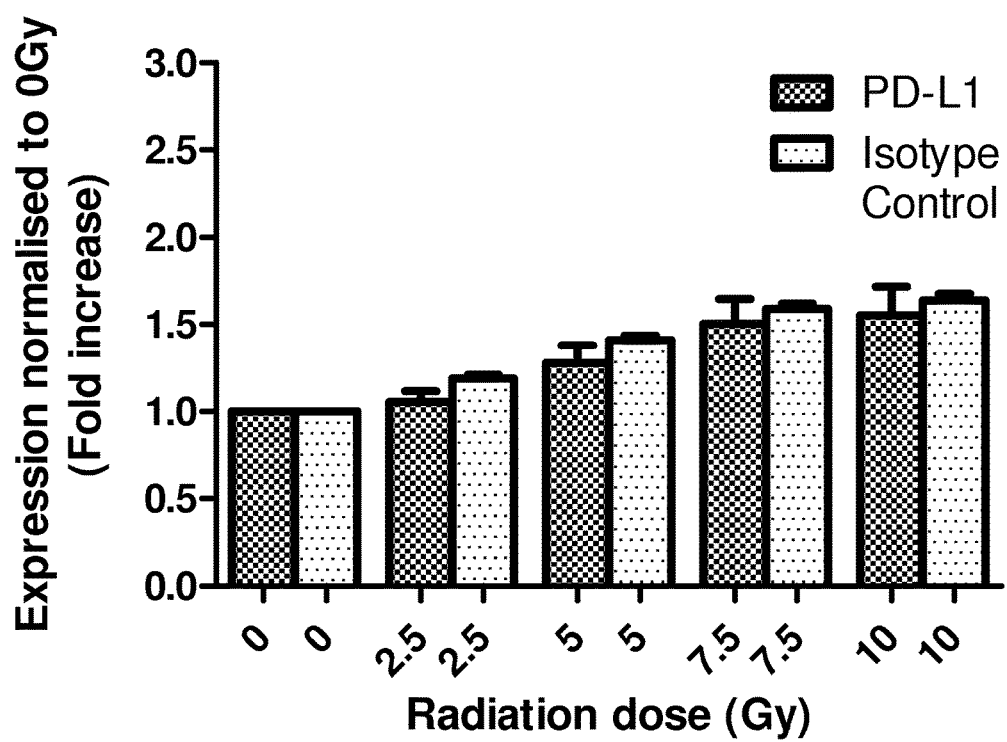
FIGS. 4A-4C illustrate that fractionated RT increases tumor cell PD-L1 expression in vivo and is dependent on CD8$^+$ T cells.
Figure 4B:
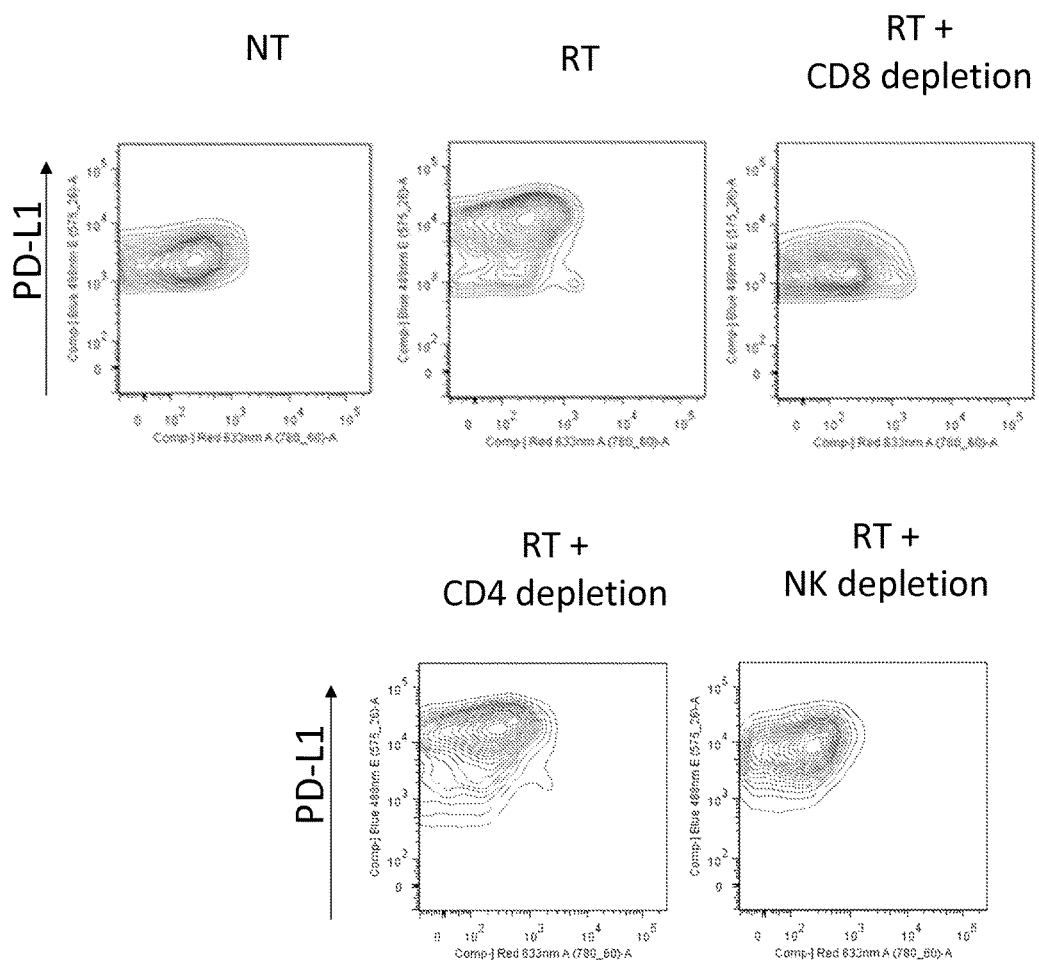
Figure 4C:
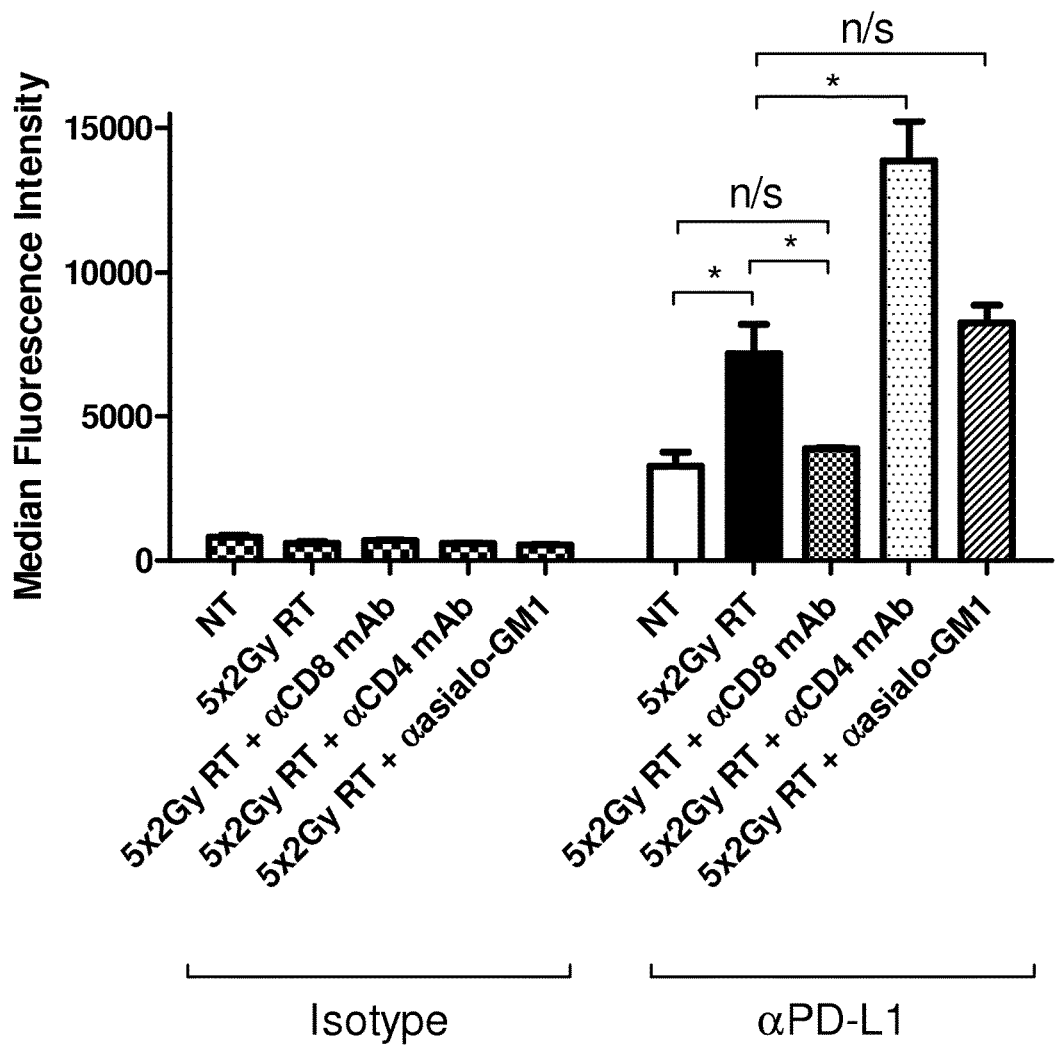

Fractionated RT Leads to CD8⁺ T Cell Dependent Adaptive Upregulation of Tumor Cell PD-L1 Expression Initially we confirmed that treatment of tumor cells with a range of RT doses in vitro did not have any direct impact on expression of PD-L1 (FIG. 4A). To identify which cellular populations within the tumor microenvironment were responsible for modulating tumor cell expression of PD-L1 mice received a fractionated RT cycle in combination with CD8, CD4 or NK cell depleting antibodies. Our data reveal that the depletion of CD8⁺ T cells but not NK cells completely abrogates the RT-mediated upregulation of PD-L1 on tumor cells (FIGS. 4B and C). Interestingly, the depletion of CD4⁺ T cells was found to further augment RT-mediated upregulation of PD-L1 on tumor cells (~2 fold compared to treatment with RT alone).

Example 6

Figure 5A:
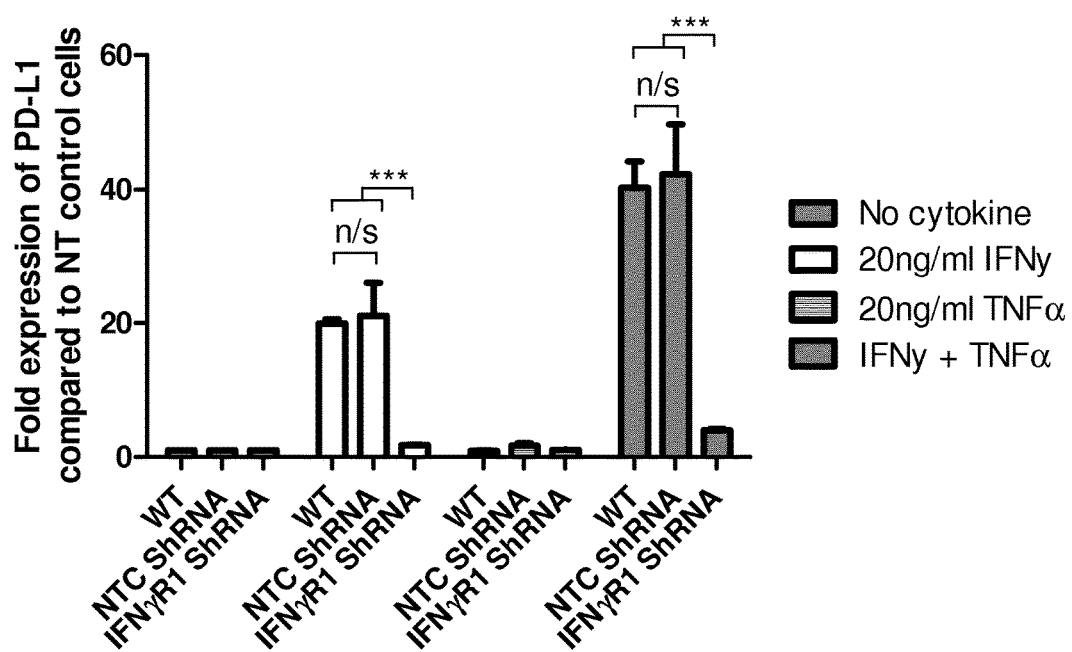
FIGS. 5A-5E show that CD8$^+$ T cell production of IFNγ is responsible for the upregulation of PD-L1 expression on tumor cells following fractionated RT.

Adaptive Upregulation of PD-L1 by Tumor Cells Following Fractionated RT is IFNγ Dependent Given the clinical correlation between IFNγ in the tumor microenvironment and PD-L1 expression (16) and the impact of TNFα on this response (22) we evaluated the impact of these cytokines on PD-L1 in our cell lines. Co-culture of tumor cells with recombinant IFNγ leads to a significant 20 fold increase in cell surface expression of PD-L1 in vitro (FIG. 5A). Furthermore, whilst addition of recombinant TNFα alone has no impact on tumor cell expression of PD-L1, a cocktail of both IFNγ and TNFα can further augment tumor cell PD-L1 expression (~2 fold) when compared to expression with IFNγ alone (FIG. 5A). We show that silencing of IFN-γ-receptor 1 (IFNγR1) on CT26 tumor cells using ShRNA completely abrogates the upregulation of PD-L1 following co-culture with either recombinant IFNγ or both IFNγ and TNFα (FIG. 5A).

Figure 5B:
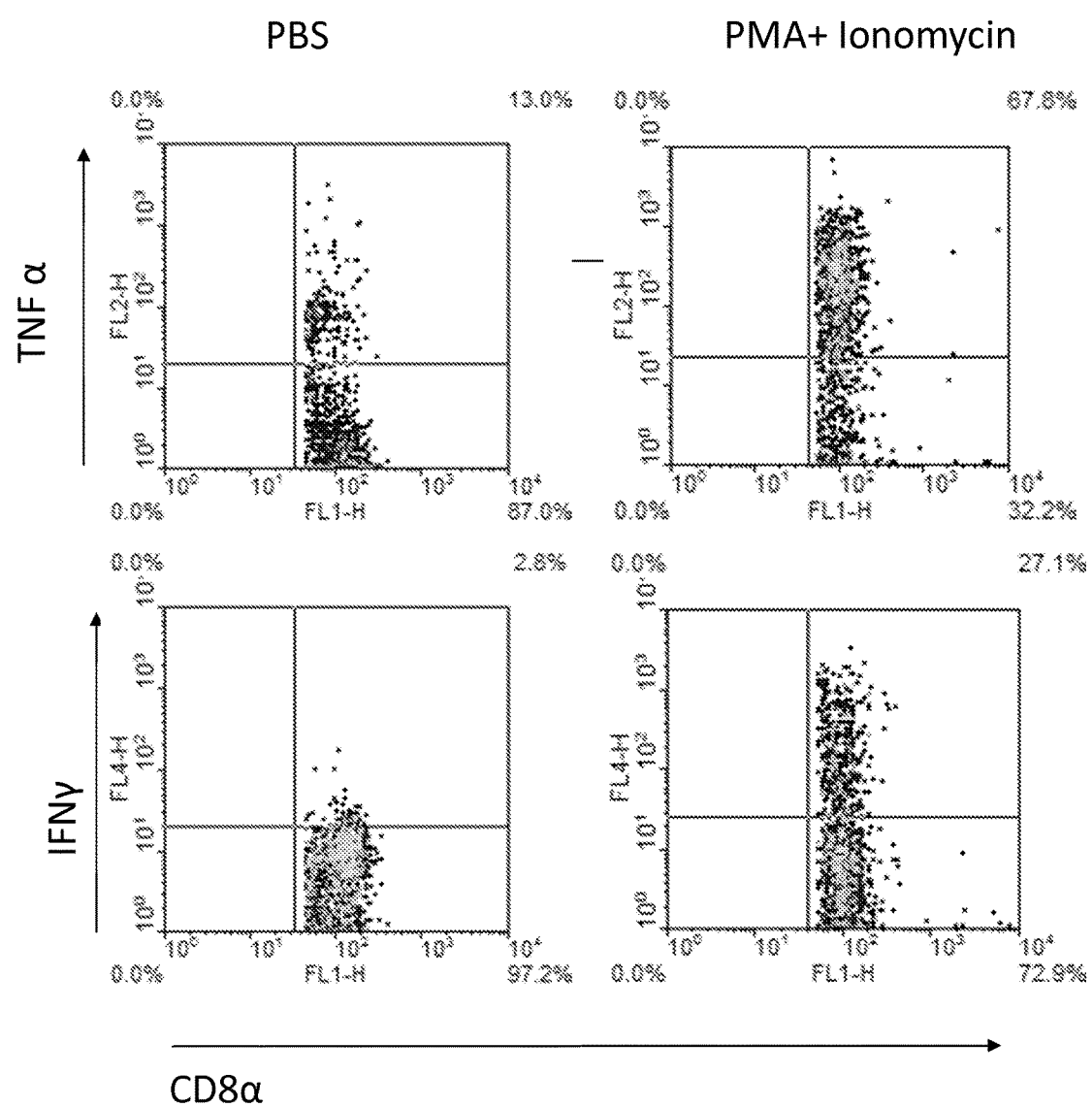
Figure 5C:
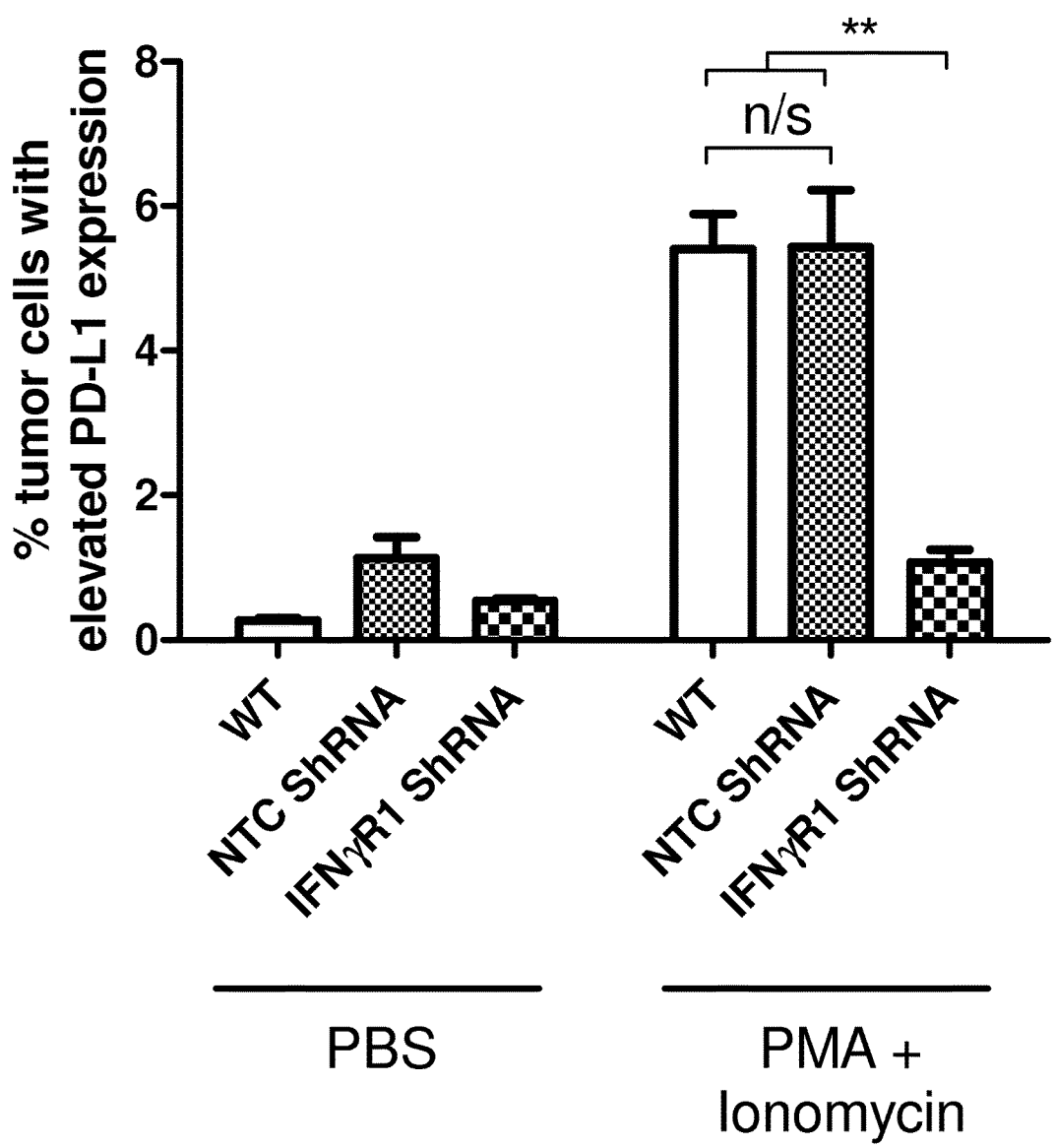

To establish whether activated immune cells could lead to an adaptive change in tumor cell expression of PD-L1 through the production of IFNγ and TNFα, WT CT26 cells and those transduced with either non-targeting ShRNA (NTC ShRNA) and IFNγR1 ShRNA were co-cultured with isolated resting (PBS-treated) and activated (phorbol 12-myristate 13-acetate (PMA) and ionomycin-treated) splenocytes (FIGS. 5B and C). Importantly, these experiments demonstrate that activated immune cells can elevate tumor cell PD-L1 expression at physiologically relevant concentrations of IFNγ and TNFα, in an IFNγR1-dependent manner.

Figure 5D:
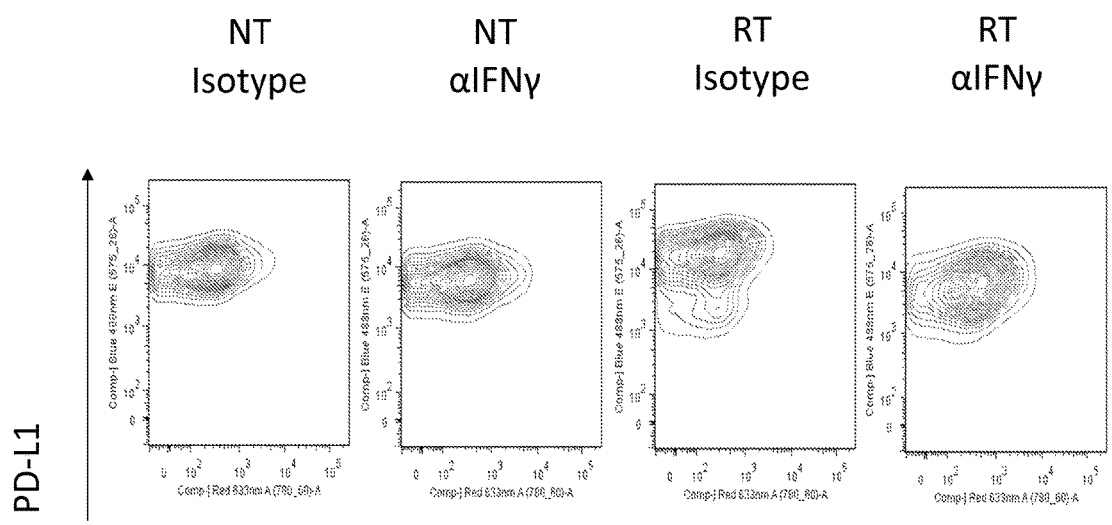
Figure 5E:
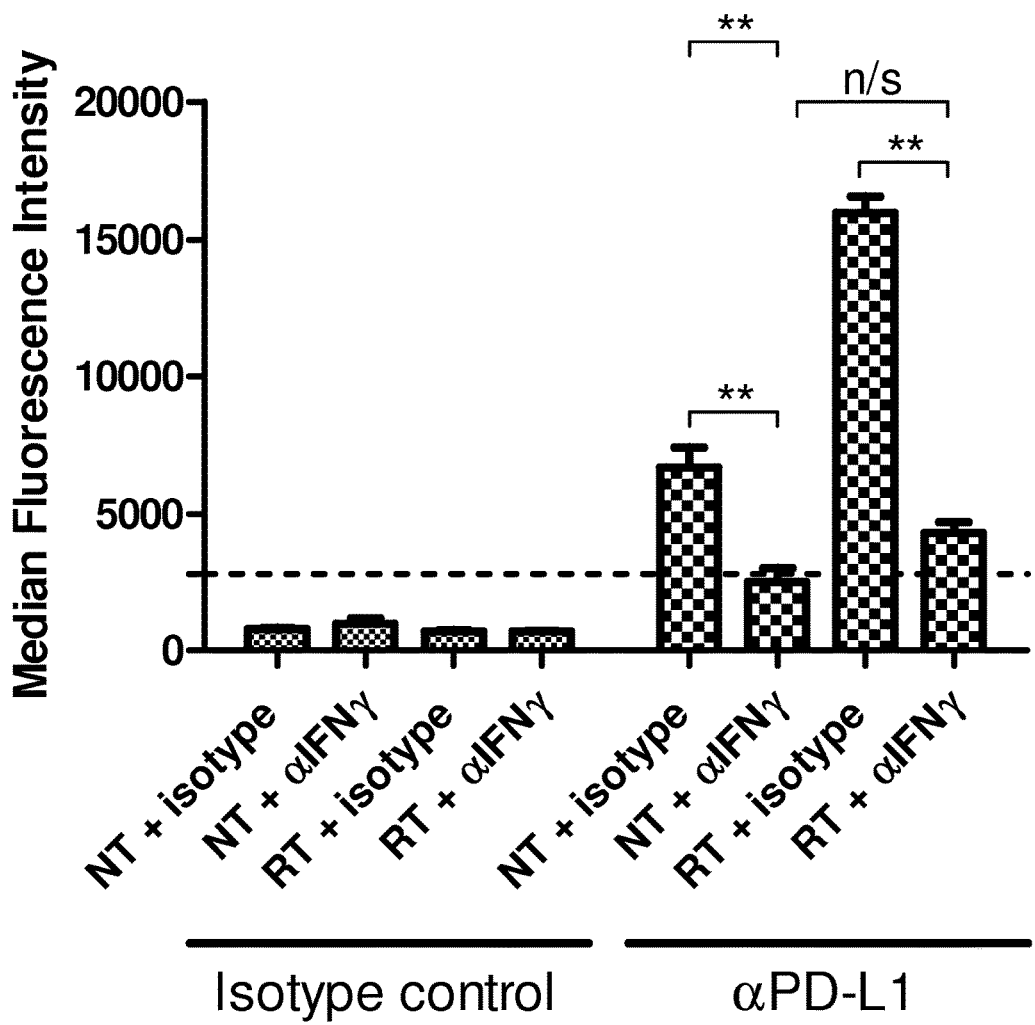

To confirm the role of IFNγ on tumor cell expression of PD-L1 in response to RT in vivo, mice received RT in combination with αIFNγ blocking antibody (or isotype control). IFNγ blockade reduced tumor cell expression of PD-L1 by 2.6 fold in NT mice to the level observed on CT26 cells cultured in vitro; suggesting adaptive upregulation of PD-L1 occurs following implantation of tumor (FIGS. 5D and E). However, the significant upregulation of PD-L1 observed following RT (2.4 fold compared to NT control) was completely abrogated by IFNγ blockade confirming this as the driver of adaptive tumor cell expression of PD-L1 following RT treatment.

Example 7

Figure 6A:
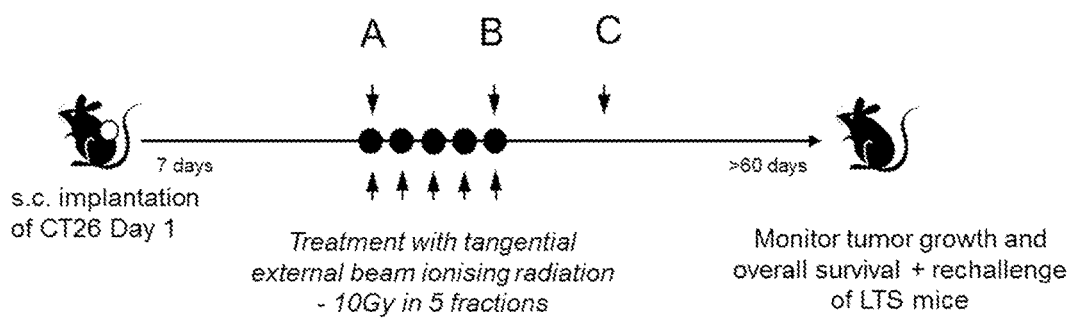
FIGS. 6A-6D demonstrate that dosing schedule impacts outcomes with RT potentiation only observed with concurrent but not sequential αPD-L1 mAb therapy.
Figure 6B:
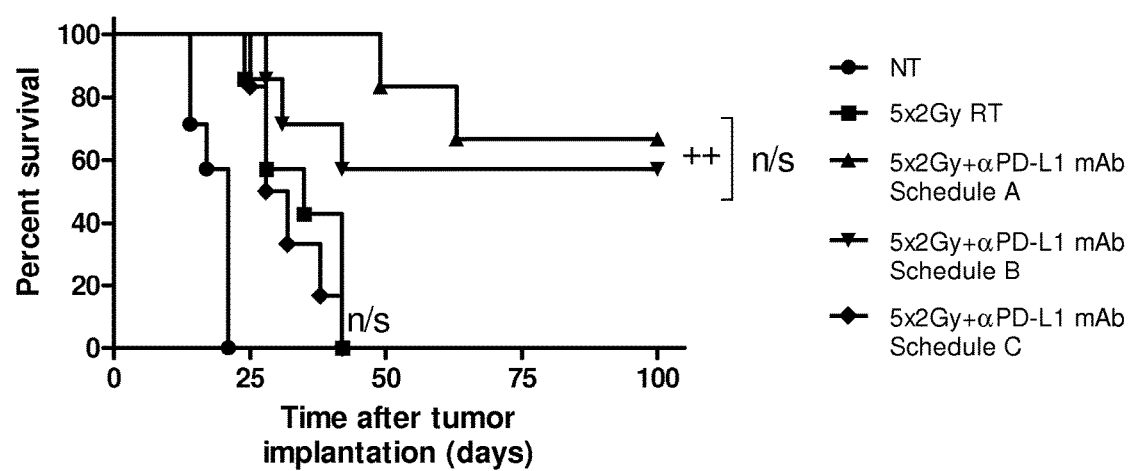
Figure 10A:
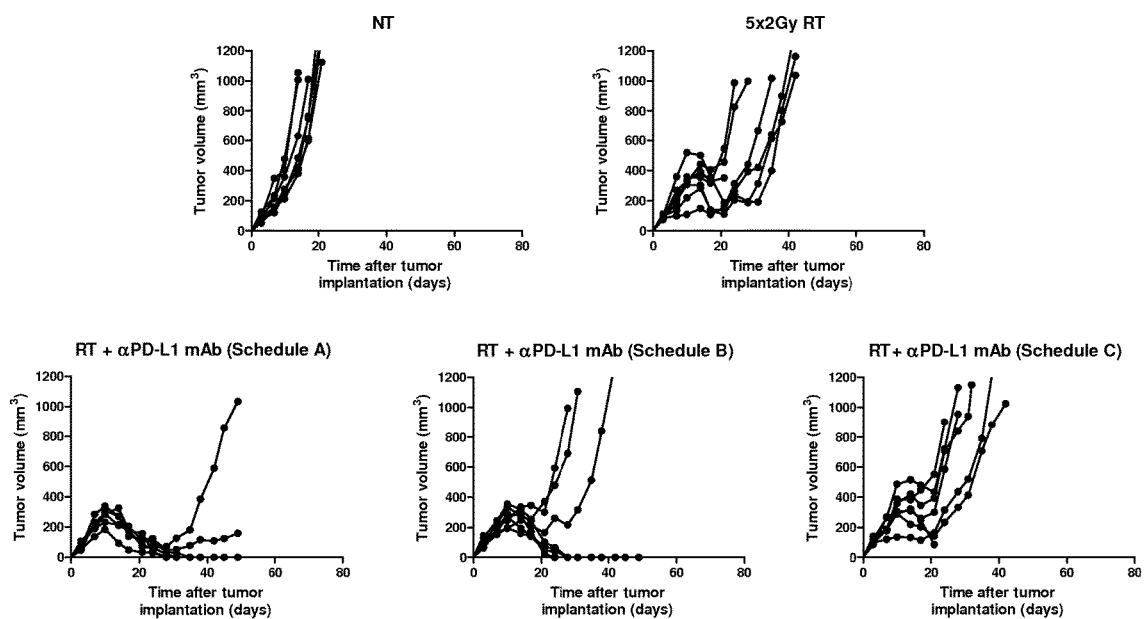
FIGS. 10A-10C show that the dosing schedule impacts outcome.
Figure 10B:
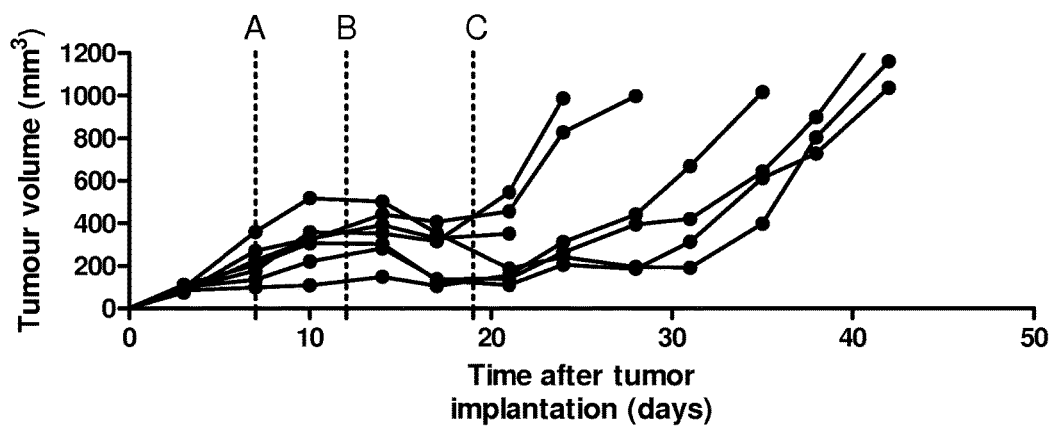
Figure 10C:
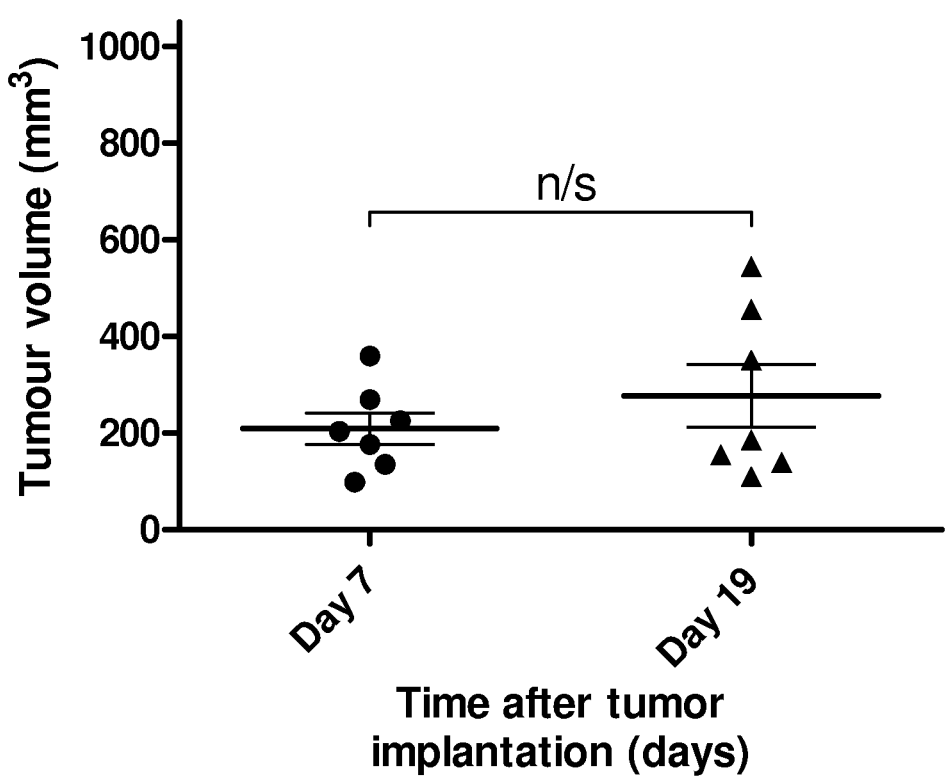

Concomitant Scheduling of αPD-L1 mAb and RT Generates an Effective Anti-tumor Immune Response We evaluated 3 distinct combination schedules where mice bearing established CT26 tumors received a fractionated RT cycle of about 10 Gy in 5 fractions with administration of αPD-L1 mAb commencing either on day 1 of the fractionated RT cycle (schedule A), day 5 of the cycle (schedule B) or 7 days after completion of RT (schedule C) (FIG. 6A). No significant difference in overall survival was found between schedule A and B with LTS of 60% and 57 respectively (P>0.05 Log-rank; Mantel-Cox test) (FIG. 6B and FIG. 10A). In contrast, sequential treatment with RT followed 7 days later by αPD-L1 mAb (Schedule C) was completely ineffective at enhancing overall survival when compared to RT alone (median survival of 30 days vs. 35 days respectively; P>0.05 Log-rank; Mantel-Cox test) despite similar tumor burden across groups (FIGS. 10B and C).

Figure 6C:
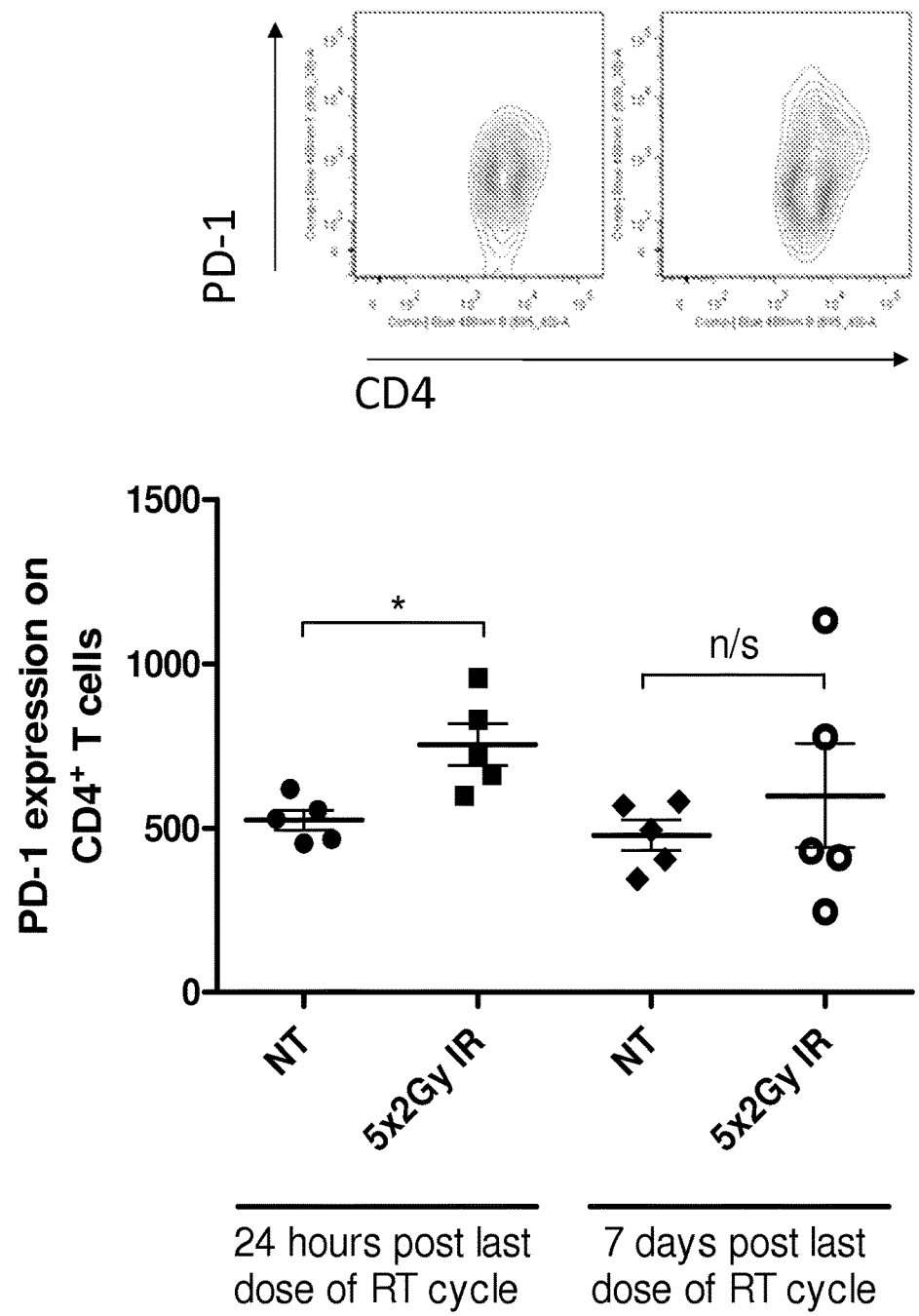
Figure 6D:
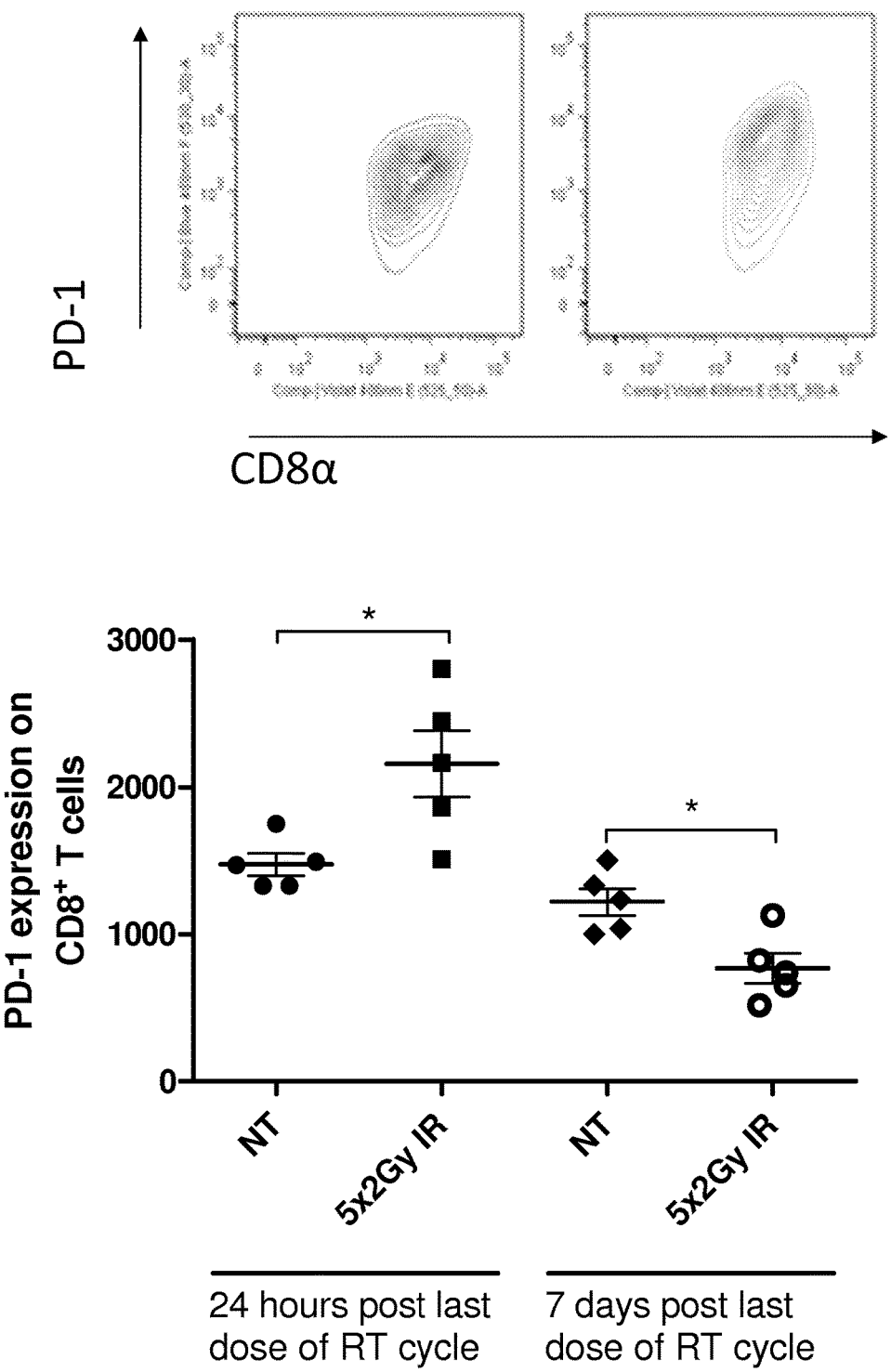
Figure 11:
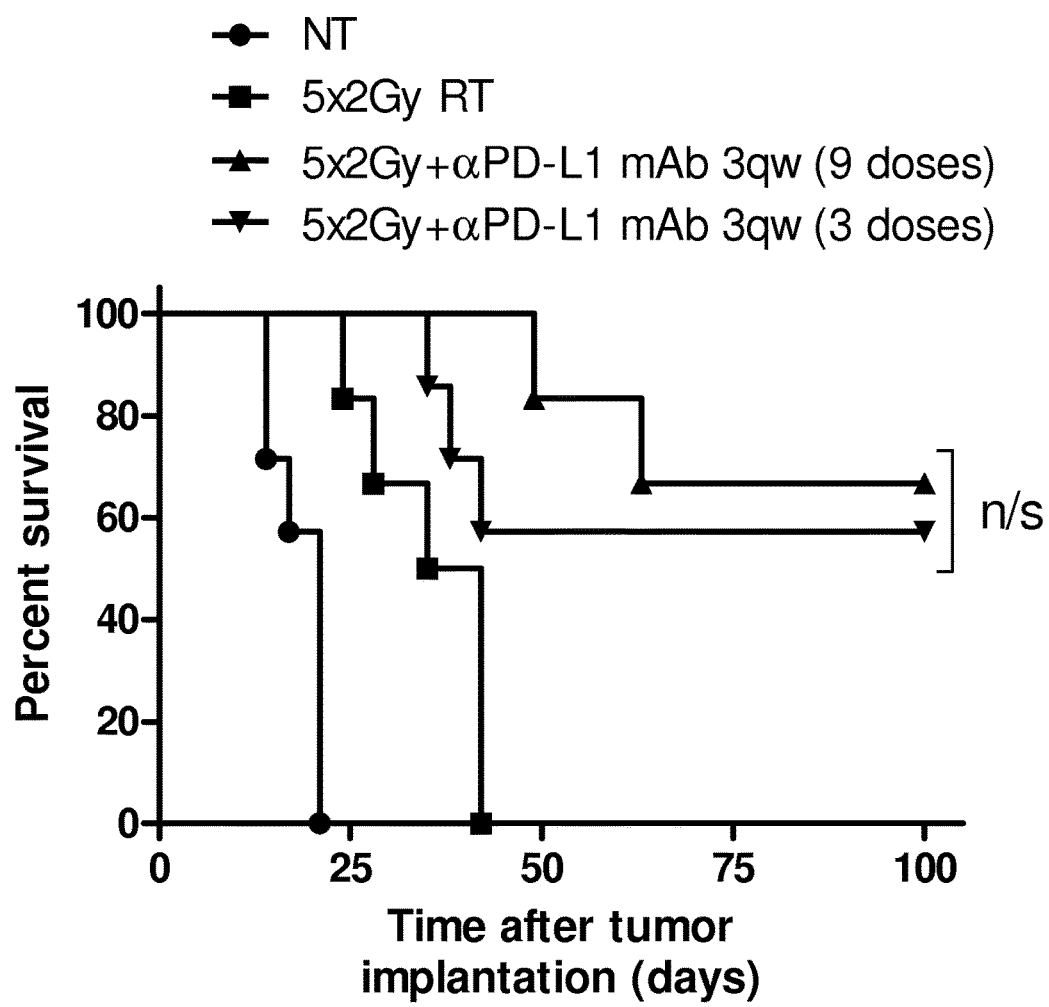
FIG. 11 shows that acute versus chronic administration of αPD-L1 mAb does not impact efficacy of combination therapy. A, CT26 tumor bearing mice received 10 Gy RT delivered in 5 daily fractions of 2 Gy either alone or in combination with αPD-L1 mAb dosed at 10 mg/kg 3qw either for 3 weeks or 1 week. Experimental groups contained at least 7 mice and are representative of at least 2 independent experiments. n/s, P>0.05, log-rank; Mantel-Cox test.

Analysis of tumor infiltrating CD4$^+$ and CD8$^+$ T cells 24 hours after the last dose of RT reveal increased expression of PD-1 when compared to time-matched NT controls (P<0.05, Mann-Whitney test) (FIG. 6C). In contrast, by 7 days post RT no change in PD-1 expression was evident on CD4$^+$ T cells and was found to be significantly decreased on CD8$^+$ T cells when compared to time-matched NT controls (P<0.05, Mann-Whitney test) (FIG. 6D). Expression of PD-1 was consistently found to be higher on tumor infiltrating CD8$^+$ than CD4$^+$ T cells (FIGS. 6C and D). We next compared activity following an acute vs. extended αPD-L1 mAb dosing protocol where mice received either 3 doses of mAb concurrent with RT or the same with dosing extended (3qw) for an additional 2 weeks. No additional benefit was observed with extended αPD-L1 mAb administration (FIG. 11).

Taken together these data demonstrate that treatment with low dose fractionated RT leads to an acute increase in PD-1 expression on T cells and that sequential therapy where blockade of the PD-1/PD-L1 signalling axis is delayed until completion of an RT cycle may be ineffective potentially due to deletion or anergy of tumor-reactive CD8$^+$ T cells.

Example 8

Discussion of Preceding Examples

Low doses of fractionated RT leads to upregulation of PD-L1 expression on tumor cells secondary to CD8$^+$ T cell production of IFNγ. In mouse models of melanoma, colorectal and breast cancer we demonstrate that the activity of RT can be enhanced through combination with αPD-L1 mAb, leading to the generation of immunological memory in long-term surviving mice which is capable of protecting against tumor recurrence. Furthermore, our data reveal that dose scheduling may affect outcomes, with concurrent but not sequential therapy effective at improving local tumor control and survival.

This is the first preclinical study to demonstrate that fractionated RT leads to increased tumor cell expression of PD-L1 through CD8$^+$ T cell production of IFNγ. Here, tumor cell expression of PD-L1 may act as a biomarker of a local anti-tumor response, suggesting that local RT may be sufficient to prime CD8$^+$ T cell responses. However, whilst treatment with RT alone was unable to generate durable anti-cancer immunity, activity was found to be enhanced through mAb-mediated blockade of either PD-1 or PD-L1 suggesting that signalling through this axis may limit the immune response to RT. We saw no significant differences in overall survival between RT delivered in combination with either αPD-1 or αPD-L1, or a combination of both mAb. Given this observation it seems likely that the activity of these mAbs when delivered in combination with RT is through blockade of PD-1/PD-L1 signalling, and not mediated through the PD-L1/CD80 or PD-1/PD-L2 axes, although further experiments are needed to confirm this.

Our preclinical data reveal that the depletion of NK cells reduced local tumor control at early time points (up to 11 days post completion of RT) but did not impact on overall survival. In addition, the depletion of NK cells did not impact tumor cell expression of PD-L1 following RT suggesting their limited contribution to local IFNγ production. In contrast, whilst depletion of CD4$^+$ T cells did not impact survival following combination therapy, substantial increases in tumor cell expression of PD-L1 post RT was observed. The depletion of CD4$^+$ T cells impacts both helper T cell and Treg populations. Although further studies are needed to delineate the relative contributions of these subpopulations of CD4$^+$ T cells we can speculate that CD4$^+$ helper T cells may be dispensable for the generation of effective CD8$^+$ T cell responses post RT/PD-L1 mAb therapy in our model and that either helper T cells, or more likely Treg, may be actively suppressing IFNγ production in the local tumor milieu. Therefore, the therapeutic potential to enhance anti-tumor responses by Treg depletion may be at least in part attenuated through enhanced tumor cell expression of PD-L1.

PD-L1 expression can be modulated by a number of cytokines including type-1 and 2 IFN, TNFα and TGFβ (16, 22, 30-32). We show that tumor cell expression of PD-L1 can be enhanced following co-culture with IFNγ and that addition of TNFα can further augment this response. However, blockade of IFNγR1 or in vivo depletion of IFNγ demonstrates dependence on IFNγ mediated signalling for upregulation of PD-L1, with TNFα alone incapable of modulating tumor cell PD-L1 expression. Interestingly, in vivo depletion of IFNγ reduces PD-L1 expression on syngeneic tumor cells, matching the expression profile of tumor cells in vitro. This suggests that the local tumor microenvironment in the absence of therapeutic intervention may foster immunologically driven tumor adaptation which may support tumor development. Similarly, in human melanocytic lesions expression of PD-L1 has been shown to co-localize with areas of CD8+ T cell infiltration and is postulated to represent an adaptive mechanism of immune escape (16). However, in our preclinical mouse models monotherapy with mAbs targeting PD-1/PD-L1 only demonstrates modest activity, suggesting that targeting this axis alone may be unlikely to bring about durable anti-tumor immune responses in all settings and underscores the requirement for a combinatorial approach.

In contrast to the use of a single 12 Gy dose (30), our results demonstrate that upregulation of PD-L1 occurs at much lower biologically effective doses involving delivery of fractionated RT using about 10 Gy in 5 daily fractions. This is an important finding given that this dose per fraction is more commonly used in routine clinical practice. Several studies have assessed the impact of RT dose fractionation; comparing single ablative doses, hypofractionated and fractionated RT, on the generation of anti-tumor immune responses and on the tumor microenvironment (4, 5, 25, 26, 33, 34). However, the results of these studies are equivocal and optimal RT delivery and the impact of RT dose fractionation on tumor cell expression of PD-L1 requires further investigation.

Previously, no research has addressed the impact of sequencing on the activity of RT and αPD-L1 mAb therapy. This is especially pertinent given the predisposition to adopting a sequenced combination regimen in the clinic as a strategy to maximize tolerability. We show that only blockade of PD-L1 at the time of RT delivery can enhance the therapeutic response in mouse models, with therapy 7 days after completion of RT no better than treatment with RT alone. In addition, our data reveal that PD-L1 expression is elevated by 24 hours after completion of a fractionated RT cycle and remains elevated for at least 7 days post completion. Moreover, we found elevated PD-1 expression on tumor infiltrating CD4+ and CD8+ T cells 24 hours post RT when compared to control cohorts. Expression of PD-1 was found to be consistently higher on CD8+ vs. CD4+ T cells. Taken together these data suggest that local fractionated RT can prime anti-tumor CD8+ T cell responses but that these may be attenuated by signalling through the PD-1/PD-L1 axis and early inhibition of this axis may generate durable effective anti-tumor responses. Further, the requirement for chronic vs. acute blockade of the PD-1/PD-L1 axis when combined with RT is unclear. We observed no difference in survival when αPD-L1 mAb was administered 3qw over 1 week concurrent with RT delivery vs. an extended schedule of up to 3 weeks. These data suggest that combination approaches with RT may permit a reduction in the duration of αPD-1/PD-L1 mAb therapy required to achieve therapeutic anti-tumor immune responses. Together these data have important implications for clinical trial design.

In summary, this study demonstrates that treatment with fractionated RT leads to upregulation of tumor cell expression of PD-L1 and that blockade of the PD-1/PD-L1 axis can enhance the immune response to fractionated RT in multiple syngeneic mouse models of cancer. Our data suggest that dose scheduling of αPD-L1 mAb with RT may generate therapeutic immune responses with the capacity to reduce tumor burden and improve survival. This therapeutic combination may be a promising approach for the treatment of many solid malignancies where RT is commonly used and translation to early phase clinical trial is clearly warranted.

Example 9

Treatment Protocols

Patient A has colorectal cancer. In week 1, patient A receives an effective amount of radiation therapy in five fractopms. In week 1, patient A also receives a therapeutic dose of MEDI4736 on day 1, day 3, and day 5. Patient A repeats this schedule for weeks 2, 3, 4, and 5.

Patient B has breast cancer. In week 1, patient B receives an effective amount of radiation therapy. In week 1, patient B also receives a therapeutic dose of MEDI4736 on day 5. Patient repeats this schedule for weeks 3, 5, and 7.

Example 10

Certain Embodiments

The following items provide certain embodiments disclosed herein.

Item 1. A method of treating cancer in a patient comprising
 a. administering at least one dose of radiation therapy; and
 b. administering at least one PD-1 and/or PD-L1 antagonist, wherein at least one PD-1 and/or PD-L1 antagonist is administered on the same day as a dose of radiation therapy or up to and including 4 days later.

Item 2. The method of item 1, wherein the at least one PD-1 and/or PD-L1 antagonist is an at least one PD-1 and/or PD-L1 antibody or functional part thereof.

Item 3. The method of any one of items 1-2, wherein the dose of radiation therapy is about 11 Gy or lower.

Item 4. The method of item 3, wherein the dose of radiation therapy is about 10 Gy or lower.

Item 5. The method of any one of items 1-4, wherein the radiation therapy is fractionated radiation therapy.

Item 6. The method of item 5, wherein the fractionated radiation therapy comprises from 2 to 7 fractions.

Item 7. The method of item 6, wherein the fractionated radiation therapy comprises 5 fractions.

Item 8. The method of any one of items 5-7, wherein the radiation therapy fractions are administered in sequential days.

Item 9. The method of any one of items 5-8, wherein the radiation therapy fractions are administered on day 1, day 2, day 3, day 4, and day 5.

Item 10. The method of any one of items 7-9, wherein the radiation therapy comprises about 10 Gy in 5 fractions.

Item 11. The method of any one of items 1-10, wherein the at least one PD-1 and/or PD-L1 antagonist is administered on day 1.

Item 12. The method of any one of items 1-11, wherein the at least one PD-1 and/or PD-L1 antagonist is administered on day 5.

Item 13. The method of any one of items 1-12, wherein the at least one PD-1 and/or PD-L1 antagonist is administered multiple times.

Item 14. The method of any one of items 1-13, wherein the at least one PD-1 and/or PD-L1 antagonist is administered 3 times a week.

Item 15. The method of any one of items 1-14, wherein the anti-PD-1 and/or PD-L1 antibody or functional part thereof is MEDI4736.

Item 16. The method of any one of items 1-15, wherein the anti-PD-1 and/or anti-PD-L1 antibody or functional part thereof is pembrolizumab, nivolumab, BMS-936558, AMP-224, or MPDL3280A.

Item 17. The method of any one of items 1-16, wherein the cancer is melanoma, colorectal cancer, or breast cancer.

Item 18. The method of any one of items 1-17, wherein more than one treatment cycle is performed.

Item 19. The method of item 18, wherein from 2-8 treatment cycles are performed.

Item 20. The method of any one of items 18-19, wherein the treatment cycles are weekly.

Item 21. The method of any one of items 18-19, wherein the treatment cycles are every other week.

REFERENCES

1. D. Verellen et al., Innovations in image-guided radiotherapy. *Nat Rev Cancer* 7, 949-960 (2007).
2. L. J. Lee et al., Innovations in radiation therapy (RT) for breast cancer. *Breast* 18 Suppl 3, S103-111 (2009).
3. E. Kapiteijn et al., Preoperative radiotherapy combined with total mesorectal excision for resectable rectal cancer. *N Engl J Med* 345, 638-646 (2001).
4. Y. Lee et al., Therapeutic effects of ablative radiation on local tumor require CD8+ T cells: changing strategies for cancer treatment. *Blood* 114, 589-595 (2009).
5. A. A. Lugade et al., Local radiation therapy of B16 melanoma tumors increases the generation of tumor antigen-specific effector cells that traffic to the tumor. *J Immunol* 174, 7516-7523 (2005).
6. L. Apetoh et al., Toll-like receptor 4-dependent contribution of the immune system to anticancer chemotherapy and radiotherapy. *Nat Med* 13, 1050-1059 (2007).
7. S. J. Gardai et al., Cell-surface calreticulin initiates clearance of viable or apoptotic cells through trans-activation of LRP on the phagocyte. *Cell* 123, 321-334 (2005).
8. F. Ghiringhelli et al., Activation of the NLRP3 inflammasome in dendritic cells induces IL-1beta-dependent adaptive immunity against tumors. *Nat Med* 15, 1170-1178 (2009).
9. Y. Ma et al., Anticancer chemotherapy-induced intratumoral recruitment and differentiation of antigen-presenting cells. *Immunity* 38, 729-741 (2013).
10. J. Honeychurch et al., Immunogenic potential of irradiated lymphoma cells is enhanced by adjuvant immunotherapy and modulation of local macrophage populations. *Leuk Lymphoma* 54, 2008-2015 (2013).
11. B. Cummings et al., Five year results of a randomized trial comparing hyperfractionated to conventional radiotherapy over four weeks in locally advanced head and neck cancer. *Radiother Oncol* 85, 7-16 (2007).
12. H. Dong et al., Tumor-associated B7-H1 promotes T-cell apoptosis: a potential mechanism of immune evasion. *Nat Med* 8, 793-800 (2002).
13. G. J. Freeman et al., Engagement of the PD-1 immunoinhibitory receptor by a novel B7 family member leads to negative regulation of lymphocyte activation. *J Exp Med* 192, 1027-1034 (2000).
14. M. J. Butte et al., Programmed death-1 ligand 1 interacts specifically with the B7-1 costimulatory molecule to inhibit T cell responses. *Immunity* 27, 111-122 (2007).
15. S. Spranger et al., Up-regulation of PD-L1, IDO, and T(regs) in the melanoma tumor microenvironment is driven by CD8(+) T cells. *Sci Transl Med* 5, 200ra116 (2013).
16. J. M. Taube et al., Colocalization of inflammatory response with B7-h1 expression in human melanocytic lesions supports an adaptive resistance mechanism of immune escape. *Sci Transl Med* 4, 127ra137 (2012).
17. M. Sznol et al., Antagonist antibodies to PD-1 and B7-H1 (PD-L1) in the treatment of advanced human cancer. *Clin Cancer Res* 19, 1021-1034 (2013).
18. J. R. Brahmer et al., Phase I study of single-agent anti-programmed death-1 (MDX-1106) in refractory solid tumors: safety, clinical activity, pharmacodynamics, and immunologic correlates. *J Clin Oncol* 28, 3167-3175 (2010).
19. J. R. Brahmer et al., Safety and activity of anti-PD-L1 antibody in patients with advanced cancer. *N Engl J Med* 366, 2455-2465 (2012).
20. O. Hamid et al., Safety and tumor responses with lambrolizumab (anti-PD-1) in melanoma. *N Engl J Med* 369, 134-144 (2013).
21. E. J. Lipson et al., Durable cancer regression off-treatment and effective reinduction therapy with an anti-PD-1 antibody. *Clin Cancer Res* 19, 462-468 (2013).
22. A. Kondo et al., Interferon-gamma and tumor necrosis factor-alpha induce an immunoinhibitory molecule, B7-H1, via nuclear factor-kappaB activation in blasts in myelodysplastic syndromes. *Blood* 116, 1124-1131 (2010).
23. S. L. Topalian et al., Safety, activity, and immune correlates of anti-PD-1 antibody in cancer. *N Engl J Med* 366, 2443-2454 (2012).
24. S. L. Topalian et al., Durable Tumor Remission, and Long-Term Safety in Patients With Advanced Melanoma Receiving Nivolumab. *J Clin Oncol*, (2014).
25. M. Z. Dewan et al., Fractionated but not single-dose radiotherapy induces an immune-mediated abscopal effect when combined with anti-CTLA-4 antibody. *Clin Cancer Res* 15, 5379-5388 (2009).
26. S. J. Dovedi et al., Systemic delivery of a TLR7 agonist in combination with radiation primes durable antitumor immune responses in mouse models of lymphoma. *Blood* 121, 251-259 (2013).
27. J. Honeychurch et al., Anti-CD40 monoclonal antibody therapy in combination with irradiation results in a CD8 T-cell-dependent immunity to B-cell lymphoma. *Blood* 102, 1449-1457 (2003).
28. B. C. Burnette et al., The efficacy of radiotherapy relies upon induction of type i interferon-dependent innate and adaptive immunity. *Cancer Res* 71, 2488-2496 (2011).
29. J. Y. Kim et al., Increase of NKG2D ligands and sensitivity to NK cell-mediated cytotoxicity of tumor cells by heat shock and ionizing radiation. *Exp Mol Med* 38, 474-484 (2006).
30. L. Deng et al., Irradiation and anti-PD-L1 treatment synergistically promote antitumor immunity in mice. *J Clin Invest* 124, 687-695 (2014).
31. J. N. Ou et al., TNF-alpha and TGF-beta counter-regulate PD-L1 expression on monocytes in systemic lupus erythematosus. *Sci Rep* 2, 295 (2012).
32. S. Terawaki et al., IFN-alpha directly promotes programmed cell death-1 transcription and limits the duration of T cell-mediated immunity. *J Immunol* 186, 2772-2779 (2011).
33. D. Schaue et al., Maximizing tumor immunity with fractionated radiation. *Int J Radiat Oncol Biol Phys* 83, 1306-1310 (2012).

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited value) that one of ordinary skill in the art would consider equivalent to the recited value (e.g., having the same function or result). In some instances, the term about may include numerical values that are rounded to the nearest significant figure.

What is claimed is:

1. A method of treating cancer in a patient comprising
   a. administering to the patient a fraction of fractionated radiation therapy; and
   b. administering to the patient at least one PD-1 and/or PD-L1 antagonist, wherein the at least one PD-1 and/or PD-L1 antagonist is administered on the same day as the fraction of radiation therapy or up to and including 4 days later, wherein the fraction is 2.2 Gy or lower, and wherein the cancer is bladder cancer, breast cancer, colorectal cancer, head and neck cancer, liver cancer, lung cancer, ovarian cancer, pancreatic cancer or renal cancer.

2. The method of claim 1, wherein the at least one PD-1 and/or PD-L1 antagonist is an at least one PD-1 and/or PD-L1 antibody or functional part thereof.

3. The method of claim 1, wherein the patient is administered fractions of radiation therapy that total about 70 Gy or lower.

4. The method of claim 3, wherein the patient is administered fractions of radiation therapy that total about 50 Gy or lower.

5. The method of claim 1, wherein the fractionated radiation therapy comprises from 2 to 7 fractions.

6. The method of claim 5, wherein the fractionated radiation therapy comprises 5 fractions.

7. The method of claim 6, wherein the radiation therapy fractions are administered in sequential days.

8. The method of claim 7, wherein the radiation therapy fractions are administered on day 1, day 2, day 3, day 4, and day 5.

9. The method of claim 1, wherein the at least one PD-1 and/or PD-L1 antagonist is administered on day 1.

10. The method of claim 1, wherein the at least one PD-1 and/or PD-L1 antagonist is administered on day 5.

11. The method of claim 1, wherein the at least one PD-1 and/or PD-L1 antagonist is administered multiple times.

12. The method of claim 11, wherein the at least one PD-1 and/or PD-L1 antagonist is administered 3 times a week.

13. The method of claim 2, wherein the anti-PD-1 and/or PD-L1 antibody or functional part thereof is MEDI4736.

14. The method of claim 2, wherein the anti-PD-1 and/or anti-PD-L1 antibody or functional part thereof is pembrolizumab, nivolumab, BMS-936558, AMP-224, or MPDL3280A.

15. The method of claim 1, wherein treatment cycles are weekly or every other week.

16. The method of claim 1, wherein more than one treatment cycle is performed.

17. The method of claim 16, wherein from 2-8 treatment cycles are performed.

\* \* \* \* \*